US006479504B1

(12) United States Patent
Macfarlane et al.

(10) Patent No.: US 6,479,504 B1
(45) Date of Patent: Nov. 12, 2002

(54) ANTAGONISM OF IMMUNOSTIMULATORY CPG-OLIGONUCLEOTIDES BY 4-AMINOQUINOLINES AND OTHER WEAK BASES

(75) Inventors: Donald E. Macfarlane, Iowa City, IA (US); Lucjan Strekowski, Stone Mountain, GA (US); Lori Manzel, Cedar Rapids, IA (US); Fyaz M. D. Ismail, Stockton on Tees (GB); Gordon B. Barlin, Turner (AU)

(73) Assignees: The University of Iowa Research Foundation, Iowa City, IA (US); Georgia State University Research Foundation, Inc., Atlanta, GA (US); The United States of America as represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 09/595,875

(22) Filed: Jun. 16, 2000

Related U.S. Application Data

(60) Provisional application No. 60/139,544, filed on Jun. 16, 1999.

(51) Int. Cl.[7] .................... A61K 31/44; A61K 31/47; C07D 219/10; C07D 215/38
(52) U.S. Cl. .................. 514/297; 514/312; 514/313; 546/105; 546/159; 546/160
(58) Field of Search .................. 574/297, 312, 574/313; 546/105, 160, 159

(56) References Cited

U.S. PATENT DOCUMENTS

| | | | | |
|---|---|---|---|---|
| 4,016,100 A | | 4/1977 | Suzuki et al. ............... | 252/316 |
| 4,089,801 A | | 5/1978 | Schneider ................... | 252/316 |
| 4,234,871 A | | 11/1980 | Guglielmi et al. .......... | 340/365 |
| 4,485,054 A | | 11/1984 | Mezei et al. ................ | 264/4.6 |
| 5,304,554 A | * | 4/1994 | Strekowski | |
| 5,886,185 A | * | 3/1999 | Chou | |
| 6,127,116 A | | 10/2000 | Rice et al. .................. | 435/6 |
| 6,174,897 B1 | * | 1/2001 | Schohe-loop | |

FOREIGN PATENT DOCUMENTS

| | | |
|---|---|---|
| EP | 0 607 439 | 7/1994 |
| WO | WO 93/07126 | 4/1993 |
| WO | WO 95/35287 | 12/1995 |
| WO | 98-30218 | * 7/1998 |

OTHER PUBLICATIONS

Strekowski, CA 114:247099, 1991.*
Zhao, CA 120:152979, 1994.*
Kereev, CA 123:74211, 1995.*
MacFarlane, CA 128:225675, 1998.*
Strekowski, CA 131:193716, 1999.*
Manzel, CA 132:102569, 1999.*
Hansen, CA 99:122257, 1983.*
Wainwright, CA 129:272864, 1998.*
Ballas et al., "Induction of NK activity in murine and human cells by CPG motifs in oligodeoxynucleotides and bacterial DNA," *J. Immunology*, 157:1840–1845, 1996.
Fox, "Mechanism of action of hydroxychloroquine as an antirheumatic drug," *Sem. Arthritis Rheumatism*, 23:82–91, 1993.
Ismail et al., "An exploration of the structure–activity relationships of 4–aminoquinolines: novel antimalarials with activity in–vivo," *J. Pharm. Pharmacol.*, 48:841–850, 1996.
Krieg et al., "CpG motifs in bacterial DNA trigger Direct B–cell activation," *Nature*, 374:546–549, 1995.
Krieg et al., "Oligodeoxynucleotide modifications determine the magnitude of B cell stimulation by CpG motifs," *Antisense Nucleic Acid Drug Dev.*, 6:133–139, 1996.
MacFarlane and Manzel, "Antagonism of immunostimulatory CpG–oligodeoxynucleotides by quinacrine, chloroquine and structurally related compounds," *J. Immunol.*, 160:1122–1131, 1998.
MacFarlane et al., "Unmethylated CpG–containing oligodeoxynucleotides inhibit apoptosis in WEHI 231 B–lymphocytes induced by several agents: evidence for blockade at a distal signaling step," *Immunology*, 91:586–593, 1997.
Mokrosz et al., "4–(3–furyl)–2–(4–methylpiperazino)pyrimidines: potent 5–ht$_{2A}$ receptor antagonists," *Bioorganic & Medicinal Chemistry Letters*, 7:1635–1638, 1997.
Mokrosz et al., "4,6–di(heteroaryl)–2–(N–methylpiperazino) pyrimidines as new, potent 5–ht$_{2A}$ receptor ligands: a verification of the topographic model," *Arch. Pharm.*, 328:659–666, 1995.
Mokrosz et al., "Structure–activity relationship studies of CNS agents. Part 29. N–methylpiperazino–substituted derivatives of quinazoline, phthalazine and quinoline as novel $\alpha_1$, 5–ht$_{1A}$ and 5–ht$_{2A}$ receptor ligands," *Eur J Med Chem*, 31:973–980, 1996.
Strekowski et al., "Amination oby lithium alkyulamide reagents of ketimines derived from 2–(trifluoromethyl)anilines and methyl halophenyl ketones and their cyclization products 2–(halophenyl)quinolin–4–amines," *Tetrahedron*, 52:3273–3282, 1996.
Strekowski et al., "Design of RNA interactive anti–HIV–1 agents," *Curr. Topics in Med. Chem.* 1:33–41, 1993.

(List continued on next page.)

Primary Examiner—D. Margaret Seaman
(74) Attorney, Agent, or Firm—Fulbright & Jaworski LLP

(57) ABSTRACT

The present invention relates generally to the field of immunology. More particularly it concerns compositions and methods for inhibiting stimulation of the immune system. The compounds and methods comprise compounds that are analogs and derivatives of chloroquine, such as 4-aminoquinolines, and other weak bases. They can be used in preventative and therapeutic treatments of autoimmune diseases and phenomena, transplant rejection such as host-versus-graft disease, and sepsis.

49 Claims, 39 Drawing Sheets

OTHER PUBLICATIONS

Strekowski et al., "Further studies on the cyclization of aromatic azomethines ortho–substituted with a trifluoromethyl group: Synthesis of 2,4–di– or 2,3,4–trisubstituted quinolines," *Org. Chem.*, 57:196–201, 1992.

Strekowski et al., "Practical synthesis of 4–chloro–2–(2–naph–thylquinoline, a precursor to triple–helix dna intercalators," *Org. Process Res. Dev.*, 1:384–386, 1997.

Strekowski et al., "Quantitative structure–acitivity relationship analysis of cation–substituted polyaromatic compounds as potentiators (amplifiers) of bleomycin–mediated degradation of DNA," *J. Med. Chem.*, 34:580–588, 1991.

Strekowski et al., "Synthesis and structure–DNA binding relationship analysis of DNA triple–helix specific intercalators." *J. Med. Chem.* 39:3980–3983, 1996.

Strekowski et al., "The o–amino–trifluoromethyl functionality as a novel synthon for 4–fluoroquinolines," *J. Org. Chem.*, 59:5886–5890, 1994.

Wilson et al., "DNA triple–helix specific intercalators as antigene enhancers: unfused aromatic cations," *Biochemistry*, 32:10614–10621, 1993.

Wilson et al., "The search for structure–specific nucleic acid–interactive drugs: effects of compound structure on RNA versus DNA interaction strength," *Biochemistry*, 32:4098–4104, 1993.

Yi et al., "CpG DNA rescue of murine B lymphoma cells from anti–IgM induced growth arrest and programmed cell death is associated with increased expression of c–myc and $bcl_{xL}$–1,2," *J. Immunol.*, 157:4918–4925, 1996.

Yi et al., "CpG motifs in bacterial DNA active leukocytes through the pH–dependent generation of reactive oxygen species," *J. Immunol.*, 160:4755–4761, 1998.

Krieg et al., "Lymphocyte activation by CpG dinucleotide motifs in prokaryotic DNA," *Trends Microbiol.*, 4:73–6, 1996.

Wallace, "Antimalarial agents and lupus," *Rheumatic Disease Clinics of Portly America*, 20:243–263, 1994.

Strekowski et al., "Structure–activity relationship analysis of substituted 4–?quinolinamines, antagonists of immunostimulatory CpG–oligodeoxynucleotides," *Bioorganic & Medicinal Chem Letter* 9:1819–1824, 1999.

* cited by examiner

358 OZ-162 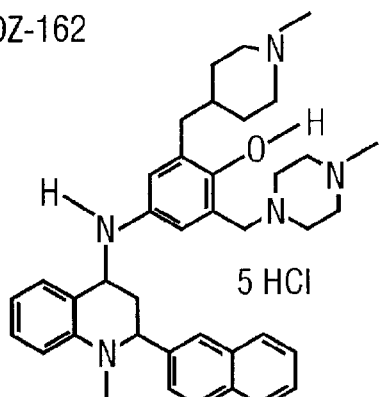
9.62 Strekowski
5 HCl
173 LJ-264/2 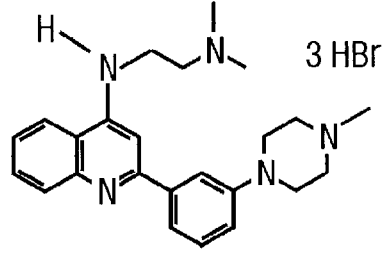
8.94 Strekowski
3 HBr
361 OZ-148 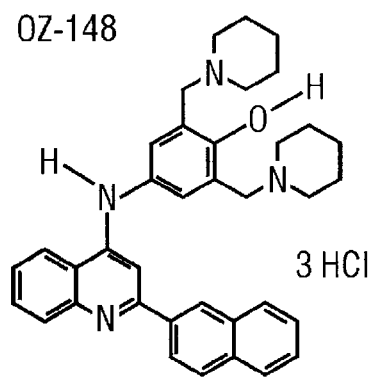
8.94 Strekowski
3 HCl
363 OZ-146 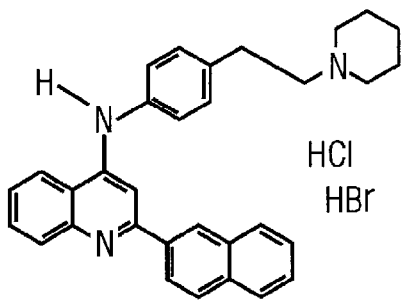
8.86 Strekowski
HCl HBr
359 OZ-144 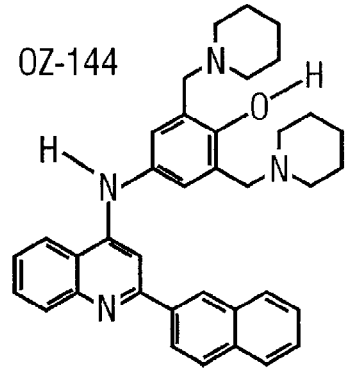
8.83 Strekowski
362 OZ-145 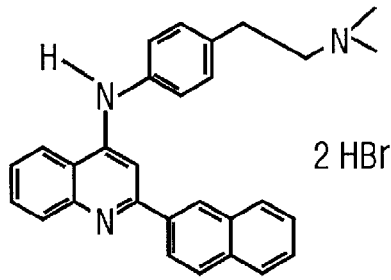
8.79 Strekowski
2 HBr
*FIG. 1A-1*

337 OZ-83
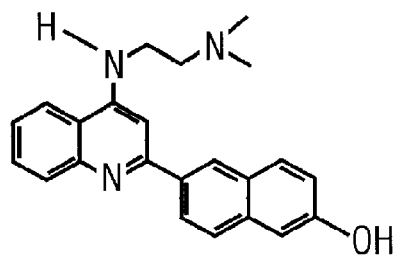
8.74 | Strekowski
372 MHQ-17
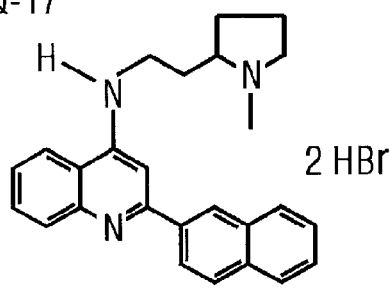
2 HBr
8.69 | Strekowski
348 MHQ-4
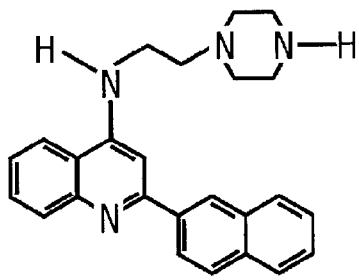
8.46 | Strekowski
371 MHQ-15
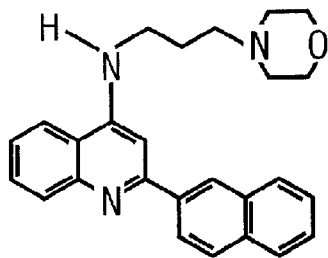
8.45 | Strekowski
*FIG. 1A-2*

341 OZ-115
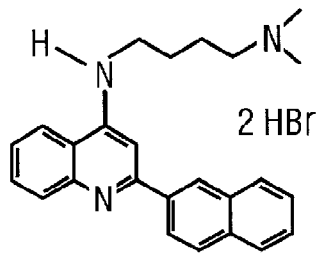
8.40 | Strekowski
171 LJ-271
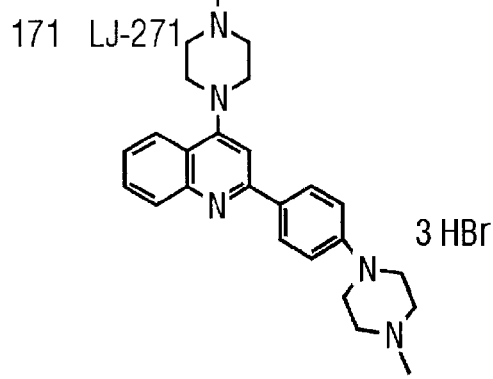
8.30 | Strekowski
349 MHQ-5
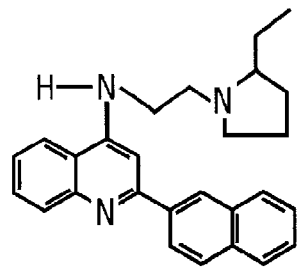
8.27 | Strekowski
350 OZ-123
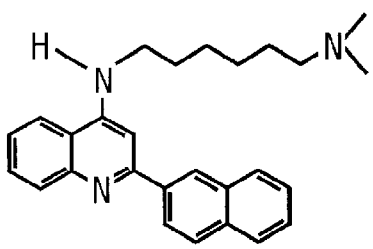
8.23 | Strekowski
177 LJ-286
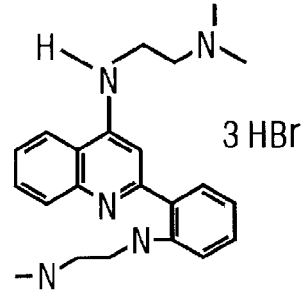
8.19 | Strekowski
178 SP-103
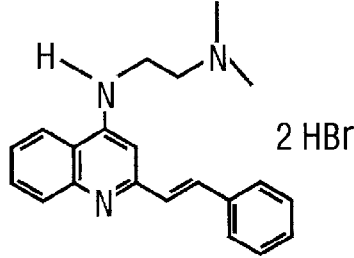
8.19 | Strekowski
FIG. 1B-1

400 MS-42
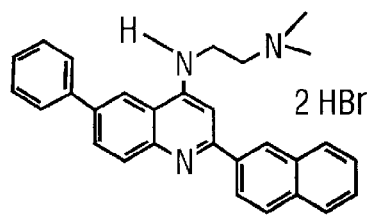
8.19  Strekowski
278 OZ-85
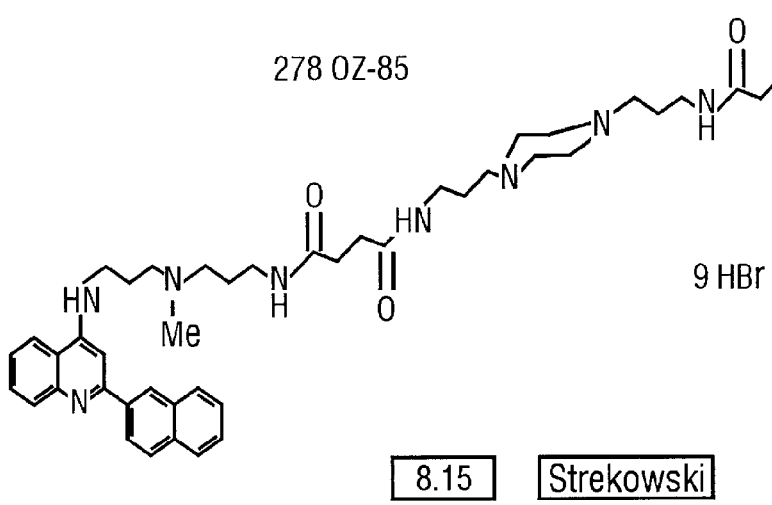
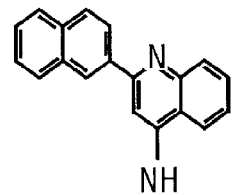
9 HBr
8.15  Strekowski
107 TMTN 1
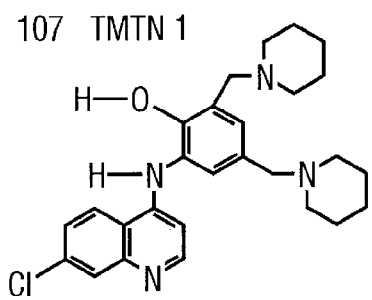
8.12  Kotecka
275 OZ-45
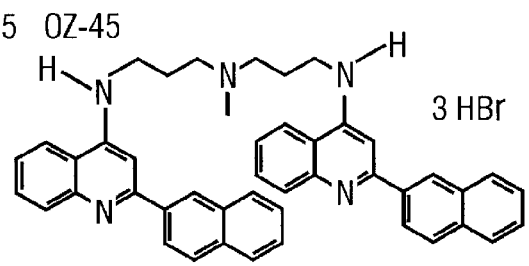
3 HBr
8.12  Strekowski
FIG. 1B-2

91 LS-B 
8.04 Strekowski
VI 5/39 VH-154 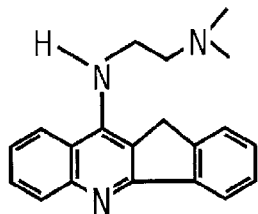
8.04 Strekowski
109 TMTN 11 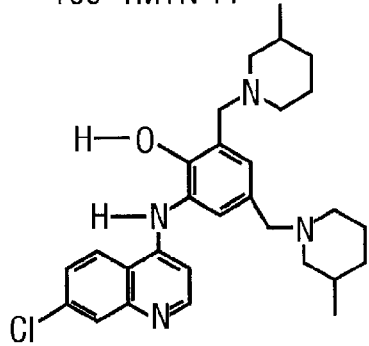
8.04 Kotecka
211 M-40 4 HBr 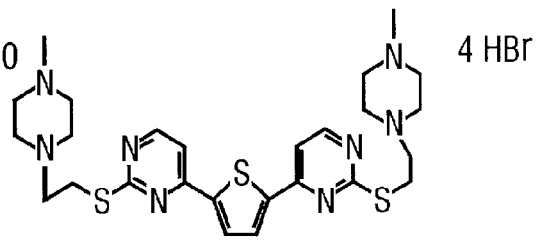
8.04 Strekowski
318 Trans 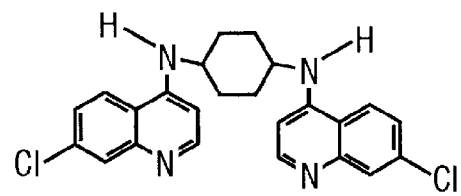
8.01 Ismall
360 OZ-153 3 HCl 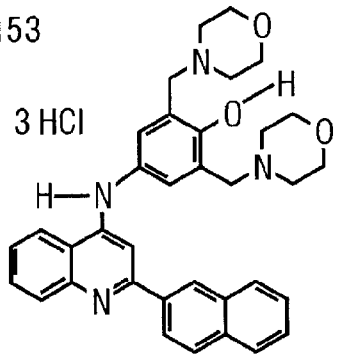
8.00 Strekowski
FIG. 1C-1

26
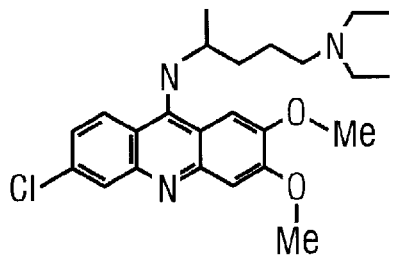
[7.99] [NCI]
94 TG-84
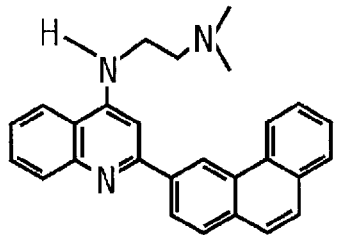
[7.96] [Strekowski]
197 LJ-247/1
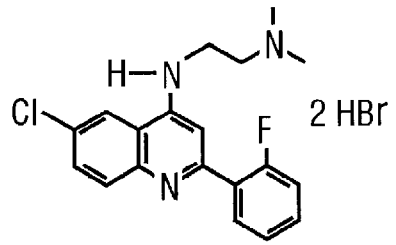
2 HBr
[7.96] [Strekowski]
279 OZ-101
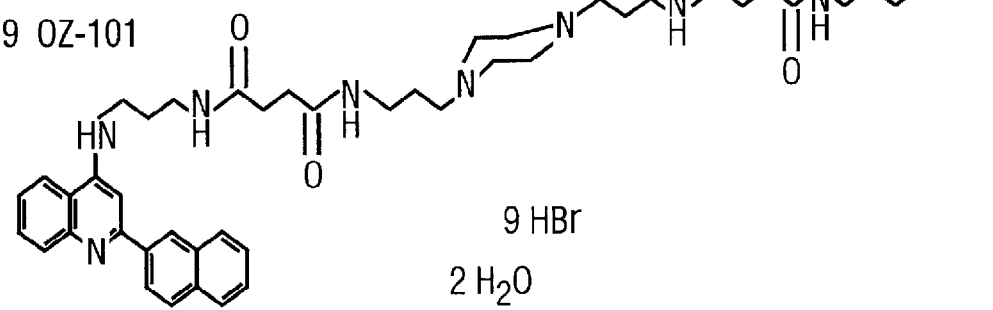
9 HBr
2 H₂O
[7.96] [Strekowski]
*FIG. 1C-2*

280 OZ-109

7.96 | Strekowski

324 Trans 7.94 | Ismall

394 MHQ-42

7.94 | Strekowski

395 MHQ-46

7.91 | Strekowski

179 LJ-228

7.88 | Strekowski

395 MHQ-28

7.88 | Strekowski

401 MS-49

7.88 | Strekowski

367 MHQ-9

7.87 | Strekowski

403 MS-41

7.86 | Strekowski

17 Quinocrine 7.85 | Sigma

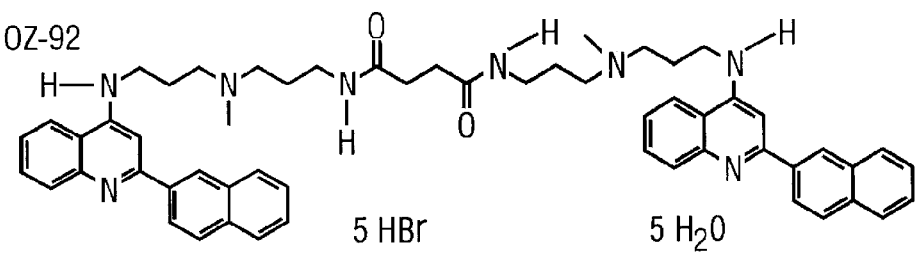
277 OZ-92
5 HBr    5 H₂O
| 7.77 | Strekowski |
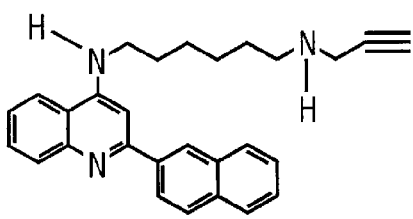
| 7.77 | Strekowski |
102 TN 112
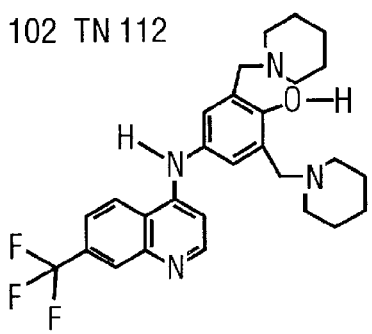
| 7.76 | Kotecka |
110 TMTN 24
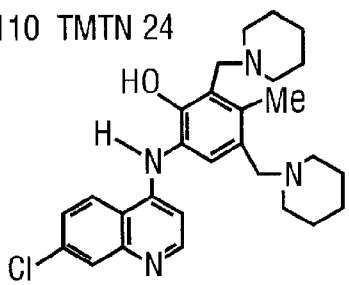
| 7.76 | Kotecka |
271 G 158-3
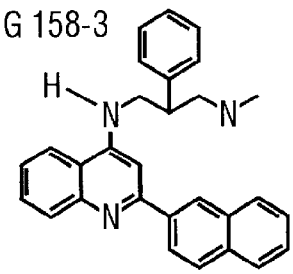
| 7.76 | Strekowski |
268 OZ-91
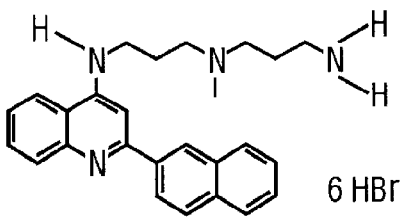
6 HBr
| 7.74 | Strekowski |
*FIG. 1F-1*

329 trans (+/-)
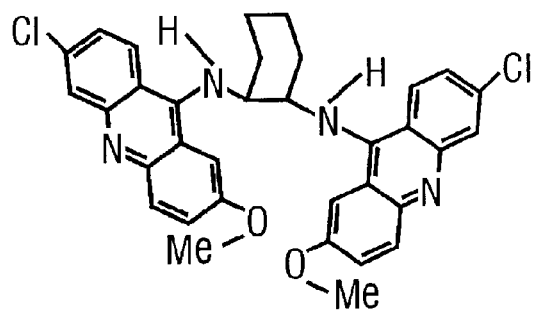
| 7.74 | Ismall |
382 MHQ-27
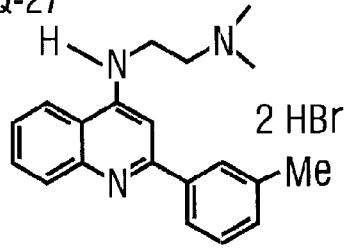
2 HBr
| 7.74 | Strekowski |
368 MHQ-11
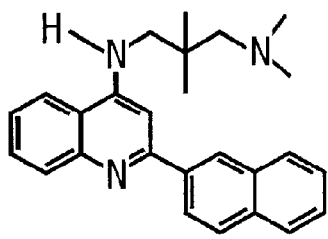
| 7.73 | Strekowski |
25
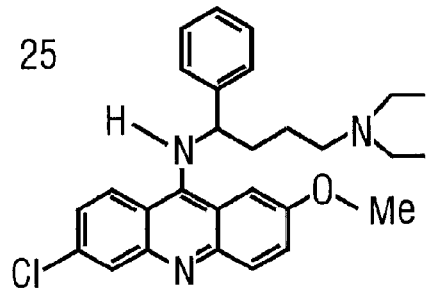
| 7.72 | NCI |
*FIG. 1F-2*

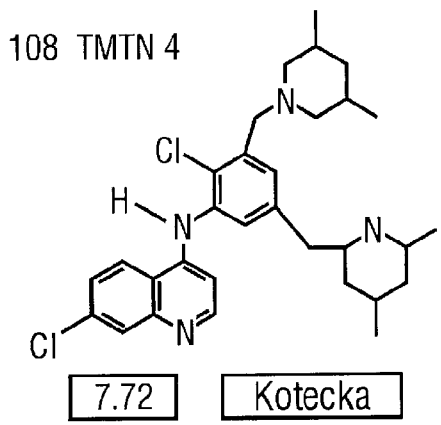
108 TMTN 4
| 7.72 | Kotecka |
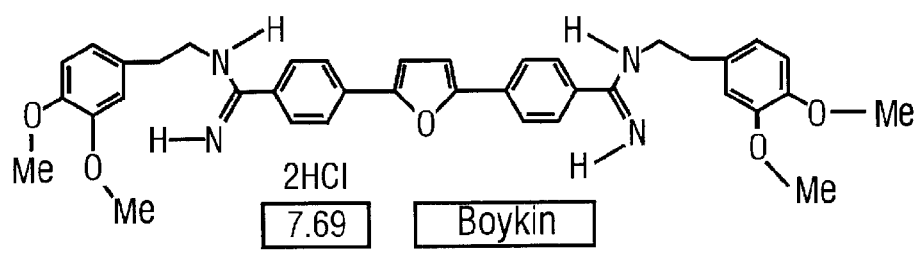
2HCl
| 7.69 | Boykin |
128 M-149/2
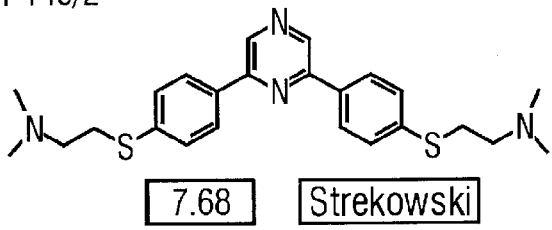
| 7.68 | Strekowski |
34
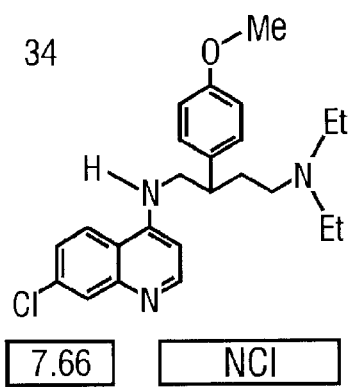
| 7.66 | NCI |
FIG. 1G-1

391 MHQ-45
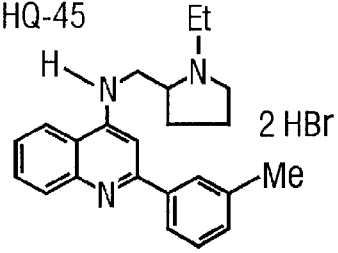
| 7.66 | Strekowski |
38
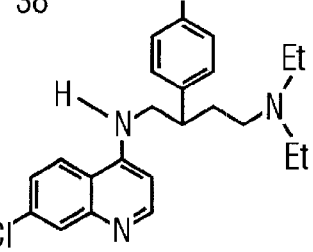
| 7.65 | NCl |
176 TG-96
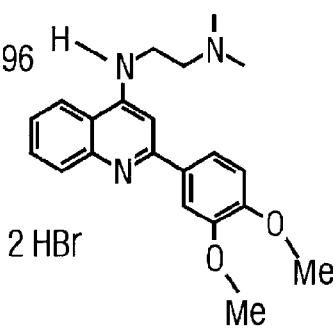
| 7.65 | Strekowski |
293 DB 431
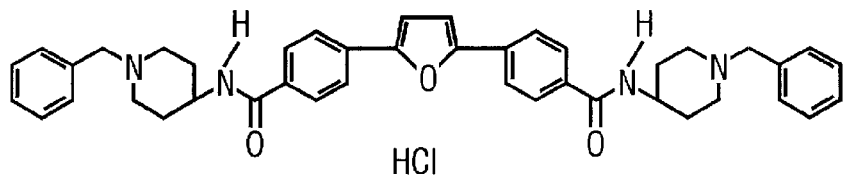
| 7.65 | Boykin |
325 trans rr
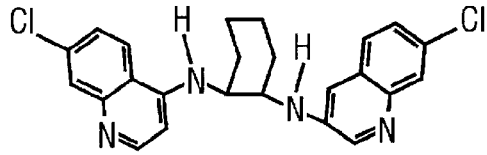
| 7.65 | |
328 trans (+/-)
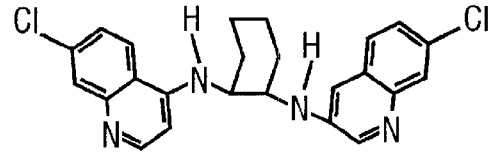
| 7.65 | Ismail |
*FIG. 1G-2*

24
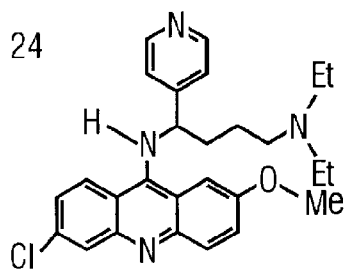
7.62  NCI
43
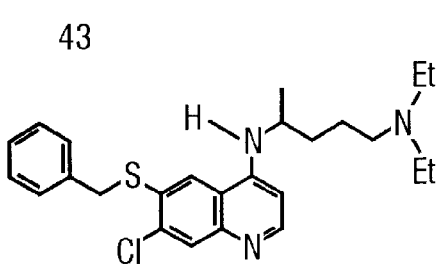
7.62  NCI
104 TN 121
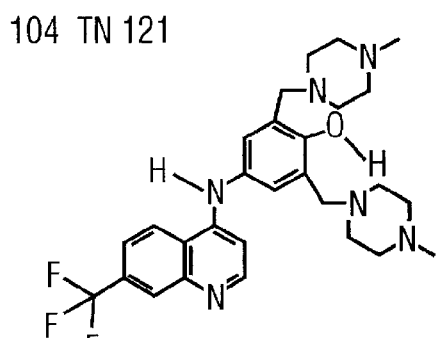
7.60  Kotecka
124 M-61
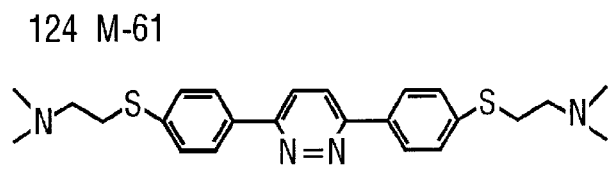
2 HBr
7.60  Strekowski
269 OZ-31
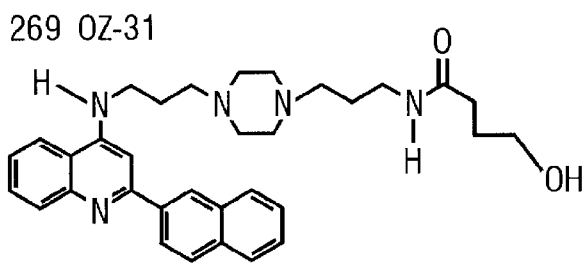
7.60  Strekowski
368 MHQ-38
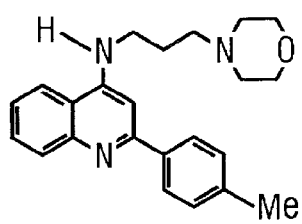
7.57  Strekowski
*FIG. 1H-1*

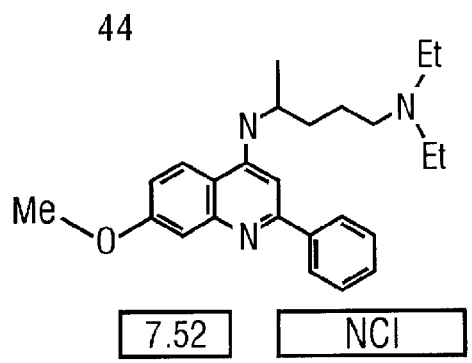
44
7.52 | NCl
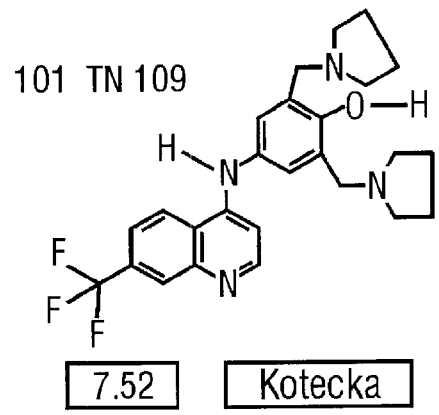
101 TN 109
7.52 | Kotecka
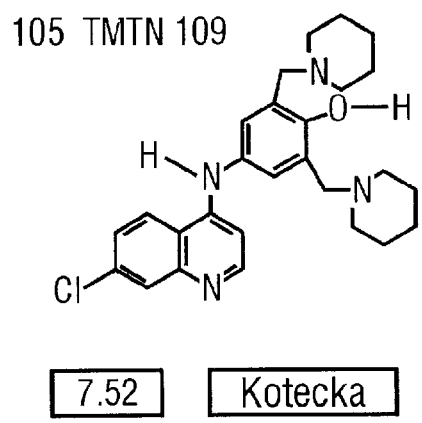
105 TMTN 109
7.52 | Kotecka
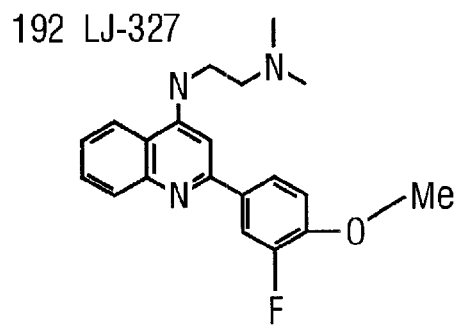
192 LJ-327
7.45 | Strekowski
FIG. 1H-2

210 MC-151
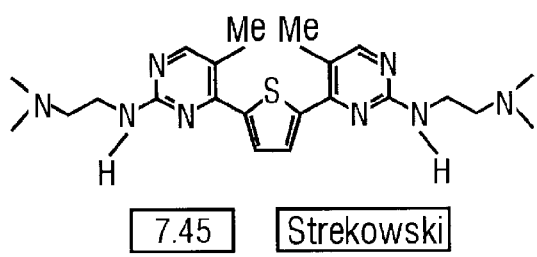
7.45 | Strekowski
33
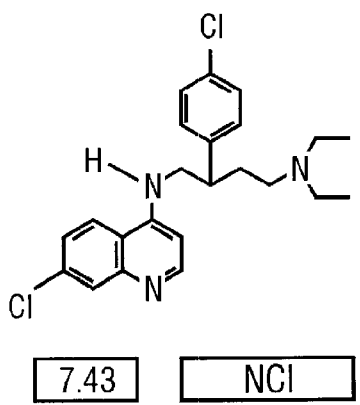
7.43 | NCI
69
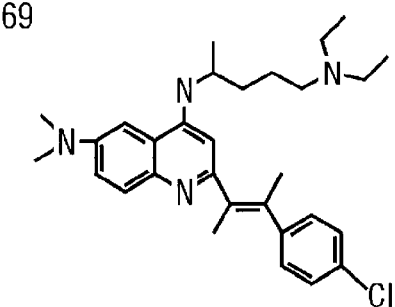
7.42 | NCI
97 AK-199
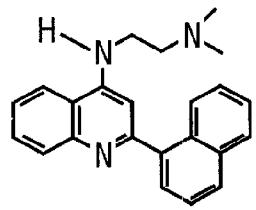
7.40 | Strekowski
103 TN 119
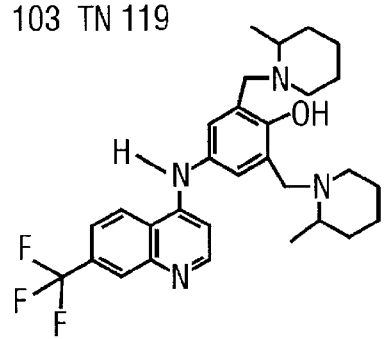
7.40 | Kotecka
121 M-25
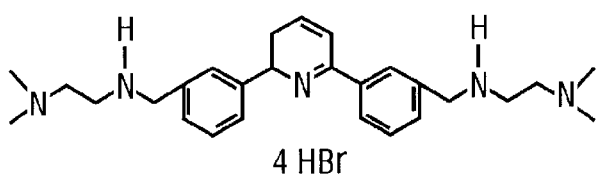
4 HBr
7.38 | Strekowski
*FIG. 1I-1*

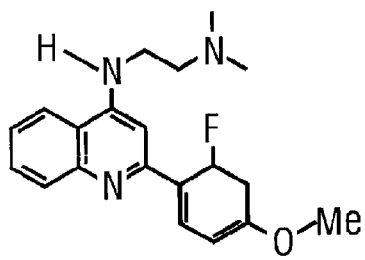
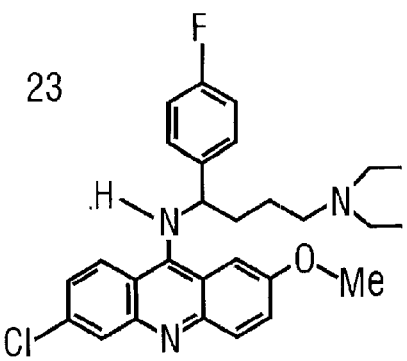
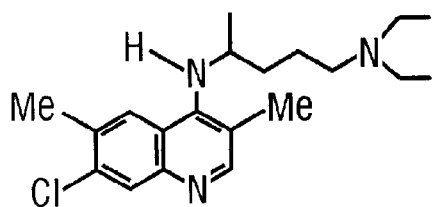
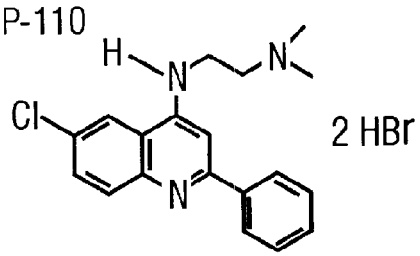
*FIG. 1I-2*

270 G 215-2

7.32 | Strekowski

175 TG-99

2 HBr 7.31 | Strekowski

122 M-95

7.30 | Strekowski

385 MHQ-37

7.30 | Strekowski

48

7.29 | NCI

195 LJ-267

7.29 | Strekowski

30

7.28 | NCI

174 TG-98

2 HBr 7.26 | Strekowski

29

7.24 | NCI

27

7.22 | NCI

28

7.22 | NCl

7

7.20 | NCl

212 M-BA

2 HBr
7.19 | Strekowski

51

7.17 | NCl

60

7.15 | NCl

196 LJ-266

2 HBr
7.14 | Strekowski

274 OZ-44

7.14 | Strekowski

42

7.13 | NCl

56

7.12 | NCl

93 LS-12

7.12 | Strekowski

FIG. 1L 59 
6.96 | Molecular Probes 36 
6.94 | NCI

100 TN-108 
6.92 | Kotecka

164 AK-195 
6.88 | Strekowski 35 
6.87 | NCI 53 
6.87 | NCI 68 
6.87 | NCI

163 X-37 
6.87 | Strekowski

172 LJ-256/2 
6.87 | Strekowski 61 
6.86 | NCI

184 LJ-323
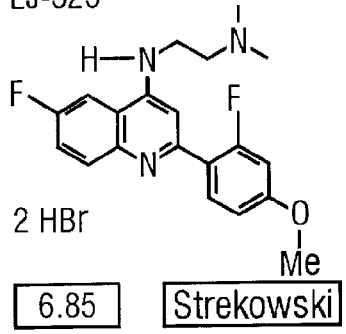
2 HBr
6.85 | Strekowski
213 M-12
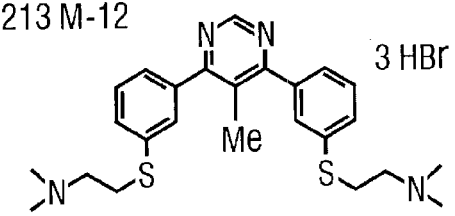
3 HBr
6.85 | Strekowski
263
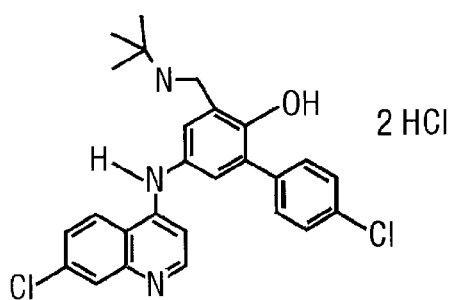
2 HCl
6.85 | WRAIR
9
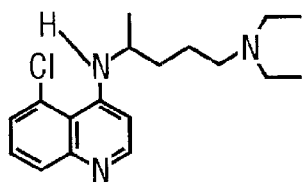
6.84 | NCI
50
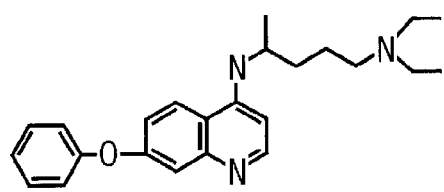
6.83 | NCI
4
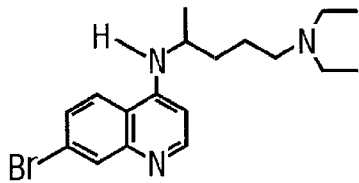
6.82 | NCI
*FIG. 1N-1*

10
198 LJ-331
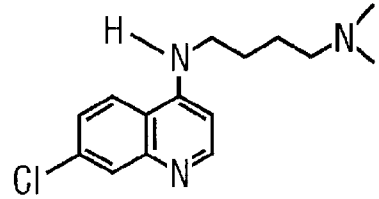
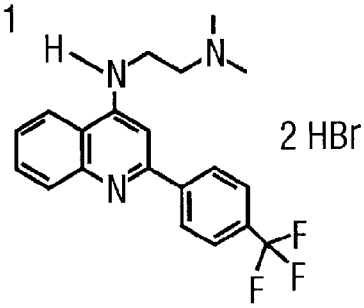
2 HBr
| 6.82 | NCl |
| 6.81 | Strekowski |
12
147 LJ-250
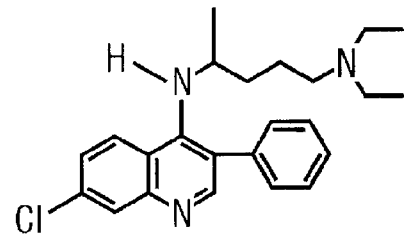
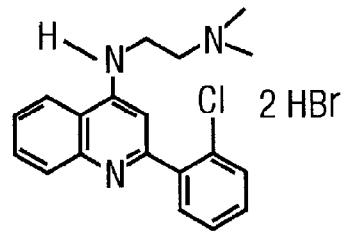
2 HBr
| 6.80 | NCl |
| 6.79 | Strekowski |
*FIG. 1N-2*

41

6.64 | NCI

31

6.62 | NCI

76

6.60 | NCI

11

6.56 | NCI

185 LJ-329

6.55 | Strekowski

73

6.54 | NCI

74

6.52 | NCI

62

6.51 | NCI

Scheme 3

MS-128

8.82

MS-96

9.00

MS-76

9.12

MS-98

8.84

MS-91-2

8.97

MS-12-1

8.84

MS-130

8.66

MS-95

8.72

MS-132

8.62

MHQ-92

8.49

MHQ-108

8.43

MS-77

8.27

MS-133

8.48

MS-129

8.31

MS-136

8.26

MS-140

8.26

MHQ-88

8.22

MHQ-71

8.17

MHQ-89

8.11

MS-125

8.17

MS-139

7.94

MHQ-93

8.15

MS-134

8.07

MHQ-86

8.22

MS-139

7.94

MHQ-94

8.04

MHQ-60

7.86

MS-91

7.84

MS-53

7.84

MS-96

7.81

MHO-111

7.81

MS-86

7.80

MS-127

7.80

MS-48

7.77

MS-101

7.76

ANTAGONISM OF IMMUNOSTIMULATORY CPG-OLIGONUCLEOTIDES BY 4-AMINOQUINOLINES AND OTHER WEAK BASES

The present application claims the benefit of U.S. Provisional Application Serial No. 60/139,544 filed on Jun. 16, 1999. The entire text of the above-referenced disclosure is herein incorporated by reference.

BACKGROUND OF THE INVENTION

1. Field of the Invention

The present invention relates generally to the field of immunology. More particularly, it concerns preventative and therapeutic compositions and methods that inhibit stimulation of the immune system.

2. Description of Related Art

While stimulation of the immune systems prevents and controls infection, it can have an adverse physiological effect, as is the case with autoimmune diseases and phenomena, with rejection of cells and tissues during adoptive immunotherapy and transplants, and with invasions by pathogens. Inhibition of this stimulation can have beneficial therapeutic results. However, new and more effective treatments to effect inhibition of immunostimulation are still needed.

Autoimmunity is generally caused by aberrations in lymphocyte activities. While the precise cause of autoimmunity is not known, it most likely involves a mechanistic failure in at least one of the steps of maintaining self-tolerance to the body's own antigens. Several factors are thought to play a part in the development of autoimmunity, including the host's genetic makeup. Autoimmune diseases afflict approximately 1% to 2% of the human population. Autoimmune phenomena, are the result of a disease, for example myocardial infarcation, that may cause damage to tissue, which consequently effects the release of immunogenic tissue antigens; this condition, unlike autoimmune disease, is unrelated to the pathogenesis of the disease that caused it.

There are a wide variety of autoimmune diseases. They are classified as either organ-specific based on the primary site of injury or systemic (see Table 1). There are three ways in which damage or injury to tissue is caused by autoimmune disease: cell-mediated immunity, cell lysis and autoantibody-induced release of inflammatory mediators, and immune complex disease.

Cell-mediated immunity occurs when sensitized T cells directly damage cells or release lymphokines that augment the inflammatory reaction. An association of an autoantibody with its antigen in intercellular fluid causes cell lysis and autoantibody-induced release of inflammatory mediators. This interaction results in release of inflammatory mediators, induction of the complement pathway, or activation of cytotoxic cells, which can trigger cell lysis. The third mechanism, immune complex disease, involves a reaction between circulating autoantibodies and antigens on the cell surface. This complex becomes deposited in tissue such as the joints, blood vessels, and glomeruli, causing complement to be fixed and subsequent inflammation and tissue damage.

Rejection of cells and tissue can involve rejection of the graft by the host. The body's own cells are identified as self because of a complex series of cell surface molecules known as major histocompatibility molecules (MHC). Rejection of cells and tissues can occur following transplantation of cells or organs or after adoptive immunotherapy has been implemented. In graft-versus host disease (GVHD), the grafted immune system attacks the host cells. One example in which GVHD becomes particularly significant is bone marrow transplantation (BMT), which is frequently used for the treatment of a variety of bone marrow-related disorders and in cancer therapy to replace bone marrow cells lost to chemotherapy and radiation treatment. In severe cases of GVHD, a patient's compromised immune system gives rise to many complications including those in the liver, causing jaundice, in the skin causing rash, and in the gastrointestinal tract, including diarrhea, anorexia, nausea and vomiting, malabsorption, abdominal pain ileus, and ascites formation.

Sepsis is the primary cause of death in the intensive care unit with more than 400,000 cases in the United States annually. It can be caused by infection by a pathogen, such as viruses, bacteria, fungi, and parasites, which triggers host defenses. This may result in activation of innate immunity, particularly, an inflammatory response, which consequently promotes deleterious effects (collectively termed "sepsis") including shock, respiratory distress, capillary leaks, renal failure, jaundice, bleeding, coma and death.

Despite this information, preventative and therapeutic treatment to inhibit stimulation of the immune system is still needed. Oligodeoxynucleotides (ODN), bacterial DNA, and phosphorothioate oligodeoxynucleotides with unmethylated CpG-motifs are immunostimulatory and may contribute to autoimmunity. Thus, they can serve as a model system to identify compounds and methods that effect inhibition of immunostimulation. Using CpG-ODN, a number of compounds have been identified as possessing this property. For example, a number of quinoline derivatives that are active against stimulation by CpG-ODN have been shown to induce remission of rheumatoid arthritis and lupus erythematosus (Fox, 1993; Wallace, 1994). Chloroquine and a number of structural analogs specifically and powerfully inhibit this effect at nanomolar concentration. Therefore, inhibition of CpG-ODN immunostimulation can be effected generally in the treatment of autoimmune diseases and phenomena, sepsis, and transplantation rejection, including graft-versus-host disease.

SUMMARY OF THE INVENTION

The inhibition of immune stimulation in cases such as autoimmune diseases, tissue transplantation and the like would be therapeutically beneficial. Currently, methods to inhibit stimulation of the immune system are limited. Therefore, it is a goal of the present invention to provide methods and compositions for inhibiting immunostimulation in a subject.

In one embodiment of the invention, a method of inhibiting immunostimulation in a subject by administering an effective amount of a substituted 4-quinolinamine composition to the subject comprising a compound having the structural formula A is provided.

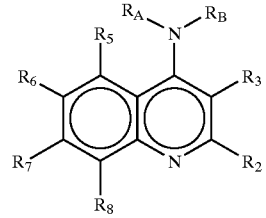

(A)

A substituted 4-quinolinamine composition of formula A, comprises groups $R_A$, $R_B$, $R_2$, $R_3$, $R_5$, $R_6$, $R_7$ and R8, wherein $R_A$ is hydrogen atom or a lower alkyl group, $R_B$ is a substituted or unsubstituted alkyl, alkenyl or alkynyl secondary or tertiary amine, $R_2$ is a substituted or unsubstituted phenyl group, a substituted or unsubstituted naphthyl group, an substituted or unsubstituted anthracyl group, a substituted or unsubstituted phenanthryl group or a substituted or unsubstituted styryl group, $R_3$ is a hydrogen atom, $R_5$ is a hydrogen atom, $R_6$ is a hydrogen atom or a halogen atom, $R_7$ is a hydrogen atom or a halogen atom, $R_8$ is a hydrogen atom and pharmaceutically acceptable salts thereof. In preferred embodiments, the $R_2$ phenyl, naphthyl, anthracyl, styryl or phenanthryl group substitution further comprise one or more substitutions selected from the group consisting of an alkyl group, an alkoxy group, an alkoxyalkyl group, an ester group, an alkylamino group, a dialkylamino group, a cyclic amino group, a halogen atom, and any combination thereof. In some aspects of the invention, the $R_2$ substitution is an N-substituted aminomethyl group, a cyclic aminomethyl group, or an aminomethyl group, additionally substituted at the nitrogen atom with a cyclic aminoalkyl group. In particularly preferred embodiments, a cyclic amino group is a piperazino group, a piperidino group, a pyrrolidino group, an imidazolyl group, a pyridyl, or a morpholino group. In another embodiment, the $R_B$ substituted alkyl is selected from the group consisting of a cyclic amino group, furyl, thienyl, phenyl, alkylamino group, dialkylamino group, and any combination thereof. It is contemplated that phenyl includes a substituted phenyl. In preferred embodiments, a cyclic amino group is a piperazino group, a piperidino group, a pyrrolidino group, an imidazolyl group, a pyridyl group, or a morpholino group. The cyclic amino groups in $R_B$ or $R_2$ may be further substituted with an alkyl group, for example, an N-methylpiperazino or an N-pyrrolidinoalkyl. It is further contemplated that there is a covalent bond formed between $R_A$ and $R_B$, for example, to form an N-methylpiperazino.

In another embodiment, the present invention provides a method of inhibiting immunostimulation in a subject comprising administering an effective amount of a substituted 4-quinolinamine composition to said subject comprising a compound having the structural formula B.

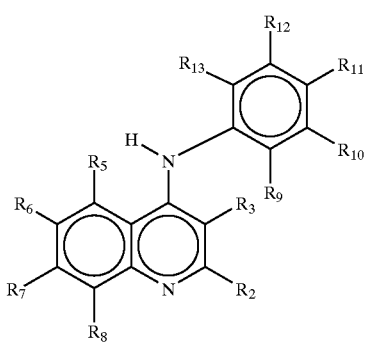

(B)

A substituted 4-quinolinamine composition of formula B, comprises a phenyl group, $R_2$, $R_3$, $R_5$, $R_6$, $R_7$ and $R_8$, wherein $R_2$ is a substituted or unsubstituted phenyl group, a substituted or unsubstituted naphthyl group, a substituted or unsubstituted anthracyl group, a substituted or unsubstituted styryl group or a substituted or unsubstituted phenanthryl group, $R_3$ is a hydrogen atom, $R_5$ is a hydrogen atom, $R_6$ is a hydrogen atom or a halogen atom, $R_7$ is a hydrogen atom, a halogen atom or an alkyl halogen atom, $R_8$ is a hydrogen atom and pharmaceutically acceptable salts thereof. In a preferred embodiment, when the $R_2$ phenyl, naphthyl, anthracyl, styryl or phenanthryl group comprises substitutions, these are defined as one or more substitutions selected from the group consisting of an alkyl group, an alkoxy group, an alkoxyalkyl group, an ester group, an alkylamino group, an dialkylamino group, a cyclic amino group, a halogen atom or any combination thereof. In particularly preferred embodiments, a cyclic amino group is a piperazino group, a piperidino group, a pyrrolidino group, an imidazolino group or a morpholino group.

The phenyl group additionally may be substituted at positions $R_9$, $R_{10}$, $R_{11}$, $R_{12}$ and $R_{13}$, wherein the substituted phenyl group comprises one or more substitutions selected from the group consisting of an alkyl group, an alkoxy group, an alkoxyalkyl group, an ester group, an alkylamino group, an dialkylamino group, a cyclic amino group, a furan group, a thiophene group, a halogen atom or any combination thereof. In preferred embodiments, a cyclic amino group is a piperazino group, a piperidino group, a pyrrolidino group, an imidazolino group or a morpholino group.

In further embodiments of the invention, a method of inhibiting immunostimulation in a subject comprises administering an effective amount of a substituted 4-quinolinamine composition to the subject comprising a compound having the structural formula C.

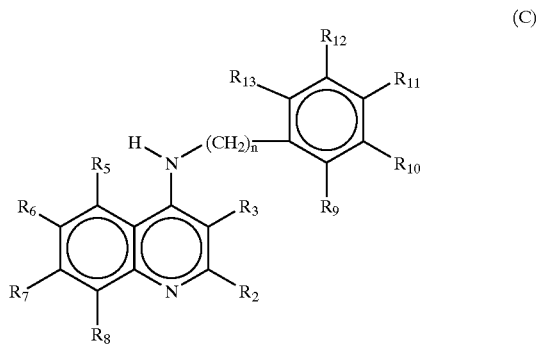

(C)

A substituted 4-quinolinamine composition of formula C, comprises a phenyl group spatially distanced form the quinolinamine by an alkyl group of 0 to 4 $CH_2$ molecules, $R_2$, $R_3$, $R_5$, $R_6$, $R_7$ and $R_8$, wherein $R_2$ is a substituted or unsubstituted phenyl group, a substituted or unsubstituted naphthyl group, a substituted or unsubstituted anthracyl group, a substituted or unsubstituted styryl group or a substituted or unsubstituted phenanthryl group, $R_3$ is a hydrogen atom, $R_5$ is a hydrogen atom, $R_6$ is a hydrogen atom or a halogen atom, $R_7$ is a hydrogen atom, a halogen atom or an alkyl halogen atom, $R_8$ is a hydrogen atom and pharmaceutically acceptable salts thereof. In se preferred embodiments, the $R_2$ phenyl, naphthyl, anthracyl, styryl or phenanthryl group substitution comprises one or more substitutions selected from the group consisting of an alkyl group, an alkoxy group, an alkoxyalkyl group, an ester group, an alkylamino group, an dialkylamino group, a cyclic amino group, a halogen atom or any combination thereof. In particularly preferred embodiments, a cyclic amino group is a piperazino group, a piperidino group, a pyrrolidino group, an imidazolino group or a morpholino group.

In other embodiments of the invention, the phenyl group additionally may be substituted at positions $R_9$, $R_{10}$, $R_{11}$, $R_{12}$ and $R_{13}$, wherein the substituted phenyl group comprises one or more substitutions selected from the group consisting of an alkyl group, an alkoxy group, an alkoxyalkyl group, an ester group, an alkylamino group, a dialkylamino group, a cyclic amino group, a furan group, a thiophene group, a halogen atom, or any combination thereof.

In another embodiment, a method of inhibiting immunostimulation in a subject comprises administering an effective amount of a substituted bis-4-quinolinamine composition to the subject comprising a compound having the structural formula D.

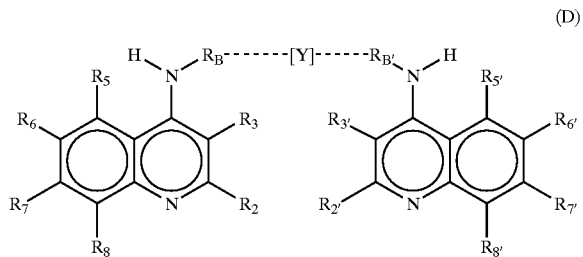

(D)

A substituted bis-4-quinolinamine composition having the structural formula D, comprises $R_B$ on the first 4-quinolinamine covalently attached to $R_{B'}$ on the second 4-quinolinamine by linker group Y, $R_2$ is a substituted or unsubstituted phenyl group, a substituted or unsubstituted naphthyl group, a substituted or unsubstituted anthracyl up, a substituted or unsubstituted styryl group or a substituted or unsubstituted phenanthryl group, $R_3$ is a hydrogen atom, $R_5$ is a hydrogen atom, $R_6$ is a hydrogen atom or a halogen atom, $R_7$ is a hydrogen atom or a halogen atom, $R_8$ is a hydrogen atom, $R_{2'}$ is a substituted or unsubstituted phenyl group, a substituted or unsubstituted naphthyl group, an substituted or unsubstituted anthracyl group, a substituted or unsubstituted styryl group or a substituted or unsubstituted phenanthryl group, $R_{3'}$ is a hydrogen atom, $R_{5'}$ is a hydrogen atom, $R_{6'}$ is a hydrogen atom or a halogen atom, $R_{7'}$ is a hydrogen atom or a halogen atom, $R_{8'}$ is a hydrogen atom and pharmaceutically acceptable salts thereof. In other embodiments, the $R_2$ phenyl, naphthyl, anthracyl, styryl or phenanthryl group substitution is further defined as one or more substitutions selected from the group consisting of an alkyl group, an alkoxy group, an alkoxyalkyl group, an ester group, an alkylamino group, an dialkylamino group, a cyclic amino group, a halogen atom or any combination thereof and the $R_{2'}$ phenyl, naphthyl, anthracyl, styryl or phenanthryl group substitution is further defined as one or more substitutions selected from the group consisting of an alkyl group, an alkoxy group, an alkoxyalkyl group, an ester group, an alkylamino group, an dialkylamino group, a cyclic amino group, a halogen atom or any combination thereof.

In preferred embodiments, a cyclic amino group is a piperazino group, a piperidino group, a pyrrolidino group, an imidazolino group or a morpholino group. In particular embodiments, the linker group Y is an alkyl group, an ester group, an alkoxyalkyl group, an alkylamino group, an dialkylamino group, amido group, a cyclohexane, an piperazino group or any combination thereof.

In other embodiments of the present invention, a method of inhibiting immunostimulation in a subject comprising administering an effective amount of a substituted bis-9-aminoacridine composition to the subject, comprising a compound

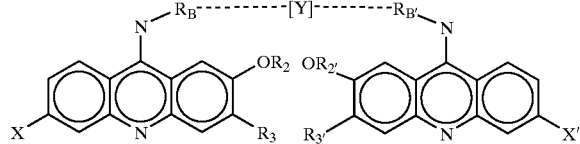

having the structural formula E, is provided.

A substituted bis-9-aminoacridine of formula E, comprises $R_B$ on the first 9-aminoacridine covalently attached to $R_{B'}$ on the second 9-aminoacridine by linker group Y. A substituted bis-9-aminoacridine of formula E further comprises $OR_2$, $OR_{2'}$, $R_3$, $R_{3'}$, X and X', wherein $OR_2$ is a lower alkyl group, $OR_{2'}$ is a lower alkyl group, $R_3$ is a hydrogen atom or a lower alkoxy group, $R_{3'}$ is a hydrogen atom or a lower alkoxy group, X is a halogen atom, X' is a halogen atom and pharmaceutically acceptable salts thereof. In other embodiments, the linker group Y is an alkyl group, an ester group, an alkoxyalkyl group, an alkylamino group, an dialkylamino group, amido group, a cyclohexane, an piperazino group or any combination thereof.

In yet another embodiment, a method of inhibiting immunostimulation in a subject comprises administering an effective amount of a composition to a subject comprising a compound having the structural formula F, wherein a 4-quinolinamine at position $R_B$ is covalently linked to a 9-aminoacridine at position $R_{B'}$ by linker group Y.

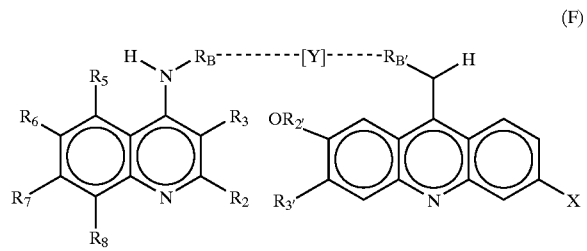

(F)

The 4-quinolinamine, 9-aminoacridine composition of formula F comprises $R_A$, $R_B$, $R_2$, $R_3$, $R_5$, $R_6$, $R_7$, $R_8$, $R_{B'}$, $OR_{2'}$, $R_{3'}$ and X, wherein $R_A$ is atom or a lower alkyl group, $R_2$ is a substituted or unsubstituted phenyl group, a substituted or unsubstituted naphthyl group, an substituted or unsubstituted anthracyl group, a substituted or unsubstituted styryl group or a substituted or unsubstituted phenanthryl group, $R_3$ is a hydrogen atom, $R_5$ is a hydrogen atom, $R_6$ is a hydrogen atom or a halogen atom, $R_7$ is a hydrogen atom or a halogen atom, $R_8$ is a hydrogen atom, $OR_{2'}$ is a lower alkyl group, $R_{3'}$ is a hydrogen atom, or a lower alkoxy group, X is a halogen atom and pharmaceutically acceptable salts thereof. In certain embodiments, the $R_2$ phenyl, naphthyl, anthracyl, styryl or phenanthryl group substitution is further defined as one or more substitutions selected from the group consisting of an alkyl group, an alkoxy group, an alkoxyalkyl group, an ester group, an alkylamino group, an dialkylamino group, a cyclic amino group, a halogen atom or any combination thereof. In preferred embodiments, a cyclic amino group is a piperazino group, a piperidino group, a pyrrolidino group, an imidazolino group or a morpholino group. In other embodiments, the Y linker is an alkyl group, an ester group, an alkoxyalkyl group, an alkylamino group, an dialkylamino group, amido group, a cyclohexane, an piperazino group or any combination thereof.

In other embodiments of the present invention, 4-quinolinamine and 9-aminoacridine compositions are provided. Thus, in one embodiment, a substituted 4-quinolinamine composition having the structural formula A is provided.

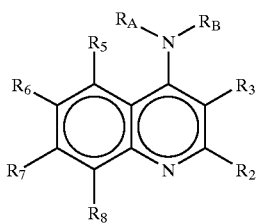

(A)

$R_A$ is hydrogen atom or a lower alkyl group, $R_B$ is a substituted or unsubstituted alkyl, alkenyl or alkynyl secondary or tertiary amine, $R_2$ is a substituted or unsubstituted phenyl group, a substituted or unsubstituted naphthyl group, an substituted or unsubstituted anthracyl group, a substituted or unsubstituted phenanthryl group or a substituted or unsubstituted styryl group, $R_3$ is a hydrogen atom, $R_5$ is a hydrogen atom, $R_6$ is a hydrogen atom or a halogen atom, $R_7$ is a hydrogen atom or a halogen atom, $R_8$ is a hydrogen atom and pharmaceutically acceptable salts thereof. In particular embodiments, the $R_2$ phenyl, naphthyl, anthracyl, styryl or phenanthryl group substitution is further defined as one or more substitutions selected from the group consisting of an alkyl group, an alkoxy group, an alkoxyalkyl group, an ester group, an alkylamino group, a dialkylamino group, a cyclic amino group, a halogen atom and any combination thereof. In preferred embodiments the cyclic amino group is a piperazino group, a piperidino group, a pyrrolidino group, a imidazolino group or a morpholino group. In yet other embodiments, the $R_B$ alkyl substitution is selected from the group consisting of a cyclic amino group, furan and thiophene, wherein the cyclic amino group is a piperazino group, a piperidino group, a pyrrolidino group, an imidazolino group or a morpholino group.

In other embodiments of the present invention a substituted 4-quinolinamine composition is provided having the structural formula B.

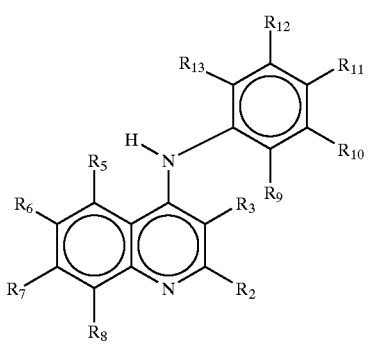

(B)

The phenyl group can be substituted at $R_9$, $R_{10}$, $R_{11}$, $R_{12}$ and $R_{13}$, wherein a substituted phenyl group comprises one or more substitutions selected from the group consisting of an alkyl group, an alkylaminoalkyl group, an alkoxy group, an alkoxyalkyl group, an ester group, an alkylamino group, an dialkylamino group, a cyclic amino group, a furan group, a thiophene group, a halogen atom or any combination thereof. $R_2$ is a substituted or unsubstituted phenyl group, a substituted or unsubstituted naphthyl group, a substituted or unsubstituted anthracyl group, a substituted or unsubstituted styryl group or a substituted or unsubstituted phenanthryl group, $R_3$ is a hydrogen atom, $R_5$ is a hydrogen atom, $R_6$ is a hydrogen atom or a halogen atom, $R_7$ is a hydrogen atom, a halogen atom or an alkyl halogen atom, $R_8$ is a hydrogen atom and pharmaceutically acceptable salts thereof. In other embodiments, a cyclic amino group is a piperazino group, a piperidino group, a pyrrolidino group, an imidazolino group or a morpholino group.

In yet other embodiments, the $R_2$ phenyl, naphthyl, anthracyl, styryl or phenanthryl group substitution is further defined as one or more substitutions selected from the group consisting of an alkyl group, an alkoxy group, a hydroxy group, an alkoxyalkyl group, an ester group, an alkylamino group, an dialkylamino group, a cyclic amino group, a halogen atom or any combination thereof. In certain embodiments, a cyclic amino group is a piperazino group, a piperidino group, a pyrrolidino group, an imidazolino group or a morpholino group.

In particular embodiments, a substituted 4-quinolinamine composition having the structural formula C is provided.

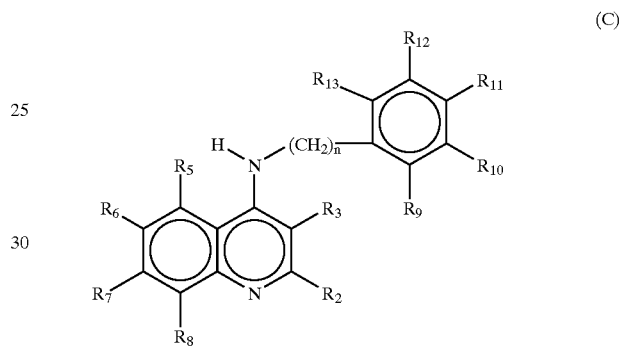

(C)

The phenyl group can be unsubstituted or substituted at $R_9$, $R_{10}$, $R_{11}$, $R_{12}$ and $R_{13}$, wherein the substituted phenyl group is distanced spatially from the quinolinamine by an alkyl group of 0 to 4 $CH_2$ and comprises one or more substitutions selected from the group consisting of an alkyl group, an alkoxy group, an alkoxyalkyl group, an ester group, an alkylamino group, an dialkylamino group, a cyclic amino group, a furan group, a thiophene group, a halogen atom, or any combination thereof. $R_2$ is a substituted or unsubstituted phenyl group, a substituted or unsubstituted naphthyl group, a substituted or unsubstituted anthracyl group, a substituted or unsubstituted styryl group or a substituted or unsubstituted phenanthryl group, $R_3$ is a hydrogen atom, $R_5$ is a hydrogen atom, $R_6$ is a hydrogen atom or a halogen atom, $R_7$ is a hydrogen atom, a halogen atom or an alkyl halogen atom, $R_8$ is a hydrogen atom and pharmaceutically acceptable salts thereof. In certain embodiments, a cyclic amino group is a piperazino group, a piperidino group, a pyrrolidino group, an imidazolino group or a morpholino group.

In other embodiments, the $R_2$ phenyl, naphthyl, anthracyl, styryl or phenanthryl group substitution is further defined as one or more substitutions selected from the group consisting of an alkyl group, an alkoxy group, an alkoxyalkyl group, an ester group, an alkylamino group, an dialkylamino group, a cyclic amino group, a halogen atom or any combination thereof. In yet other embodiments, a cyclic amino group is a piperazino group, a piperidino group, a pyrrolidino group, an imidazolino group or a morpholino group.

In another embodiment of the invention, a substituted bis-4-quinolinamine composition having the structural formula D is provided.

(D)

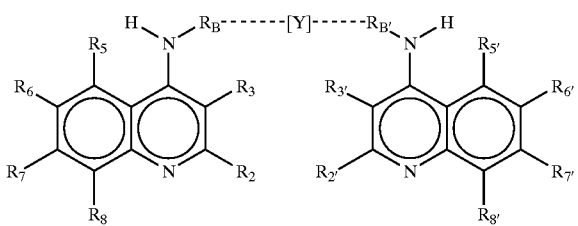

The $R_B$ on the first 4-quinolinamine is covalently attached to $R_{B'}$ on the second 4-quinolinamine by linker group Y, wherein linker Y is an alkyl group, an ester group, an alkoxyalkyl group, an alkylaminoalkyl group, an alkylamino group, an dialkylamino group, amido group, a cyclohexane, an piperazino group or any combination thereof. $R_2$ is a substituted or unsubstituted phenyl group, a substituted or unsubstituted naphthyl group, a substituted or unsubstituted anthracyl group, a substituted or unsubstituted styryl group or a substituted or unsubstituted phenanthryl group, $R_3$ is a hydrogen atom, $R_5$ is a hydrogen atom, $R_6$ is a hydrogen atom or a halogen atom, $R_7$ is a hydrogen atom or a halogen atom, $R_8$ is a hydrogen atom, $R_{2'}$ is a substituted or unsubstituted phenyl group, a substituted or unsubstituted naphthyl group, an substituted or unsubstituted anthracyl group, a substituted or unsubstituted styryl group or a substituted or unsubstituted phenanthryl group, $R_{3'}$ is a hydrogen atom, $R_{5'}$ is a hydrogen atom, $R_{6'}$ is a hydrogen atom or a halogen atom, $R_{7'}$ is a hydrogen atom or a halogen atom, $R_{8'}$ is a hydrogen atom and pharmaceutically acceptable salts thereof.

In certain embodiments, the $R_2$ phenyl, naphthyl, anthracyl, styryl or phenanthryl group substitution is further defined as one or more substitutions selected from the group consisting of an alkyl group, an alkoxy group, an alkoxyalkyl group, a hydroxy group, an ester group, an alkylamino group, an dialkylamino group, a cyclic amino group, a halogen atom or any combination thereof. In preferred embodiments, a cyclic amino group is a piperazino group, a piperidino group, a pyrrolidino group, an imidazolino group or a morpholino group. In other embodiments, the $R_{2'}$ phenyl, naphthyl, anthracyl, styryl or phenanthryl group substitution is further defined as one or more substitutions selected from the group consisting of an alkyl group, an alkoxy group, a hydroxy group, an alkoxyalkyl group, an ester group, an alkylamino group, an dialkylamino group, a cyclic amino group, a halogen atom or any combination thereof. In particular embodiments, a cyclic amino group is a piperazino group, a piperidino group, a pyrrolidino group, an imidazolino group or a morpholino group.

In certain embodiments, a substituted bis-9-aminoacridine composition having the structural formula E is provided.

(E)

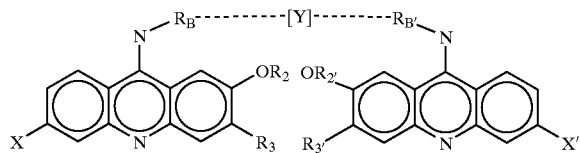

The $R_B$ on the first 9-aminoacridine is covalently attached to $R_{B'}$ on the second 9-aminoacridine by linker group Y, wherein linker Y is an alkyl group, an ester group, an ether group, an alkylamino group, an dialkylamino group, amido group, a cyclohexane, an piperazino group or any combination thereof. $OR_2$ is a lower alkyl group, $OR_{2'}$ is a lower alkyl group, $R_3$ is a hydrogen atom or a lower alkoxy group, $R_{3'}$ is a hydrogen atom or a lower alkoxy group, X is a halogen atom, X' is a halogen atom and pharmaceutically acceptable salts thereof.

In another embodiment, 4-quinoliamine, 9-aminoacridine composition having the structural formula F is provided.

(F)

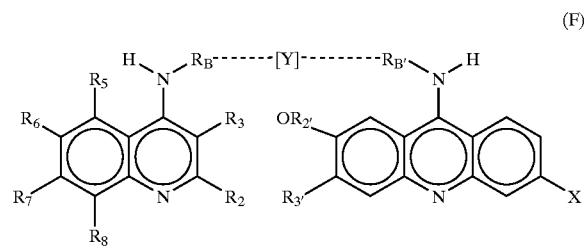

The $R_B$ position on the 4-quinoliamine is covalently attached to the $R_{B'}$ position of the 9-aminoacridine by linker Y, wherein linker Y is an alkyl group, an ester group, an alkoxyalkyl group, an alkylamino group, amido group, a cyclohexanedieyl, an piperazino group or any combination thereof. $R_A$ is hydrogen atom or a lower alkyl group, $R_2$ is a substituted or unsubstituted phenyl group, a substituted or unsubstituted naphthyl group, an substituted or unsubstituted anthracyl group, a substituted or unsubstituted styryl group or a substituted or unsubstituted phenanthryl group, $R_3$ is a hydrogen atom, $R_5$ is a hydrogen atom, $R_6$ is a hydrogen atom or a halogen atom, $R_7$ is a hydrogen atom or a halogen atom, $R_8$ is a hydrogen atom, $OR_2'$ is a lower alkyl group, $R_3'$ is a hydrogen atom, or a lower alkoxy group, X is a halogen atom and pharmaceutically acceptable salts thereof.

In particular embodiments, the $R_2$ phenyl, naphthyl, anthracyl, styryl or phenanthryl group substitution is further defined as one or more substitutions selected from the group consisting of an alkyl group, an alkoxy group, an alkoxyalkyl group, an ester group, an alkylamino group, an dialkylamino group, a cyclic amino group, a halogen atom or any combination thereof. In certain embodiments, a cyclic amino group is a piperazino group, a piperidino group, a pyrrolidino group, an imidazolino group or a morpholino group.

It is also contemplated in the present invention that various other substitutions, such as hydroxy groups and various substituted alkyl groups can be made at the $R_B$ and $R_2$ positions of the substituted 4-quinoliamine.

The term "lower alkyl" in the context of the present invention represents straight and branched alkyl groups up to 7 carbon atoms. As used herein the specification, "a" or "an" may mean one or more. As used herein in the claim(s), when used in conjunction with the word "comprising," the words "a" or "an" may mean one or more than one. As used herein "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1D:
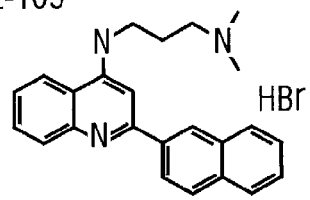
FIGS. 1A.–1P. Various analogs with some inhibitory activity against CpG ODN immunostimulation.
Figure 1D:
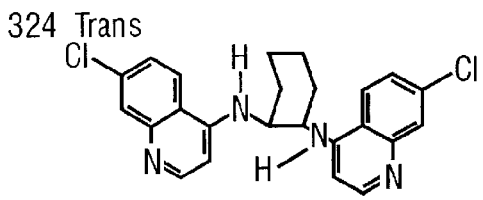
Figure 1D:
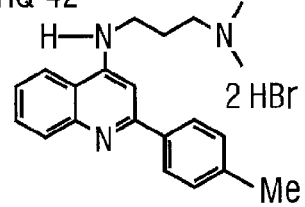
Figure 1D:
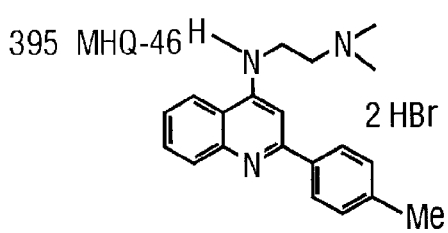
Figure 1D:
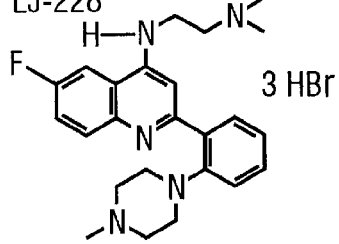
Figure 1D:
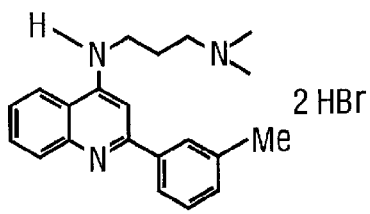
Figure 1D:
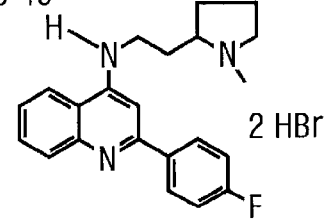
Figure 1D:
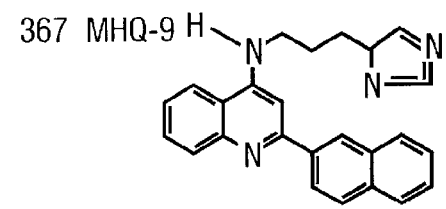
Figure 1D:
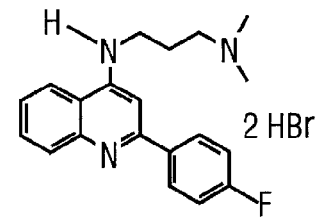
Figure 1D:
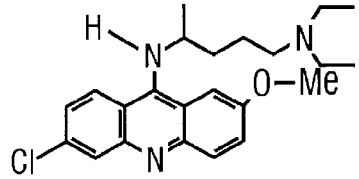
Figure 1E:
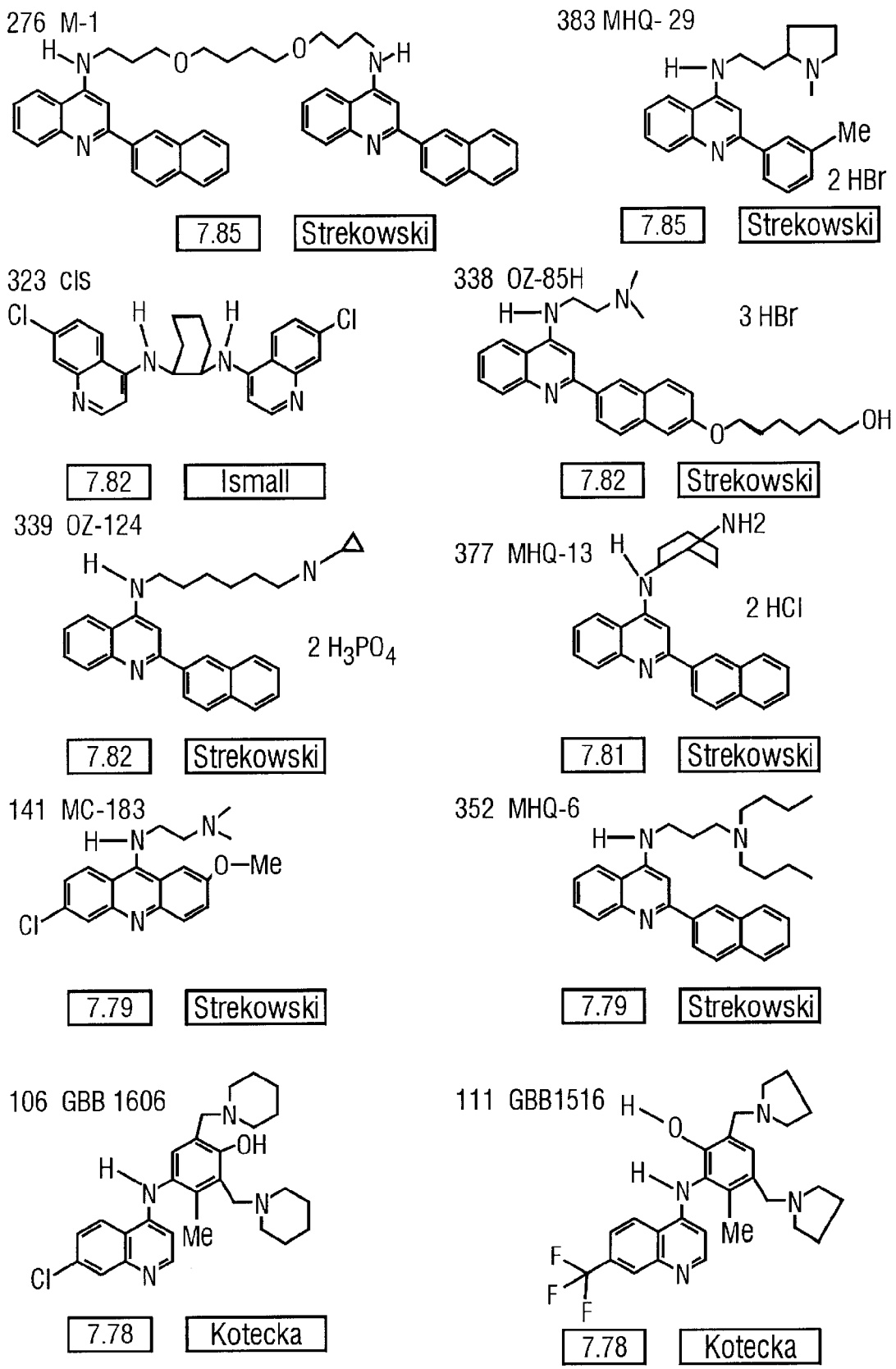
Figure 1J:
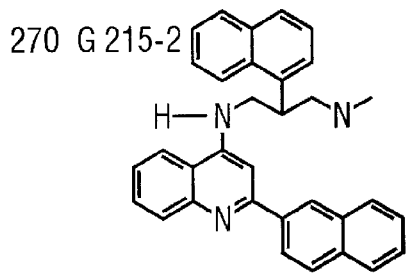
Figure 1J:
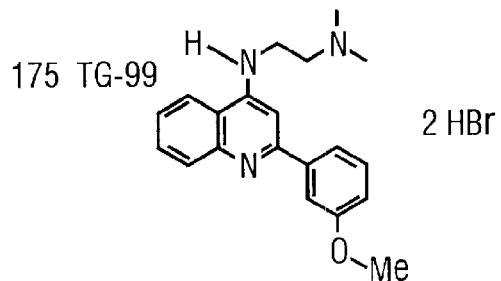
Figure 1J:
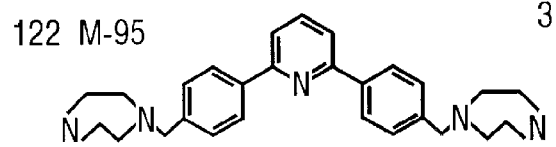
Figure 1J:
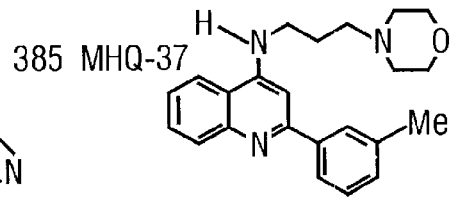
Figure 1J:
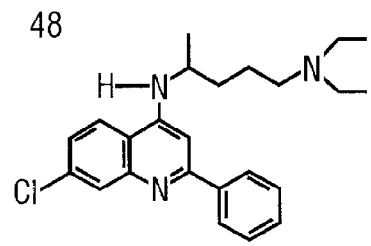
Figure 1J:
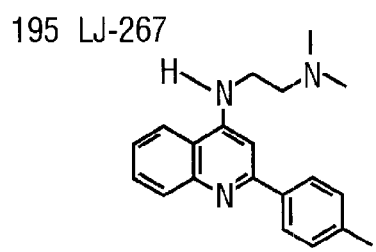
Figure 1J:
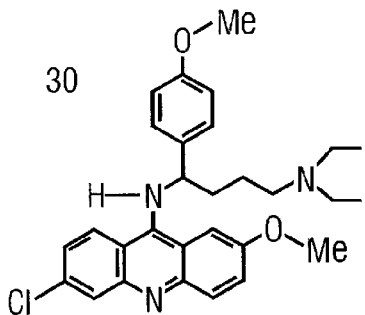
Figure 1J:
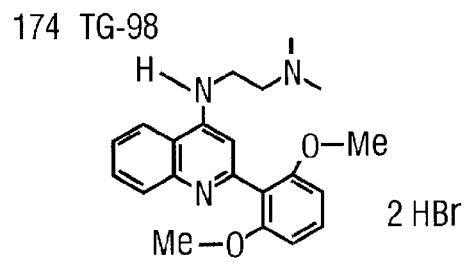
Figure 1J:
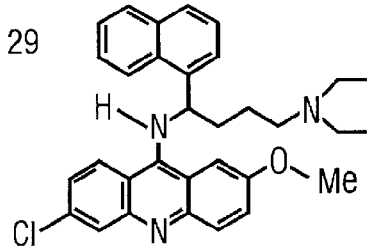
Figure 1J:
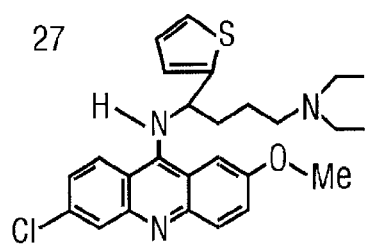
Figure 1K:
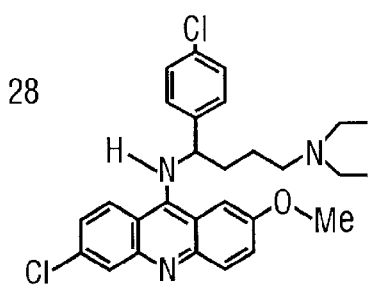
Figure 1K:
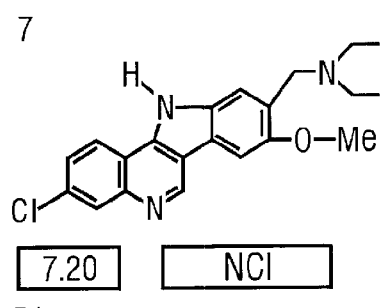
Figure 1K:
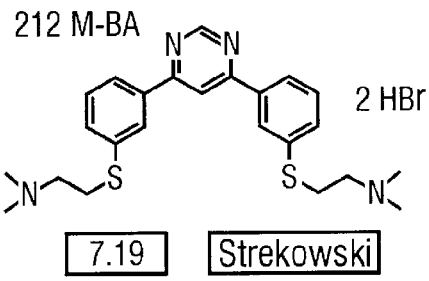
Figure 1K:
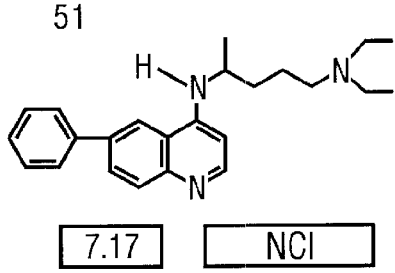
Figure 1K:
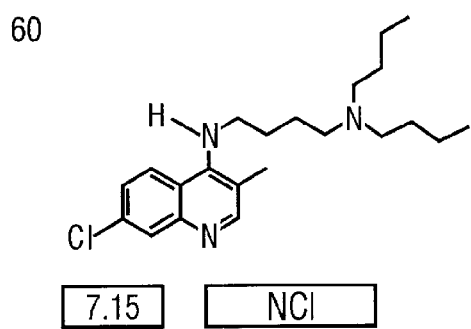
Figure 1K:
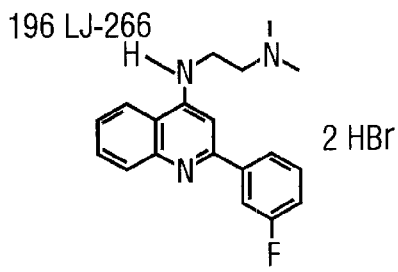
Figure 1K:
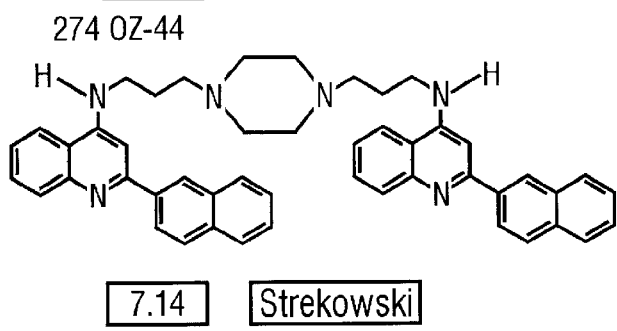
Figure 1K:
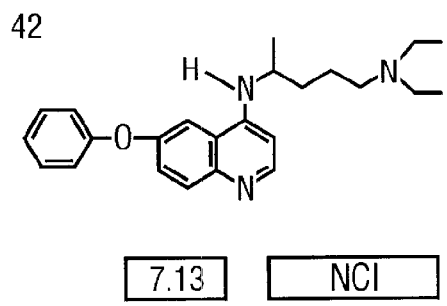
Figure 1K:
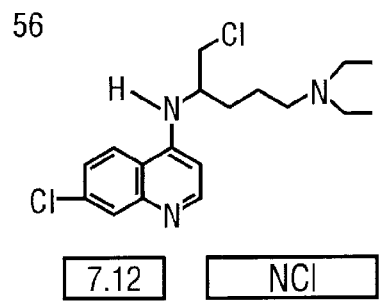
Figure 1K:
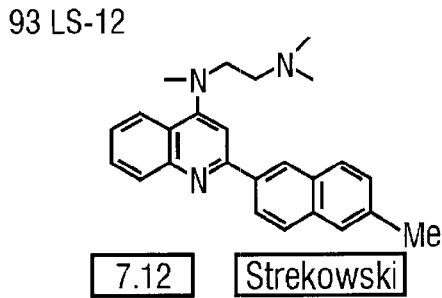
Figure 1M:
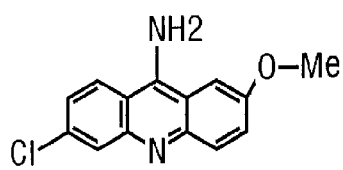
Figure 1M:
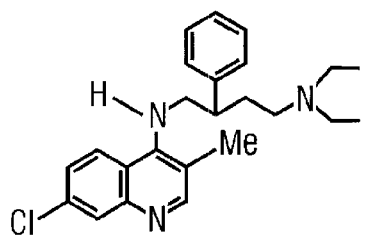
Figure 1M:
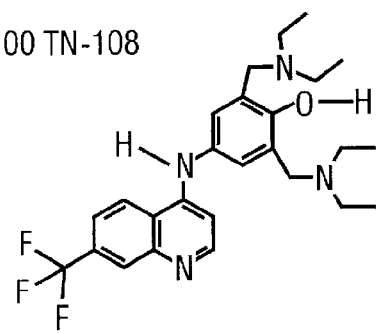
Figure 1M:
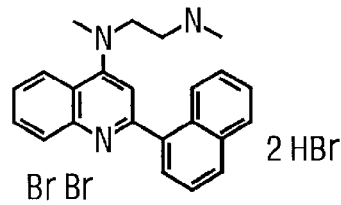
Figure 1M:
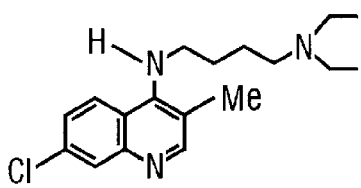
Figure 1M:
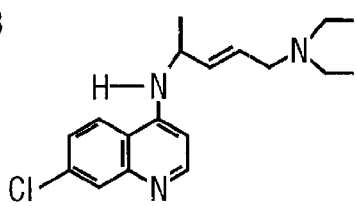
Figure 1M:
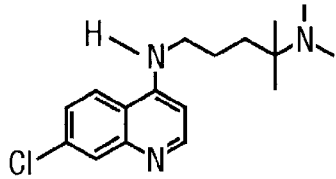
Figure 1M:
Figure 1M:
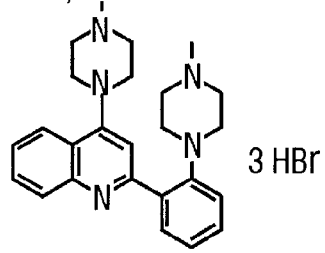
Figure 1M:
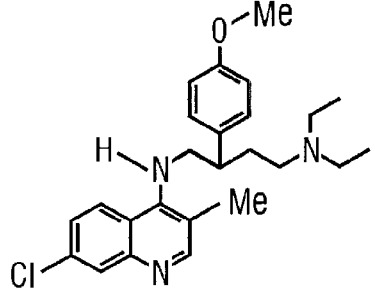
Figure 10:
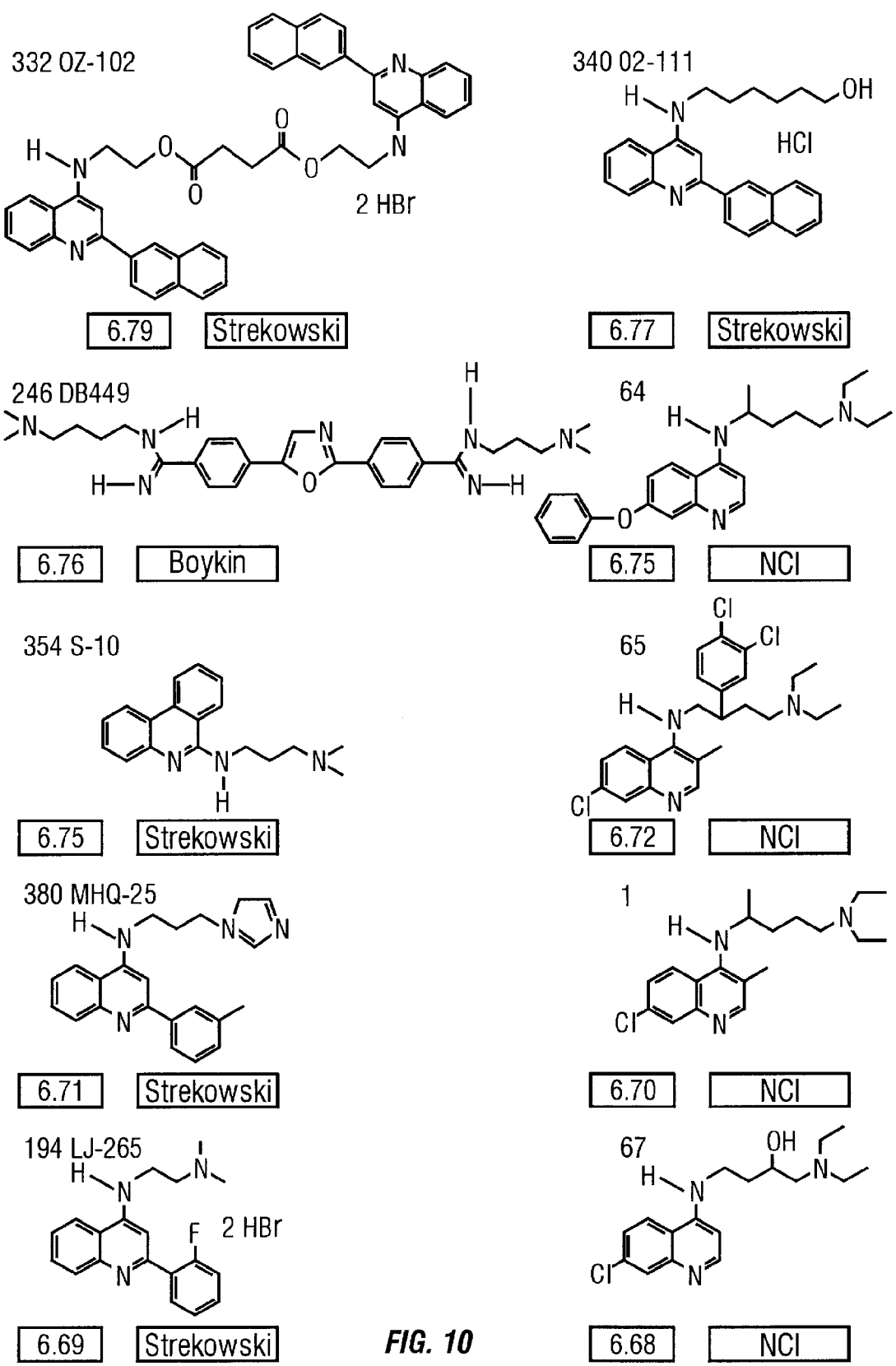
FIG. 10A. Scheme 2 as described in Example 9.
FIG. 10B. Scheme 3 as described in Example 9.
Figure 1P:
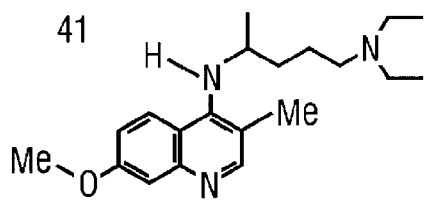
Figure 1P:
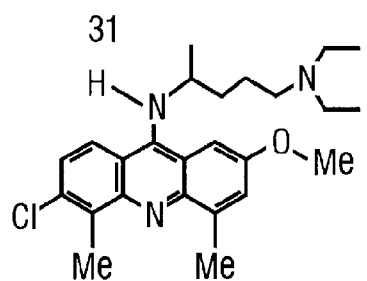
Figure 1P:
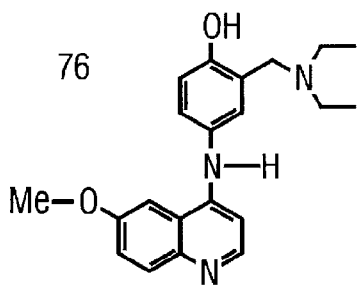
Figure 1P:
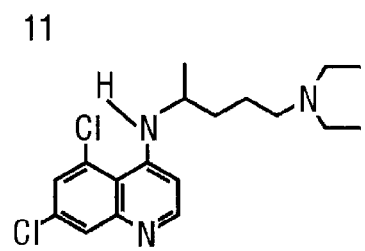
Figure 1P:
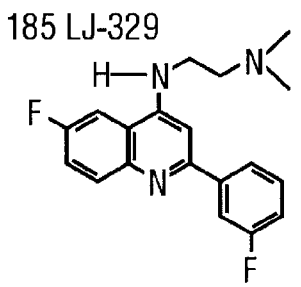
Figure 1P:
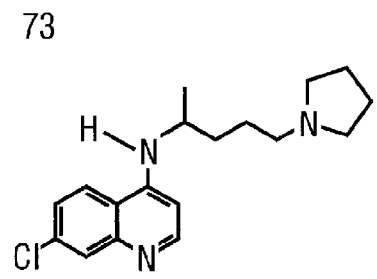
Figure 1P:
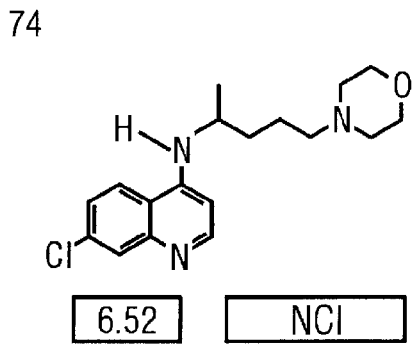
Figure 1P:
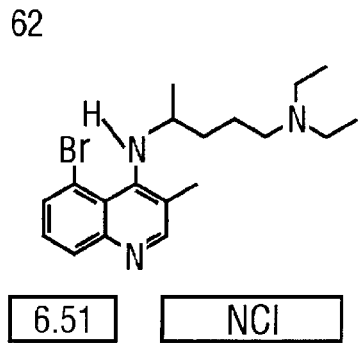

The present invention is directed to therapeutic compositions and methods for inhibiting stimulation of the immune system using chloroquine, its structural analogs and derivatives, or other weak bases. These compounds and methods have application in the treatment of the following: autoimmune diseases and phenomena, transplantation rejection responses, sepsis, and other disorders affecting the immune system.

I. Treatment Uses

A. Autoimmune Diseases and Phenomena

There are numerous conditions that qualify as an autoimmune disease. They occur either when the immune system malfunctions and the lymphocytes become sensitized against self tissue cells or when self tissue cells exhibit non-self characteristics such as expression of different antigens. Some of the most common disorders are listed in Table 1, such as rheumatoid arthritis and lupus erythrematosus. Other autoimmune diseases include: Alopecia Areata, Acquired Hemophilia, Ankylosing Spondylitis, Antiphospholipid Syndrome, Autoimmune Hepatitis, Autoimmune Hemolytic Anemia, Behcet's Disease, Cardiomyopathy, Celiac Sprue Dermatitis, Chronic Fatigue Immune Dysfunction Syndrome (CFIDS), Chronic Inflammatory Demyelinating Polyneuropathy, Churg-Strauss Syndrome, Cicatricial Pemphigoid, CREST Syndrome, Cold Agglutinin Disease, Discoid Lupus, Essential Mixed Cryoglobulinemia, Fibromyalgia, Fibromyositis, Guillain-Barre, Idiopathic Pulmonary Fibrosis, Idiopathic Thrombocytopenic Purpura, IgA Nephropathy, Juvenile Arthritis, Lichen Planus, Multiple Sclerosis, Myasthenia Gravis, Polyarteritis Nodosa, Polychondritis, Polyglandular Syndromes, Dermatomyositis, Primary Agammaglobulinemia, Primary Biliary Cirrhosis, Psoriasis, Raynaud's Phenomena, Reiter's Syndrome, Sarcoidosis, Stiff-Man Syndrome, Takayasu Arthritis, Temporal Arteritis/Giant Cell Arteritis, Ulcerative Colitis, Uveitis, Vasculitis, and Vitiligo.

TABLE 1

Selected Autoimmune Diseases and the Targets of Their Antibodies

| | Target of Antibody |
|---|---|
| Systemic (Non-Organ-Specific) Diseases | |
| Goodpasture's Syndrome | Basement membranes |
| Mixed Connective Tissue Disease | Nuclear ribonucleoproteins |
| Polymyositis | Nuclei, Jo-1, PL-7, histadyl-tRNA synthetase, threonyl-tRNA synthetase, PM-1, Mi-2 |
| Rheumatic Fever | Myocardium, heart valves, choroid plexus |
| Rheumatoid Arthritis | γ-Globulin, Epstein-Barr virus-related antigens, types II and III collagen |
| Scleroderma | Nuclei, Scl-70, SS-A (Ro), SS-B (La), centromere |

TABLE 1-continued

Selected Autoimmune Diseases and the Targets of Their Antibodies

| | Target of Antibody |
|---|---|
| Sjögren's Syndrome | γ-Globulin, SS-A (Ro), SS-B (La) |
| Systemic Lupus Erythematosus | DNA, ribonucleoproteins, histones, nuclear antigens |
| Wegener's granulomatosis | Neutrophils |
| Organ-Specific Diseases | |
| Addison's Disease | Adrenal cells |
| Allergic Rhinitis, Asthma, and autoimmune abnormalities | $\beta_2$-adrenergic receptors |
| Autoimmune hemolytic anemia | Erythrocytes |
| Acquired Hemophilia | Clotting Factor VIII |
| Bullous Pemphigoid | Basement membrane zone of skin and mucosa |
| Chronic Active Hepatitis | Nuclei of hepatocytes |
| Crohn's Disease | Lymphocytes, plasma cells, eosinophils |
| Glomemlonephritis | Glomeruli |
| Graves' Disease | Thyroid-stimulating hormone (TSH) receptor |
| Hashimoto's Thyroiditis | Thyroglobulin, TSH receptor |
| Idiopathic Hypoparathyroidism | Parathyroid cells |
| Idiopathic Neutropenia | Neutrophils |
| Idiopathic Thrombocytopenic Purpura | Platelets |
| Insulin-resistant Diabetes with acanthosis nigricans | Insulin receptor |
| Insulin-resistant Diabetes with ataxia-telangiectasia | Insulin receptor |
| Juvenile Insulin-dependent Diabetes | Pancreatic islet cells |
| Ménière's Disease | Type II collagen |
| Myasthenia Gravis | Acetylcholine receptors |
| Osteosclerosis | Type II collagen |
| Pemphigus | Intercellular substance of skin and mucosa |
| Pernicious Anemia | Gastric parietal cells, vitamin $B_{12}$ binding site of intrinsic factor |
| Premature Ovarian Failure | Interstitial cells, corpus luteum cells |
| Primary Biliary Cirrhosis | Mitochondria |
| Spontaneous infertility | Sperm cells |

The present invention is understood to include compounds that act to inhibit an immune response, and thus serve to allay the progression of autoimmune diseases and phenomena. These compounds comprise chloroquine and various analogs, such as substituted versions of 4-quinolinamine, bis-4-quinolinamine, bis-9-aminoacridine, derivatives thereof, and other weak bases. Furthermore, methods of treating autoimmune diseases using these compounds are also contemplated.

In addition to treating autoimmune diseases, the compounds and methods of the present invention are useful generally to inhibit stimulation of the immune system. Treatment and prevention of autoimmune phenomena (caused for example by myocardial infarcation), sepsis, and transplantation rejections and graft-versus-host disease are also within the scope of the present invention.

B. Transplantation Rejections and Graft-Versus-Host Disease

Transplant rejections occur as a consequence of an immune response against the transplanted organ, tissue, or cells. Antigens on the surface of the transplanted material act to signal that it is foreign, and a response ensues. Conversely, GVHD occurs when the graft mounts an immune response against the host, which can happen following a bone marrow transplant. Lymphocytes in the donor marrow produce antibodies against the host and attempts to destroy cells of the host. It occurs in approximately 40% of patients receiving an allogeneic transplant.

Because immunostimulation occurs in both of these situations, the compounds and methods of the present invention can be used as treatments to inhibit an immune response and thus alleviate or eliminate their destructive outcomes.

C. Sepsis

Sepsis can be caused by many different infectious agents and microbial organisms that may or may not be involved directly with bloodstream infection. It is a condition characterized by an inflammatory response. The term "sepsis" as used herein broadly refers to conditions known as sepsis, septic shock, systemic inflammatory response syndrome (SIRS), and multiple organ dysfunction syndrome (MODS). Because these conditions are caused by an inflammatory response of the immune system, the compounds and methods of the present invention can be employed as preventative and therapeutic treatments to inhibit an immune response and reduce the incidence of sepsis.

D. Chloroquine, Chloroquine Analogs, and Other Weak Bases

Chloroquine and a number of its structural analogs specifically and powerfully inhibit the immunostimulatory effect of unmethylated CpG-motifs at nanomolar concentration. A large variety of analogs have been constructed, many of which possess some inhibitory effect on the immunostimulatory capacity of CpG-motifs (see FIG. 1). Both chloroquine and quinacrine as well as analogs bind to duplex DNA by intercalation in a relatively sequence-nonspecific fashion (Wilson, 1998). Compounds with only two fused aromatic rings (such as chloroquine) are poor intercalators and bind to DNA less avidly than quinacrine and other related tricyclic systems. The two charged groups on chloroquine and quinacrine significantly enhance their binding to DNA, and both compounds bind to duplex DNA much more tightly at low salt concentrations that at higher salt.

Chloroquine, hydroxychloroquine and quinacrine also are known to induce remissions of systemic lupus erythematosus and rheumatoid arthritis by an unknown mechanism. These drugs bind to DNA by intercalation. They are weak bases and partition into acidic vesicles. At high concentrations, chloroquine can collapse the pH gradient and disrupt the action of endosomal hydrolytic enzymes and the trafficking of receptors.

The compounds of the present invention include substituted 4-quinolinamines (Structures A, B and C), substituted bis-4-quinolinamines (Structure D), substituted bis-9-aminoacridines (Structure E) and substituted 4-quinolinamines, substituted 9-aminoacridines combinations (Structure F).

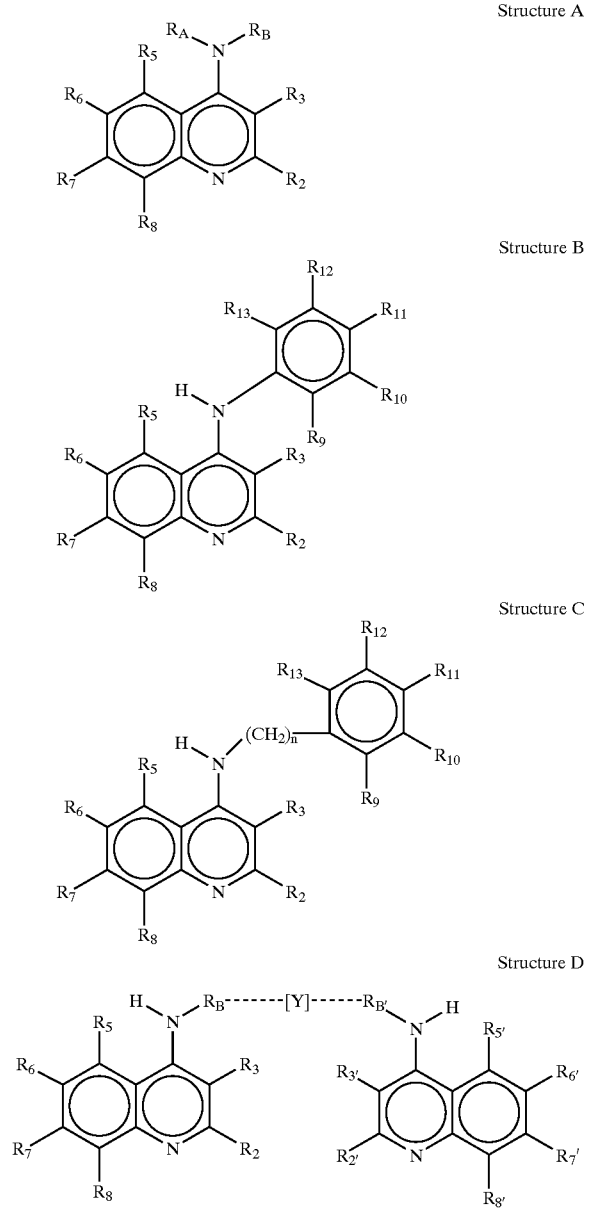

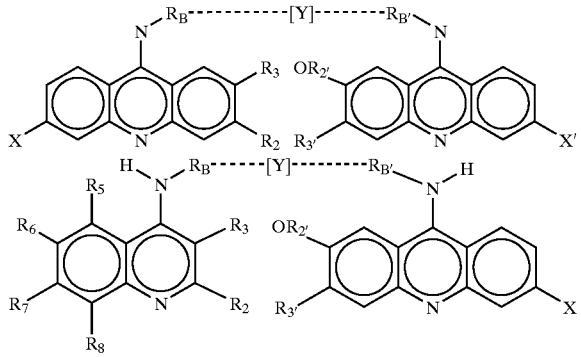

In certain embodiments of the present invention, substituted 4-quinolinamines comprise substituted or unsubstituted alkyl, alkenyl or alkynyl secondary or tertiary amine groups at the 4 position (Structure A). Substituted 4-quinolinamines also may comprise a substituted or unsubstituted phenyl group (Structure B) directly attached at the 4-amine position of the quinolinamine, or can be spatially distanced from the quinolinamine 4-amine position by a lower alkyl group (Structure C). In one preferred embodiment, a hydroxy group is attached to a substituted phenyl group. Contemplated also are one or more substitutions at phenyl group positions $R_9$, $R_{10}$, $R_{11}$, $R_{12}$ and $R_{13}$, of Structures B and C. In preferred embodiments, the $R_A$ group of the 4-quinolinamine is a hydrogen atom, as opposed to larger alkyl groups. The $R_2$ position of the substituted 4-quinolinamine compounds of the invention can be a substituted or unsubstituted phenyl group, a substituted or unsubstituted naphthyl group, an substituted or unsubstituted anthracyl group, a substituted or unsubstituted phenanthryl group or a substituted or unsubstituted styryl group. Preferably, larger aromatic groups are substituted at the $R_2$ position, which has been demonstrated to increase 4-quinolinamine activity.

As will be understood by those of skill in the art, small modification and changes may be made in the structure of the described substituted 4-quinolinamines, bis-4-quinolinamines, bis-9-aminoacridines and 4-quinolinamines, 9-aminoacridines combinations that inhibits immunostimulation. Furthermore, certain functional groups may be substituted for other functional groups without appreciable loss of immunosuppression. Since it is the inhibitory capacity and nature of an analog that defines its activity, certain chemical substitutions can be made in the structure and nevertheless obtain an analog with like properties. It is thus contemplated by the inventor that various changes may be made in an analog without appreciable loss of its immunosuppressive utility or activity.

II. Inhibitors of Immunostimulation

The invention involves compositions and methods that effect inhibition of immunostimulation. As used herein, the terms "inhibition of immunostimulation" or "to inhibit immunostimulation" refer to an ability to suppress or reduce, even slightly, an immune response. An immune response can be evidenced by a number of characteristics including, but not limited to, production of lymphokines or cytokines, release of lymphokines or cytokines, proliferation of lymphocytes, activation of lymphocytes, complement fixing, induction of the complement cascade, production of antibodies, release of antibodies, release of inflammatory mediators, and binding of T cells to a T-cell receptor.

A. CpG Motifs

Bacterial DNA is increasingly recognized as a powerful modulator of immunity (Krieg, 1996, *Trends in Microbiol.*, 4:73–6), stimulating the polyclonal proliferation of B-cells and the production of cytokines by monocytes and other cells (Ballas et al., 1996. *J. Immunol.*, 157:1840–5). This activity is attributed to unmethylated CpG sequences in bacterial DNA, which are uncommon in vertebrate DNA (Krieg et al., 1995, *Nature*, 374:546–9). Single stranded oligodeoxynucleotides that have the motif PuPuCGPyPy (CpG-ODN) mimic many of the actions of bacterial DNA (Krieg et al., 1996, *Antisense & Nucleic Acid Drug Devel.*, 6:133–9), and powerfully inhibit the induction of apoptosis in mouse WEHI 231 B-cells by anti-surface IgM (Yi et al., 1996, *J. Immunol.*, 157:4918–25; Macfarlane et al., 1997, *Immunology* 91:386). This system is a convenient and reproducible model to study responses to immunostimulatory DNA.

The term "CpG" refers to a nucleic acid sequence or molecule having a cytosine connected by a phosphorous-containing link to the 5' end of a guanosine. The term "methylated CpG" refers to the methylation of the cytosine on the pyrimidine ring, usually occurring at the 5-position of the pyrimidine ring. The term "CpG-motif" refers to a nucleic acid sequence or molecule having CpG in a context that is immunostimulatory, especially when the CpG is adjacent to two purines on its 5' end and two pyrimidines on its 3' end.

Bacterial DNA immobilized on beads does not stimulate immune responses, suggesting that internalization of the DNA is required for activity. DNA and oligodeoxynucleotides are endocytosed into acidic vesicles, and are then transported to the cytoplasm and nucleus of cells.

The mechanism of inhibition by chloroquine and its analogs was examined using 4-aminoquinolines, quinacrine, 9-aminoacridines, and novel dibasic analogs, many of which are fluorescent. WEHI 231 murine B-lymphoma cells accumulated analogs up to a concentration several hundred-fold higher than the medium. Uptake was rapid, non-saturable, reversible, and partially inhibited by monensin, an agent that collapses pH gradients within cells. Uptake did not correlate highly with efficacy as inhibitors of CpG-ODN-induced effects, suggesting that analogs act by a specific action. Confocal microscopy revealed analogs concentrating in large peripheral organelles. CpG-ODN is taken up into acidified, small, perinuclear vesicles by cells, which uptake is believed to be necessary for immunostimulatory activity. This cellular uptake of fluorescent CpG-ODN is not inhibited by the analogs. The pH of intracellular CpG-ODN (6.4) was not affected by analogs at the concentration required for inhibition, but pH was increased by higher concentrations. UV-spectroscopy revealed no binding of analogs to CpG-ODN. Nuclear Overhauser effect spectroscopy revealed that an analog bound to phosphatidylcholine vesicles, with the ring structure of the analog buried within the lipid and the side-chain facing the aqueous environment. The conclusion is that the analogs do not inhibit the action of CpG-ODN by preventing the uptake or acidification of CpG-ODN.

B. Linkers/Coupling Agents

If desired, dimers or multimers of the chloroquine analogs may be joined via a biologically-releasable bond, such as a selectively-cleavable linker or amino acid sequence. For example, peptide linkers that include a cleavage site for an enzyme preferentially located or active within a tumor environment are contemplated. Exemplary forms of such peptide linkers are those that are cleaved by urokinase, plasmin, thrombin, Factor IXa, Factor Xa, or a metallaproteinase, such as collagenase, gelatinase, or stromelysin.

Additionally, while numerous types of disulfide-bond containing linkers are known which can successfully be employed to conjugate the toxin moiety with the targeting agent, certain linkers will generally be preferred over other linkers, based on differing pharmacologic characteristics and capabilities. For example, linkers that contain a disulfide bond that is sterically "hindered" are to be preferred, due to their greater stability in vivo, thus preventing release of the toxin moiety prior to binding at the site of action.

Cross-linking reagents are used to form molecular bridges that tie together functional groups of two different molecules, e.g., a stablizing and coagulating agent. However, it is contemplated that dimers or multimers of the same analog can be made or that heteromeric complexes comprised of different analogs can be created. To link two different compounds in a step-wise manner, heterobifunctional cross-linkers can be used that eliminate unwanted homopolymer formation.

TABLE 2

HETERO-BIFUNCTIONAL CROSS-LINKERS

| linker | Reactive Toward | Advantages and Applications | Spacer Arm Length\after cross-linking |
| --- | --- | --- | --- |
| SMPT | Primary amines Sulfhydryls | Greater stability | 11.2 A |
| SPDP | Primary amines Sulfhydryls | Thiolation Cleavable cross-linking | 6.8 A |
| LC-SPDP | Primary amines Sulfhydryls | Extended spacer arm | 15.6 A |
| Sulfo-LC-SPDP | Primary amines Sulfhydryls | Extended spacer arm Water-soluble | 15.6 A |
| SMCC | Primary amines Sulfhydryls | Stable maleimide reactive group Enzyme-antibody conjugation Hapten-carrier protein conjugation | 11.6 A |
| Sulfo-SMCC | Primary amines Sulfhydryls | Stable maleimide reactive group Water-soluble Enzyme-antibody conjugation | 11.6 A |
| MBS | Primary amines Sulfhydryls | Enzyme-antibody conjugation Hapten-carrier protein conjugation | 9.9 A |
| Sulfo-MBS | Primary amines Sulfhydryls | Water-soluble | 9.9 A |

TABLE 2-continued

HETERO-BIFUNCTIONAL CROSS-LINKERS

| linker | Reactive Toward | Advantages and Applications | Spacer Arm Length\after cross-linking |
|---|---|---|---|
| SIAB | Primary amines Sulfhydryls | Enzyme-antibody conjugation | 10.6 A |
| Sulfo-SIAB | Primary amines Sulfhydryls | Water-soluble | 10.6 A |
| SMPB | Primary amines Sulfhydryls | Extended spacer arm Enzyme-antibody conjugation | 14.5 A |
| Sulfo-SMPB | Primary amines Sulfhydryls | Extended spacer arm Water-soluble | 14.5 A |
| EDC/Sulfo-NHS | Primary amines Carboxyl groups | Hapten-Carrier conjugation | 0 |
| ABH | Carbohydrates Nonselective | Reacts with sugar groups | 11.9 A |

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagents for use in immunotoxins is SMPT, which is a bifunctional cross-linker containing a disulfide bond that is "sterically hindered" by an adjacent benzene ring and methyl groups. It is believed that stearic hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linking linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art.

In preferred embodiments utilizing linkers, flexible linkers are employed to create conjugates.

Once conjugated, the analog generally will be purified to separate the conjugate from unconjugated analog or coagulants and from other contaminants. A large a number of purification techniques are available for use in providing conjugates of a sufficient degree of purity to render them clinically useful. Purification methods based upon size separation, such as gel filtration, gel permeation or high performance liquid chromatography, will generally be of most use.

C. Combined Therapy with Analogs and Traditional Treatment In many therapies, it will be advantageous to provide more than one functional therapeutic. Such "combined" therapies may have particular import in treating aspects of autoimmune diseases/phenomena and tissue/organ rejections. Thus, one aspect of the present invention utilizes at least one chloroquine analog compound for treatment of immunostimulation, while a second therapy also is provided.

The non-targeted treatment may precede or follow the targeted agent treatment by intervals ranging from minutes to weeks. In embodiments where the other agent and analogs are applied separately to the cell, one would generally ensure that a significant period of time did not expire between the time of each delivery, such that the agent and analog would still be able to exert an advantageously combined effect on the cell. In such instances, it is contemplated that one would contact the cell with both modalities within about 12–24 hours of each other and, more preferably, within about 6–12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either agent will be desired. Various combinations may be employed, where the analog is "A" and the non-analog is "B", as exemplified below:

A/B/A B/A/B B/B/A A/A/B B/A/A A/B/B B/B/B/A B/B/A/B

A/A/B/B A/B/A/B A/B/B/A B/B/A/A B/A/B/A B/A/A/B B/B/B/A

A/A/A/B B/A/A/A A/B/A/A A/A/B/A A/B/B/B B/A/B/B B/B/A/B

Other combinations are contemplated. For example, in the context of the present invention, it is contemplated that the present invention's compounds and methods of inhibiting immunostimulation could be used in conjunction with non-analog agents, including steroidal treatment. To inhibit immunostimulation using the methods and compositions of the present invention, one would generally contact a "target" cell with at least one analog and at least one other agent; these compositions would be provided in a combined amount effective achieve these goals. This process may involve contacting the cells with an analog and the agent(s) or factor(s) at the same time. This may be achieved by contacting the cell with a single composition or pharmacological formulation that includes both agents, or by contacting the cell with two distinct compositions or formulations, at the same time, wherein one composition includes an analog and the other includes the agent.

Agents or factors suitable for use in a combined therapy are any chemical compound or treatment method with immunosuppressive activity; therefore, the term "immunosuppressive agent" that is used throughout this application refers to an agent with immunosuppressive activity. Immunosuppressive agents such as azathioprine and cyclosporin are employed in transplant procedures to treat and prevent rejections. Compounds or methods used to treat GVHD include corticosteroids such as prednisone, antithymocyte globulins, cyclosporine A, cyclophosphamide, and methotrexate. Thalidomide is occasionally employed in combination with one of the previously mentioned corticosteroids to treat GVHD, and it is contemplated that thalidomide could also be used in combination with the compounds of the present invention. Similarly, patients with autoimmune diseases are administered immunosuppressant medications like corticosteroids, cyclophosphamide, and azathioprine.

In the treatment of sepsis, other agents or compounds that would be useful for use in a combination therapy with the compounds and methods of the claimed invention include antibiotics such as cephalosporin, fluoroquinolones, penicillins, carbapenems, β-lactams-β-lactamase inhibitors, ampicillin, vancomycin, metronidazole, clindamycin, and trovafloxacin, as well as with corticosteroids, vasopressor agents, vasoconstrictors, and beta agonists.

The skilled artisan is directed to "Remington's Pharmaceutical Sciences" 15th Edition, chapter 33, in particular pages 624–652. Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by FDA Office of Biologics standards.

The inventors propose that local, regional delivery of at least one analog will be a very efficient method for delivering a therapeutically effective compound to counteract the clinical disease. Similarly, the immunosuppressive agent may be directed to a particular, affected region of the subject's body. Alternatively, systemic delivery of compounds and/or the agents may be appropriate in certain circumstances, for example, where extensive tissue damage has occurred.

III. Therapeutic Formulations and Routes of Administration

The present invention discloses the compositions and methods involving a CpG analog that inhibits stimulation of the immune system. Where clinical applications are contemplated, it will be necessary to prepare the compositions of the present invention as pharmaceutical compositions, i.e., in a form appropriate for in vivo applications. Generally, this will entail preparing compositions that are essentially free of pyrogens, as well as other impurities that could be harmful to humans.

A. Formulations

The compounds of the present invention may be operatively linked or attached to a selective agent or compound. Different and varied therapeutic compounds are illustrated, which include chloroquines and its analogs and derivatives. Liposomes and carrier molecules containing any of the foregoing are also contemplated.

One will generally desire to employ appropriate salts and buffers to render compositions stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

The active compositions of the present invention include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra.

The active compounds may be administered via any suitable route, including parenterally or by injection or inhalation. Solutions of the active compounds as free base or pharmacologically acceptable salts can be prepared in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, histidine, procaine and the like.

Compositions may be conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides: such suppositories may be formed from mixtures containing the active ingredient in the range of about 0.5% to about 10%, preferably about 1 to about 2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain about 10 to about 95% of active ingredient, preferably about 25 to about 70%.

1. Liposomes as Carriers of Selected Compounds

In one embodiment of the invention, the selected compound of the present invention may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are cationic lipid-nucleic acid complexes, such as lipofectamine-nucleic acid complexes.

"Liposome" is a generic term encompassing a variety of single and multilamellar lipid vehicles formed by the generation of enclosed lipid bilayers. Phospholipids are used for preparing the liposomes according to the present invention and can carry a net positive charge, a net negative charge or are neutral. Dicetyl phosphate can be employed to confer a negative charge on the liposomes, and stearylamine can be used to confer a positive charge on the liposomes.

Lipids suitable for use according to the present invention can be obtained from commercial sources. For example, dimyristyl phosphatidylcholine ("DMPC") can be obtained from Sigma Chemical Co., dicetyl phosphate ("DCP") is obtained from K & K Laboratories (Plainview, N.Y.); cholesterol ("Chol") is obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform, chloroform/methanol or t-butanol can be stored at about $-20°$ C. Preferably, chloroform is used as the only solvent since it is more readily evaporated than methanol.

Phospholipids from natural sources, such as egg or soybean phosphatidylcholine, brain phosphatidic acid, brain or plant phosphatidylinositol, heart cardiolipin and plant or bacterial phosphatidylethanolamine are preferably not used as the primary phosphatide, i.e., constituting 50% or more of the total phosphatide composition, because of the instability and leakiness of the resulting liposomes.

Liposomes used according to the present invention can be made by different methods. The size of the liposomes varies depending on the method of synthesis. A liposome suspended in an aqueous solution is generally in the shape of a spherical vesicle, having one or more concentric layers of lipid bilayer molecules. Each layer consists of a parallel array of molecules represented by the formula XY, wherein X is a hydrophilic moiety and Y is a hydrophobic moiety. In aqueous suspension, the concentric layers are arranged such that the hydrophilic moieties tend to remain in contact with an aqueous phase and the hydrophobic regions tend to self-associate. For example, when aqueous phases are present both within and without the liposome, the lipid molecules will form a bilayer, known as a lamella, of the arrangement XY-YX.

Liposomes within the scope of the present invention can be prepared in accordance with known laboratory techniques. In one preferred embodiment, liposomes are prepared by mixing liposomal lipids, in a solvent in a container, e.g., a glass, pear-shaped flask. The container should have a volume ten-times greater than the volume of the expected suspension of liposomes. Using a rotary evaporator, the solvent is removed at approximately 40° C. under negative pressure. The solvent normally is removed within about 5 min to 2 hours, depending on the desired volume of the liposomes. The composition can be dried further in a desiccator under vacuum. The dried lipids generally are discarded after about 1 week because of a tendency to deteriorate with time.

Dried lipids can be hydrated at approximately 25–50 mM phospholipid in sterile, pyrogen-free water by shaking until all the lipid film is resuspended. The aqueous liposomes can be then separated into aliquots, each placed in a vial, lyophilized and sealed under vacuum.

In the alternative, liposomes can be prepared in accordance with other known laboratory procedures: the method of Bangham et al. (1965), the contents of which are incorporated herein by reference; the method of Gregoriadis, as described in *DRUG CARRIERS IN BIOLOGY AND MEDICINE*, G. Gregoriadis ed. (1979) pp. 287–341, the contents of which are incorporated herein by reference; the method of Deamer and Uster (1983), the contents of which are incorporated by reference; and the reverse-phase evaporation method as described by Szoka and Papahadjopoulos (1978). The aforementioned methods differ in their respective abilities to entrap aqueous material and their respective aqueous space-to-lipid ratios.

The dried lipids or lyophilized liposomes prepared as described above may be reconstituted in a solution of nucleic acid and diluted to an appropriate concentration with an suitable solvent, e.g., DPBS. The mixture is then vigorously shaken in a vortex mixer. Unencapsulated nucleic acid is removed by centrifugation at 29,000×g and the liposomal pellets washed. The washed liposomes are resuspended at an appropriate total phospholipid concentration, e.g., about 50–200 mM. The amount of nucleic acid encapsulated can be determined in accordance with standard methods. After determination of the amount of nucleic acid encapsulated in the liposome preparation, the liposomes may be diluted to appropriate concentration and stored at 4° C. until use.

In another embodiment, the lipid dioleoylphosphatidylchoine is employed. Nuclease-resistant oligonucleotides were mixed with lipids in the presence of excess t-butanol. The mixture was vortexed before being frozen in an acetone/dry ice bath. The frozen mixture was lyophilized and hydrated with Hepes-buffered saline (1 mM Hepes, 10 mM NaCl, pH 7.5) overnight, and then the liposomes were sonicated in a bath type sonicator for 10 to 15 min. The size of the liposomal-oligonucleotides typically ranged between 200–300 nm in diameter as determined by the submicron particle sizer autodilute model 370 (Nicomp, Santa Barbara, Calif.).

Liposomes are formed from phospholipids that are dispersed in an aqueous medium and spontaneously form multilamellar concentric bilayer vesicles. Liposomes bear many resemblances to cellular membranes and are contemplated for use in connection with the present invention as drug delivery agents.

The formation and use of liposomes is generally known to those of skill in the art. For example, several U.S. Patents concern the preparation and use of liposomes that encapsulate biologically active materials, eg., U.S. Pat. Nos. 4,485, 054; 4,089,801: 4,234,871; and 4,016,100; each incorporated herein by reference. Mostly, it is contemplated that intravenous injection of liposomal preparations would be used, but pessaries are also possible.

B. Routes of Administration

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration.

1. Nasal Administration

One may also use nasal solutions or sprays, aerosols or inhalants in the present invention. Nasal solutions are usually aqueous solutions designed to be administered to the nasal passages in drops or sprays. Nasal solutions are prepared so that they are similar in many respects to nasal secretions, so that normal ciliary action is maintained. Thus, the aqueous nasal solutions usually are isotonic and slightly buffered to maintain a pH of 5.5 to 6.5.

In addition, antimicrobial preservatives, similar to those used in ophthalmic preparations, and appropriate drug stabilizers, if required, may be included in the formulation. Various commercial nasal preparations are known and include, for example, antibiotics and antihistamines and are used for asthma prophylaxis.

2. Oral Administration

In certain embodiments, active compounds may be administered orally. This is contemplated to be useful as many substances contained in tablets designed for oral use are absorbed by mucosal epithelia along the gastrointestinal tract.

Also, if desired, the peptides, antibodies and other agents may be rendered resistant, or partially resistant, to proteolysis by digestive enzymes. Such compounds are contemplated to include chemically designed or modified agents; dextrorotatory peptides; and peptide and liposomal formulations in time release capsules to avoid peptidase and lipase degradation.

For oral administration, the active compounds may be administered, for example, with an inert diluent or with an assimilable edible carrier, or they may be enclosed in hard or soft shell gelatin capsule, or compressed into tablets, or incorporated directly with the food of the diet. For oral therapeutic administration, the active compounds may be incorporated with excipients and used in the form of ingestible tablets, buccal tables, troches, capsules, elixirs, suspensions, syrups, wafers, and the like.

The oral compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier.

Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

Upon formulation, the compounds will be administered in a manner compatible with the dosage formulation and in such amount as is therapeutically effective. The formulations are easily administered in a variety of dosage forms, as described herein.

3. Pessaries

Additional formulations which are suitable for other modes of administration include vaginal suppositories and pessaries. A rectal pessary or suppository may also be used.

Suppositories are solid dosage forms of various weights and shapes, usually medicated, for insertion into the rectum, vagina or the urethra. After insertion, suppositories soften, melt or dissolve in the cavity fluids.

In general, for suppositories, traditional binders and carriers may include, for example, polyalkylene glycols or triglycerides; such suppositories may be formed from mixtures containing the active ingredient in the range of 0.5% to 10%, preferably 1%–2%.

Vaginal suppositories or pessaries are usually globular or oviform and weighing about 5 g each. Vaginal medications are available in a variety of physical forms, e.g., creams, gels or liquids, which depart from the classical concept of suppositories. Vaginal tablets, however, do meet the definition, and represent convenience both of administration and manufacture.

"Unit dose" is defined as a discrete amount of a therapeutic composition dispersed in a suitable carrier. In this connection, sterile aqueous media which can be employed will be known to those of skill in the art in light of the present disclosure. For example, a unit dose could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

B. Kits

All the essential materials and reagents required for delivering analogs and agents to effect inhibition of immunostimulation may be assembled together in a kit. This generally will comprise selected analogs prepared in an adminsterable formulation or prepared for use as an adminsterable formulation. Such kits will comprise distinct containers for each individual reagent.

When the components of the kit are provided in one or more liquid solutions, the liquid solution preferably is an aqueous solution, with a sterile aqueous solution being particularly preferred. For in vivo use, the expression construct may be formulated into a pharmaceutically acceptable syringeable composition. In this case, the container means may itself be an inhalent, syringe, pipette, eye dropper, or other such like apparatus, from which the formulation may be applied to an infected area of the body, such as the lungs, injected into a subject, or even applied to and mixed with the other components of the kit.

The components of the kit may also be provided in dried or lyophilized forms. When reagents or components are provided as a dried form, reconstitution generally is by the addition of a suitable solvent. It is envisioned that the solvent also may be provided in another container means.

The kits of the present invention also will typically include a means for containing the vials in close confinement for commercial sale such as, e.g., injection or blow-molded plastic containers into which the desired vials are retained.

Irrespective of the number or type of containers, the kits of the invention also may comprise, or be packaged with, an instrument for assisting with the injection/administration or placement of the ultimate complex composition within the body of an animal. Such an instrument may be an inhalant, syringe, pipette, forceps, measured spoon, eye dropper or any such medically approved delivery vehicle.

IV. EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Structure-Activity Relationship Analysis of Substituted 4-Amioquinolinamines

A detailed structure-activity relationship (SAR) analysis of quinoline antagonists of immunostimulatory CpG-ODNs was undertaken. The structure of compounds 1–32 are shown in Tables 4–9. The synthesis work together with SAR analysis of the synthesized quinolines culminated in the finding of an extremely active agent 32.

Substituted quinolines 1 (Strekowski et al., 1996), 3 (Strekowski et al., 1996), 4 (Strekowski et al., 1991), 6 (Strekowski et al., 1996) (Table 4), 7 (Strekowski et al., 1996), 9 (Strekowski et al., 1996), 10 (Strekowski et al., 1996) (Table 5), and 25 (Strekowski et al., 1997) (Table 7) were available from other studies. Compounds 2 and 5 were obtained by using a general procedure (Strekowski et al., 1992). Compounds 11 and 14 (Table 6) were obtained by treatment of 4-chloroquinoline with the corresponding amine (Strekowski et al., 1997). An efficient synthesis of 2-aryl-4-chloroquinolines has recently been reported (Strekowski et al., 1997). These compounds served as substrates for 8, 12, 13, 15, and 16, 20–24, and 26–32 (Table 8). This chemistry is illustrated in Scheme 1 for the preparation of 28 by the reaction of 4-chloro-2-naphthylquinoline with 4-hydroxyaniline. A subsequent Mannich reaction of 28 with formaldehyde and N-methylpiperazine furnished 32. Compounds 29–31 were prepared in a similar manner. Finally, the quaternary compounds 17–19 (Table 6) were synthesized by the reaction of the corresponding aminoquinolines with MeI in DMF. The initially formed iodide of 17 [15 (0.12 mmol), MeI (0.10 mmol), $Na_2CO_3$ (0.24 mmol), DMF (2 mL), stirring at 23° C. for 12 h] resisted all attempts of crystallization. A bromide/hydrobromide derivative of 17 crystallized following treatment of a solution of the iodide in MeOH with HBr (48%, 3 mmol). Dibromides 18 and 19 were prepared in a similar way by the reaction of the respective quinolines 15 and 14 (0.12 mmol) with MeI (2 mmol) followed by treatment with HBr. Solid quinolines were purified by crystallization, and oily derivatives were transformed into solid salts by using a general procedure (Strekowski et al., 1991) and the salts were crystallized. All compounds gave satisfactory results of elemental analysis and their structures were fully consistent with $^1H$ and $^{13}C$ NMR data. (Compound, mp (crystallization solvent): 2^2HBr^2H$_2$O, 264–267° C. (95% EtOH); 5^2HBr, 231–233° C. (95% EtOH); 8, 52–54° C. ($CH_2Cl_2$/Et$_2$O); 11^2H$_3$PO$_4$^H$_2$O, 222–225° C. (95% MeOH); 12^2HBr^H$_2$O, 243–245° C. (95% MeOH); 13^2HBr^H$_2$O, 249–250° C. (95% MeOH); 14^2HCl^H$_2$O, 144–147° C. (95% EtOH); 15^2HBr, 205–207° C. (95% MeOH); 17, 214–216° C. (30% MeOH); 18, 209–212 (acetone); 19^H$_2$O, 239–241° C. (95% EtOH); 20, 87–89° C. (AcOEt); 21, 65–67° C. (AcOEt); 22, 189–190° C. (Et$_2$O); 23^HBr, 220–222° C. (95% MeOH); 24^HCl^2H$_2$O, 122–129° C.

(95% MeOH); 26^H₂O, 173–175° C. (95% MeOH); 27^HCl, 267–272° C. (95% MeOH); 28^HCl^0.5H₂O, >300° C. (95% EtOH); 29^3HCl^2.5H₂O, 224–226° C. (95% EtOH); 30^4H₂O, 161–168° C. (95% MeOH); 31^3HCl^2H₂O, 213–216° C. (95% EtOH/t-BuOMe); 32^5HCl^5H₂O, 218–222° C. (95% EtOH). ¹H NMR for 32^5HCl^5H₂O (DMSO-d₆, 400 MHz): ∂2.74 (s, 6H), 3.35–3.75 (m, 16H), 4.45 (s, 4H), 7.17 (s, ¹H), 7.67 (m, 2H), 7.81 (t, J=8 Hz, 1H), 7.87 (s, 2H), 8.02–8.23 (m, 5H), 8.46 (d, J=8 Hz, 1H), 8.82 (s, 1H), 8.95 (d, J=8 Hz, 1H), 11.21 (s, exchangeable with D₂O, 1H), 12.05 (br s, exchangeable with D₂O, 1H). ¹³C NMR for 32^5HCl^5H₂O (DMSO-d₆, 75 MHz): ∂41.8, 47.5, 49.9, 54.0, 99.4, 116.3, 119.7, 120.6, 123.5, 125.1, 127.2, 127.4, 127.8, 128.5, 128.8, 129.0, 129.2, 129.4, 129.5, 131.2, 132.4, 134.2, 134.3, 138.9, 152.9, 154.7, 155.4. Spectral data for other compounds will be published in due course).

Scheme 1

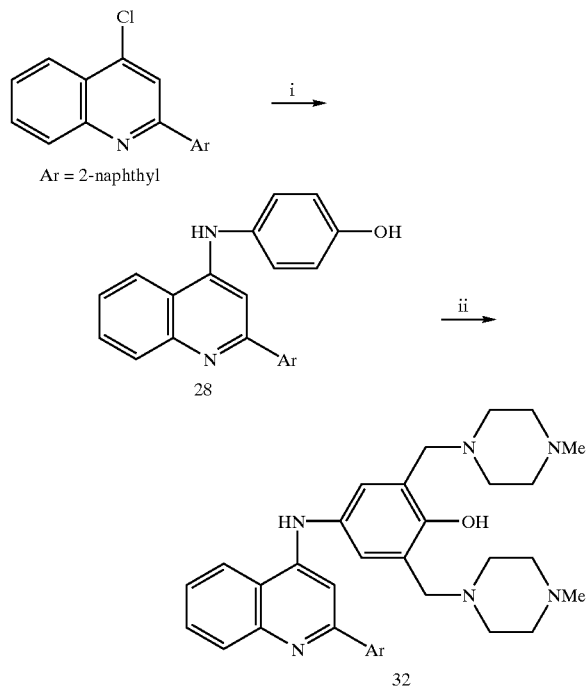

Ar = 2-naphthyl (i): p-H₂NC₆H₄OH (3equiv), 130° C., 4h, then silica gel chromatography (EtO); ii: 28 (1 mmol), N-methylpiperazine (5 mmol), aq CH₂O (13 M, 5 mmol), EtOH (20 mL), reflux, 24 h; then silica gel chromatography (AcOEt/Et₃N, 3/2).

The SAR studies were initiated following the finding that a 2-(2-naphthyl)quinoline 1 is more active than chloroquine and 2-phenylchloroquine (Table 4). It was of interest, therefore, to analyze analogs of 1 containing different groups at position 2 of the quinoline. In comparison to 1, the activity remains unchanged for 2, which contains a larger 3-phenanthryl group and is slightly decreased for the 1-naphthyl derivative 3 with a severe steric hindrance around the inter-ring bond. Interesting results are the high efficacy of quinoline 4 that is substituted with a relatively small para-tolyl group and an even greater activity for compound 5, which contains a styryl moiety. Comparison of compounds 4 and 6 reveals that the electron-withdrawing trifluoromethyl group in 6 exerts a strongly negative effect on the activity.

TABLE 4

Activities of Chloroquine,[a] 2-Phenylchloroquine,[a] and 2-Substituted 4-[2-(Dimethylamino)ethyl]quinolines 1–6

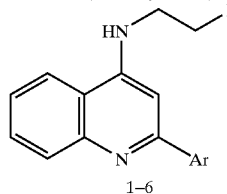

1–6

| No | Ar | EC₅₀ (nM) |
|----|-----|-----------|
| 1 | 2-naphthyl | 9.1 |
| 2 | 3-phenanthryl | 11.0 |
| 3 | 1-naphthyl | 39.8 |
| 4 | 4-MePh | 12.3 |
| 5 | trans-CH=CHPh | 6.5 |
| 6 | 4-CF₃Ph | 155 |

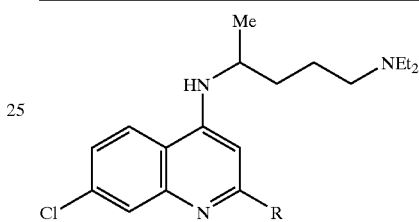

Chloroquine: R = H (EC₅₀ = 110 nM)[a]
2-Ph-chloroquine: R = Ph (EC₅₀ = 51.3 nM)[a]
[a]Taken from MacFarlane et al., 1998.
Compounds 1–6 were assayed under the same conditions. The EC₅₀ is the concentration required for half-maximal inhibition of CpG-ODN effect on thymidine uptake by WEHI 231 B-cells in the presence of å-sIgM. The estimated experimental error is ± 15%.

The effect of basicity of the ring nitrogen atom in selected quinolines 1 and 7–10 was investigated (Table 5). As discussed previously (Strekowski et al., 1996), the given pK$_a$ values are functions of electronic effects of the 4-substituent at the quinoline including inhibition of the conjugation effect in 7 due to steric hindrance. As can be seen from Table 5, the pK$_a$ values of 1, 7–10 parallel nicely the respective EC₅₀ values.

TABLE 5

The Experimental pK$_a$ Values of Quinolines 1, 7–10[a] and Their Activity

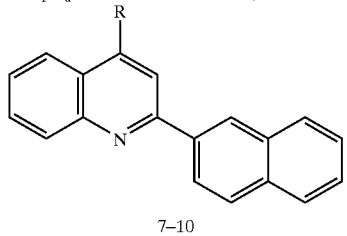

7–10

| No. | R | pKa | EC₅₀ (nM) |
|-----|---|-----|-----------|
| 1 | NH(CH₂)₂NMe₂ | 7.1 | 9.1 |
| 7 | N(Me)(CH₂)₂NMe₂ | 6.2 | 416 |
| 8 | O(CH₂)₂NMe₂ | 6.1 | 478 |
| 9 | S(CH₂)₂NMe₂ | 4.4 | 2400 |
| 10 | C(O)NH(CH₂)₂NMe₂ | 2.9 | >10,000 |

[a]The values for 1, 7, 9, and 10 are taken from Strekowski et al., J Med. Chem. 1996.

Further analogs of 1 are analyzed in Table 6. These are quinolines with and without aryl substitution, with an increasing length of the (dimethylamino)polymethylene chain, and several quaternized derivatives in which a positive charge is permanently fixed. There is a dramatic increase in activity, due to 2-aryl substitution, as can be seen from comparison of 11 to 12 and 13 and comparison of 14 to 15. On the other hand, the activities of compounds 4 and 1 containing the same (dimethylamino)dimethylene side chain are similar to those of the respective (dimethylamino) trimethylene analogs 12 and 13. As the chain length increases in the series of compounds 13, 15, and 16, which contain the same 2-(2-naphthyl)quinolin-4-amine core, the activity reaches a maximum for a tetramethylene derivative 15 and then is slightly decreased for compound 16 which has a hexamethylene linker.

TABLE 6

Activities of Quinolin-4-amines 11–18 and Quaternary Derivatives 17–19

| No. | R | n | EC$_{50}$ (nM) |
|---|---|---|---|
| 11 | H | 3 | 4400 |
| 12 | p-tolyl | 3 | 11.5 |
| 13 | 2-naphthyl | 3 | 11.0 |
| 14 | H | 4 | 316 |
| 15 | 2-naphthyl | 4 | 4.0 |
| 16 | 2-naphthyl | 6 | 5.9 |
| 17 | | | >10,000 |
| 18 | 2-naphthyl | | 7600 |
| 19 | H | | >10,000 |

Methylation of the terminal dimethylamino group of 15 rendered the resultant trimethylammonium derivative 17 completely inactive. An additional methylation of 17 at the ring nitrogen atom restored some activity in the resultant dication 18. However, a dication 19 devoid of the naphthyl group was completely inactive again. Our additional studies (not shown) consistently indicated that compound 1 and its numerous analogs with a severely sterically hindered amino function at the terminus of the side chain showed comparable activities. Accordingly, the lack of activity of 17 and 19 cannot be explained in terms of an increased bulkiness of the trimethylammonium substituent in comparison to that of the dimethylamino group.

Analogs of 1 containing an alkyl group at N4 of the quinoline were inactive as well (not shown; see, however, 26 in Table 5). On the other hand, quinolines that contain groups capable of a hydrogen bonding interaction, such as a urethane in 20 or a hydroxy group in 21–24 (Table 7) show some activity. The activity of 25, the side chain of which contains additional amino functions, is greater.

TABLE 7

Activities of N-Substituted Quinolin-4-amines

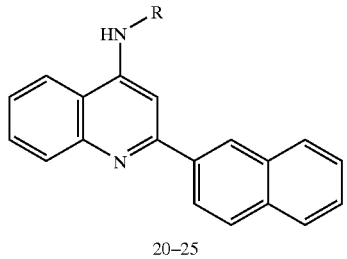

20–25

| No. | R | EC$_{50}$ (nM) |
|---|---|---|
| 20 | (CH$_2$)$_2$NHCO$_2$Bu-t | 570 |
| 21 | CH(Me)(CH$_2$)$_3$C(Me$_2$)OH | 1150 |
| 22 | CH(Me)CH(Ph)OH (erythro) | 1000 |
| 23 | (CH$_2$)$_2$O(CH$_2$)$_2$OH | 330 |
| 24 | (CH$_2$)$_6$OH | 170 |
| 25 | (CH$_2$)$_3$N(CH$_2$CH$_2$)$_2$N(CH$_2$)$_3$NHC(O)(CH$_2$)$_3$OH | 25.1 |

The activity pattern is retained in a series of substituted 4-anilinoquinolines 26–32 (Table 8). Compound 32 has a relatively basic quinoline (pK$_a$=6.9, a calculated value), contains hydroxy and amino functions, and is the most potent antagonist of immunostimulatory CpG-ODN's thus known.

TABLE 8

Activities of 4-(Substituted Anilino)quinolines

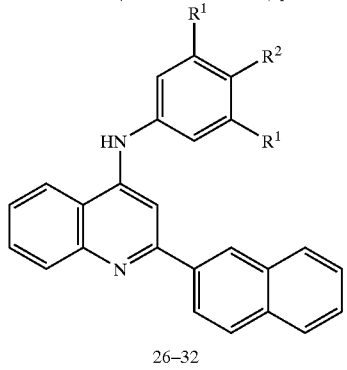

26–32

| No. | R$^1$ | R$^2$ | EC$_{50}$ (nM) |
|---|---|---|---|
| 26 | H | n-C$_4$H$_9$ | >10,000 |
| 27 | H | CH$_2$CH$_2$OH | 510 |
| 28 | H | OH | 320 |
| 29 | morpholinomethyl | OH | 10.0 |
| 30 | piperidinomethyl | OH | 1.5 |
| 31 | pyrrolidinomethyl | OH | 1.2 |
| 32 | N-methylpiperazinomethyl | OH | 0.24 |

In order to better understand the requirements for activity, eleven 2-(2-naphthyl)quinolin-4-amines of Tables 7 and 8, all containing a hydroxy group at the side chain and occasionally substituted with additional amino groups, were subjected to correlation analysis by using calculated connectivity indices. These parameters, depending on their order, encode the length and the size of a substituent and also the type and position of branching. The lipophilicity, length, and branching of hydrocarbon substituents are well characterized by the set of $^3X_p^v$ indices (Mokrosz et al., 1992).

A statistically significant QSAR correlation for the eleven substituents, all containing free (non-protonated) amino groups at the side chain, was obtained (eq 1).

$$\log(1/EC_{50})=0.534(\pm0.08)^3X_p^v+5.600(\pm0.27) \quad (1)$$

n=11 (C4 groups of 21–25 and 27–32), r=0.934, s=0.49, $F_{0.01}$=61.09

A slightly inferior correlation was obtained for the same set of substituents with protonated amino groups excepting the N4 atom at the quinoline, which is non-basic due to the strong conjugation effect (not shown).

These results and the experimental results obtained with quaternary compounds 17–19 indicate that the basic amino group ($pK_a$>8) at the side chain of an active agent is not protonated in the compound-bioreceptor complex. On the other hand, the observed $pK_a$correlation (Table 5) and the activity of the N1-quaternized quinoline 18 (The inactive compounds 17, 19 and others ($EC_{50}$>10,000 nM) were assayed at the highest concentration of 10,000 nM and showed no effect on the cell culture. The $EC_{50}$ value for 18 is 7600±1200 nM.) are consistent with protonation of the relatively less basic ring nitrogen ($pK_a$<8). It can be suggested that the free amino group is located in a lipophilic microenvironment of the bioactive complex and is involved in hydrogen-bonding interaction with a hydrogen donor of the receptor.

Since nucleic acids are involved and several compounds of this study have been shown previously to strongly stabilize a triple-helix DNA structure, it was hypothesized initially that stabilization of the triple helix complex is part of the mechanism. However, while the isomeric compounds 1 and 3 are antagonists of the CpG-induced effect and compound 1 is one of the best triplex DNA stabilizing agents known to date, the sterically hindered isomer 3 does not promote triplex DNA formation and does not bind to the triple DNA structure(Strekowski et al., 1996). While compound 1 binds weakly to duplex DNA, compound 3 does not bind at all. The two compounds do not stabilize a quadruplex DNA as well. In addition, compound 1 binds weakly to RNA (Wilson et al., 1993). Thus, it can be suggested that the mechanism of quinoline antagonists does not involve binding to CpG-ODN.

4-Quinolinamines that inhibit CpG-ODN-induced effects are weak bases. Weak bases tend to partition into acidified vesicles within cells (de Duve et al., 1974). Chloroquine has been well studied in this regard. It concentrates in lysosomes and collapses the pH gradient (Ohkuma and Poole, 1981), leading to the hypothesis that organelle acidification is required for intracellular recognition of CpG-ODN (Yi et al., 1998). However, this hypothesis is not consistent with the activity of a diquaternary derivative 18, which is not a base. In addition, a number of independent experiments consistently indicated that the active compounds do not inhibit the action of CpG-ODN by interfering with the acidification of vesicles, nor with the uptake or subcellular distribution of CpG-ODN (see below). In summary, it seems most likely that these agents inhibit the detector system for CpG-ODN by a specific mechanism, not by a bulk effect.

Example 2

Materials and Methods

A. Cell Culture

WEHI 231 murine B-lymphoma cells were maintained at log phase in medium as previously described (Macfarlane and Manzel, 1998).

B. Analogs

The structures of the analogs the inventors used are shown in FIG. 1. The pyrimidine derivatives 215, 227, 228 and 231 (Strekowski et al., 1991) and 2-naphthylquinolines 91, 267, 350 and 352 (Strekowski et al., 1992; Strekowski et al., 1994) were prepared by using general synthetic methodologies developed for similar compounds. Synthetic details will be reported elsewhere. All compounds were at least 98% pure as indicated by elemental analysis and analysis of their proton NMR spectra. The dimeric compounds 322 and 329 have been described (Ismail et al., 1996). The other analogs have been previously reported (Macfarlane and Manzel, 1998) and were kindly supplied by Dr Jill Johnson from the National Cancer Institute, or purchased. The analogs were dissolved in dimethyl sulfoxide at a concentration of 10 mM, and thereafter diluted in culture medium to the desired concentration.

C. Efficacy of Analogs

The efficacy of analogs as inhibitors of CpG-ODN-induced responses was determined using [$^3$H]-thymidine uptake by WEHI-231 cells treated for 24 hr with anti-surface-IgM (which kills the cells by apoptosis), ODN1760 (which protects against this cell killing), and a range of concentrations of an analog (which reverses the protection by CpG-ODN) as previously described in detail (Macfarlane and Manzel, 1998).

D. Cellular Uptake of Analogs

Cellular uptake of analogs was estimated by fluorescence. WEHI-231 cells (5×10$^6$/ml) were incubated in RPMI 1640 without phenol red (Gibco BRL, Gaithersburg, Md.) with the indicated concentration of analog for 30 min. The cells were pelleted by centrifugation, and the fluorescence of the supernatant was measured after dilution with the appropriate buffer. The cell pellet was extracted with 1 ml Catrimox-14 (Iowa Biotechnology Corp., Coralville, La.), and the insoluble nucleic acids were removed by centrifugation (16,000×g, 10 min). The resulting extract was diluted with the appropriate buffer, and its fluorescence was measured. Preliminary experiments revealed that the Catrimox-14 extract contained essentially all of the cell-associated analog. The fluorescence intensity and spectra were determined with a Farrand Manual Spectrofluorometer at three pH's (3.4, 7.4, 10.0). Subsequent measurements of fluorescence were performed at pH giving the highest yield (Table I). Fluorescence intensity was converted to concentration using standard curves prepared by diluting each analog (0.1–5 μM) in Catrimox-14- and RPMI-containing buffer.

E. Uptake of CpG-ODN

WEHI 231 cells were incubated with 5 μg/ml Texas Red labeled ODN 1760. After incubation with the additions indicated, the cells were centrifuged and resuspended three times into Hanks buffered salt solution at 37° to remove surface bound ODN, and then resuspended and fixed in 2% paraformaldehyde for analysis in the University of-Iowa Flow Cytometry Facility. 10,000 events were recorded using a Coulter EPICS 753 at 488/600 nm, gating out dead cells. The mean cellular fluorescence was recorded.

F. pH of CpG-ODN-Containing Cells

The pH of CpG-ODN within cells was estimated by taking advantage of the fact that acidification suppresses the fluorescence of fluorescein (Tonkinson and Stein, 1994;

Ohkuma and Poole, 1978). WEHI-231 cells ($1 \times 10^6$/ml) were incubated with fluorescein-labeled ODN 1760 (5 µg/ml, 2 hr), and washed as described above. The fluorescence of the live cells was determined by flow cytometry immediately after the addition of analogs or monensin (10 µM). The pH of the ODN containing compartment was determined from the increase in the fluorescence that occurred when monensin was added, assuming that monensin equilibrates this compartment with the medium (pH 7.4). The inventors calibrated this assay using a standard curve of fluorescence of fluorescein-labeled ODN 1760 at a range of pH's, which procedure yielded a pKa of 6.98 in 25 mM Tris acetate/150 mM NaCl buffer.

G. Confocal Microscopy

WEHI 231 cells were incubated with 5 µg/ml Texas Redlabeled ODN 1760 plus additions as indicated. The cells were washed three times to remove surface bound ODN, centrifuged onto glass slides using a cytocentrifuge, and immediately fixed with 2% paraformaldehyde. The cells were photographed with a BioRad (Richmond, Calif.) MAC-1024 confocal laser scanning imaging system.

H. Confocal Microscopy of Live Cells

Preliminary studies established that paraformaldehyde does not prevent the leaching of quinacrine (Duve et aL., 1974) or other analogs from the cells. The distribution of these compounds was therefore observed in live cells. WEHI 231 cells were incubated with 50 nM quinacrine for 30 min. Cells were then wet mounted on a Fisher brand charged slide, covered with a coverslip, and photographed live as above. For comparison, cells were also incubated with 5 µg/ml Texas Red-labeled ODN 1760 for 2 hr, washed, resuspended in RPMI 1640 without phenol red and wet mounted live.

I. NOESY of ODN Interaction with Phospholipid

Preparation of vesicles was based on the procedures of Bammel et al. (Bammel et al., 1986). Compound 91 in solid form was added to the vesicle suspension that was then stirred for 12–15 hr at 35° C. This addition procedure avoids changing the solvent composition and follows the post-membrane-preparation extrinsic ligand addition practice used in functional preparations. The compound 91 content in the DMPC vesicles was limited to 8 mol percent to avoid phase separation in the bilayer.

Phase-sensitive two-dimensional NOESY spectra of sonicated DMPC vesicles to which compound 91 was bound were obtained using a Varian Unity Plus spectrometer operating at a proton frequency of 500 MHz. The pulse sequence developed by States et al. (States et al., 1982) was used for data acquisition. The probe temperature was set at 35° C. for all studies. An optimum spectral width of 4773.3 Hz was determined for the initial NOESY study and maintained for all subsequent acquisitions. An optimum balance of sensitivity and resolution was obtained by using 256 t1 increments each consisting of 2048 data points that were signal-averaged over 128 scans with a relaxation delay of 2 s and 215 ms acquisition time while mixing times of 50 and 150 ms were employed. Very similar NOESY spectra were obtained using both of the aforementioned mixing times. In order to minimize the possible appearance of artifactual cross peaks due to spin diffusion, NOESY spectra obtained with a 50 ms mixing time only are considered and presented herein. Suppression of the residual HOD signal was accomplished by saturation with the receiver at a power setting of 24 Hz [1/(4 PW90)]. Data processing was performed using the program VNMR supplied by Varian Associates, Inc. The free induction decays were zero filled to 2K data points in the t1 dimension. The data presented as NOESY spectra were analyzed using a sinebell window function shifted by 60°. Linear prediction (Gray, 1990) was used to obtain the first two points in the FID's and to extend the number of increments from 256 to 512 in the F1 dimension. Using the algorithm of Brown (Brown, 1995), base line correction was applied to both dimensions after fourier transformation of data in the t2 and t1 dimensions. A fourth order polynomial was usually employed for these corrections. The two-dimensional contour plots are shown in pure absorption phase.

J. DNA Thermal Melting

Thermal melting studies were conducted at 260 nm with a Cary spectrophotometer interfaced to a microcomputer. A thermistor fixed into a reference cuvette was used to monitor the temperature. The DNA oligomer was added to 1 mL of buffer (MES with 150 mM KCl, pH 4.4) in 1 cm path length reduced-volume quartz cells. Studies were generally conducted a at concentration of $5 \times 10^{-5}$M bases. Studies with chloroquine 15 and quinacrine 17 were at a ratio of 0.3 moles of compound per base.

K CpG oligonucleotides

CpG-ODN 1760, synthesized with a phosphorothioate backbone, has the sequence:

5'-ATAATCGACGIlCAAGCAAG3'

The fluorescent ODNs were ODN 1760 with either fluorescein or Texas Red linked to the 5'-terminus. The oligodeoxynucleotides were purchased from Genosys (The Woodlands, IX). 1,2-dimyristoyl-sn-glycero-3-phosphocholine (DMPC) was obtained in powder form from Avanti Polar Lipids, Alabaster, Ala., USA. The lipid was prepared synthetically and was at least 99.9 percent pure. ACS reagent grade KCl and dibasic potassium phosphate were obtained from the Fisher Scientific Co. $D_2O$ at 99.9 percent purity was obtained from either Cambridge Isotope Laboratories, Woburn, Mass. or Isotec, Inc., Miamisburgh, Ohio. Monensin, chloroquine, quinine, and quinacrine were purchased from Sigma Chemical Co. (St. Louis, Mo.). Hydroxychloroquine was purchased from Copley Pharmaceutical, Inc. (Canton, Mass.). Charged microscope slides were purchased from Fisher Scientific (Pittsburgh, Pa.).

Example 3

Cellular Uptake of Analogs

Figure 2A:
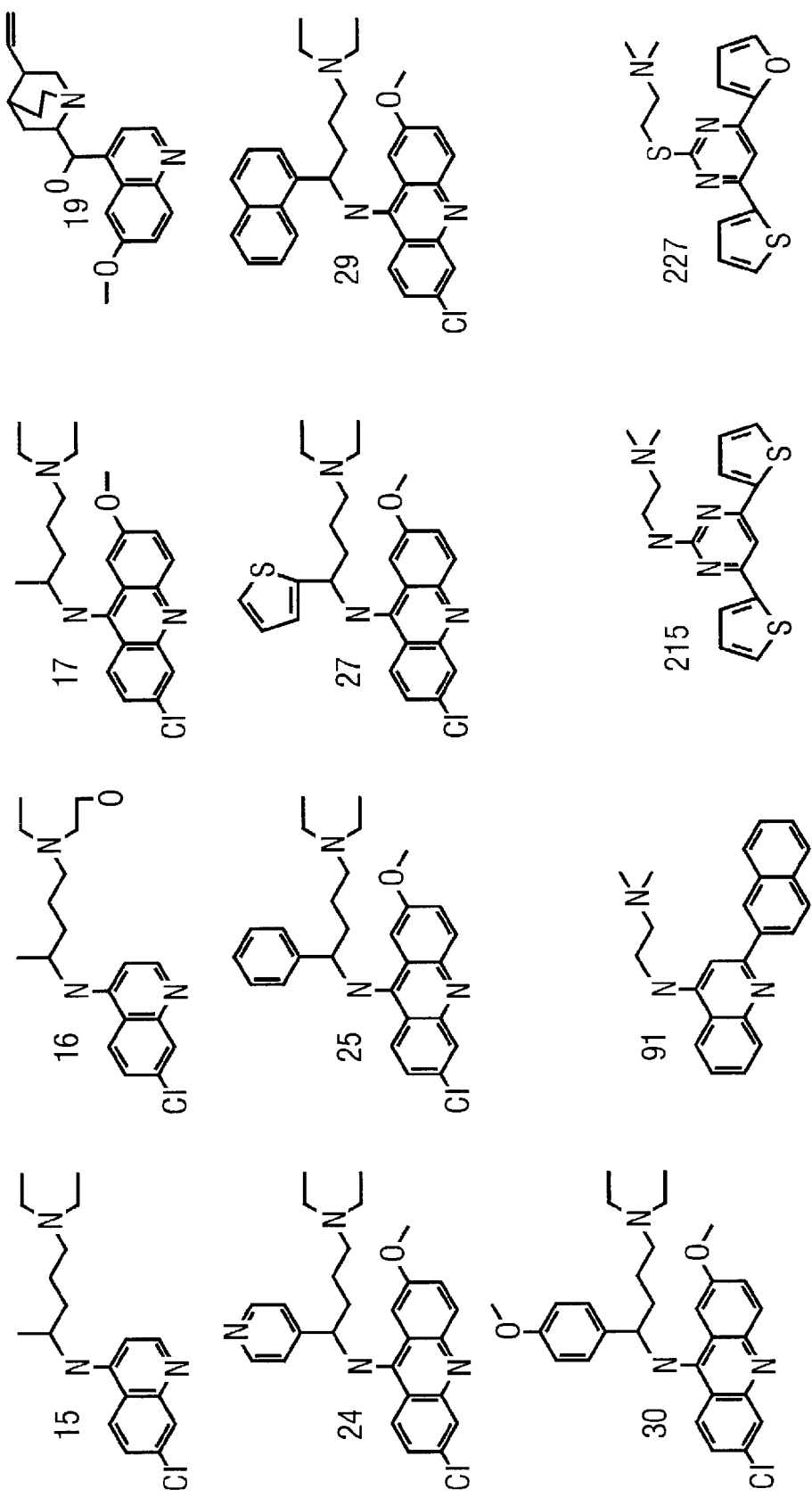
FIG. 2. Structures of analogs used. The numbers are those in the first column of Table 9.
Figure 2B:
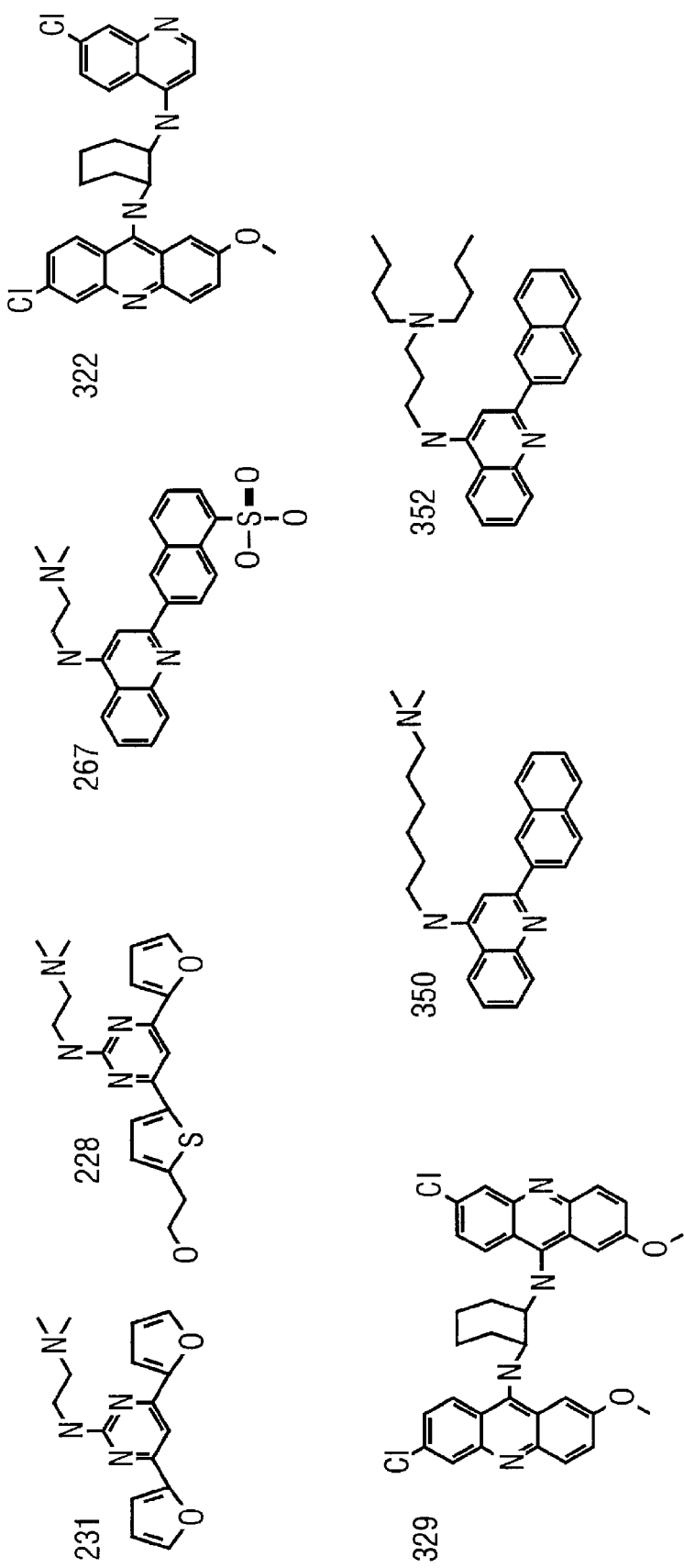

The ability of numerous novel analogs of chloroquine and quinacrine to block the activity of CpG-ODN was examined. From the library a number of compounds were seelcted that are fluorescent (including quinacrine) and that have a range of potency as inhibitors of CpG-ODN (FIG. 2, Table 10). Standard curves of the fluorescence intensity of each analog in cell culture medium and in the cell extract buffer were prepared, measurements being taken at the pH listed in the table. To examine the uptake of the analogs by cells, WEHI 231 cells were incubated with a range of concentrations of the analogs, and measured the concentration of the analog remaining in the supernatant and the amount of analog in the extract of a cell pellet using the standard curves.

Figure 3:
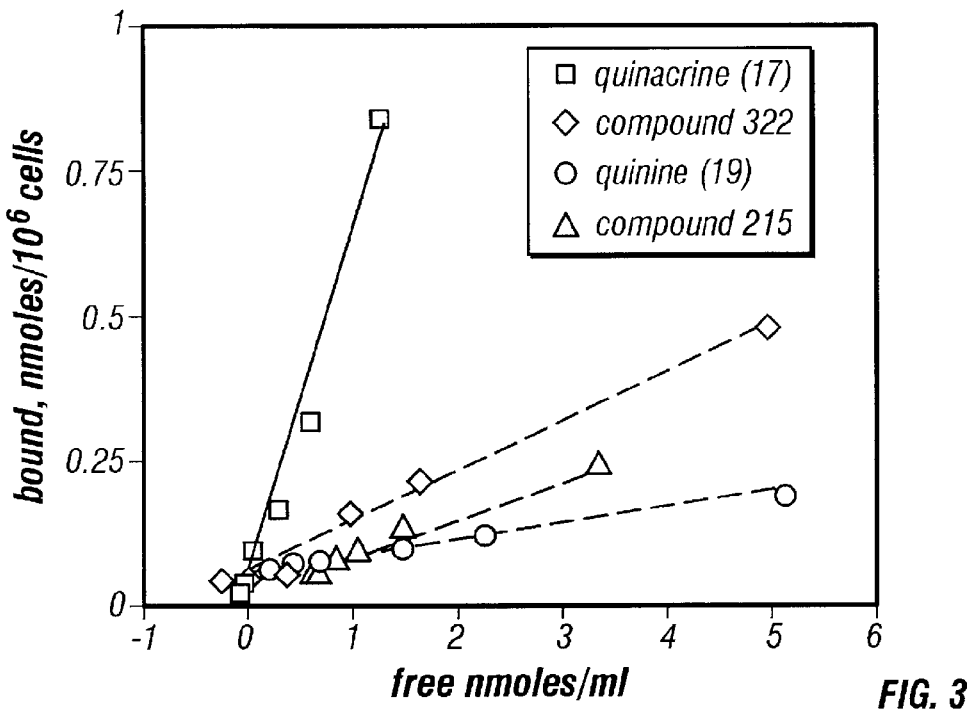
FIG. 3. Uptake of analogs by cells. WEHI 231 cells were incubated with fluorescent analogs (0.1–20 uM) for 30 min. The concentration of the analogs in the supernatant medium (free) and cellular pellet (bound) was then determined as described in Methods.

FIG. 3 shows some of the results. The cells incorporated substantial amounts of the analogs (often more than half of the added reagent). The volume of each cell is about 1.0 nl (by measuring the volume of a cell pellet). Using this value, it was estimated that the cells accumulated analogs to a concentration several hundred fold higher than in the medium (Table 10). Similar results have been reported for chloroquine e.g.(Ohkuma and Poole, 1981; Fitch et al., 1974). The inventors found a linear relationship between uptake of each of the compounds and its free concentration.

No evidence was found to suggest that the uptake process was saturable in the low micromolar range. It was found that (non-fluorescent) chloroquine (up to 10 uM) did not inhibit the uptake of other analogs, which also suggests that the transport mechanism is not saturable. This result with WEHI 231 cells differs from the uptake of chloroquine by red blood cells infected with malaria parasites, which others have reported to be saturable and inhibitable by analogs, suggesting that infected red cells have a high affinity transport system for chloroquine (Fitch et al., 1974).

Figure 4:
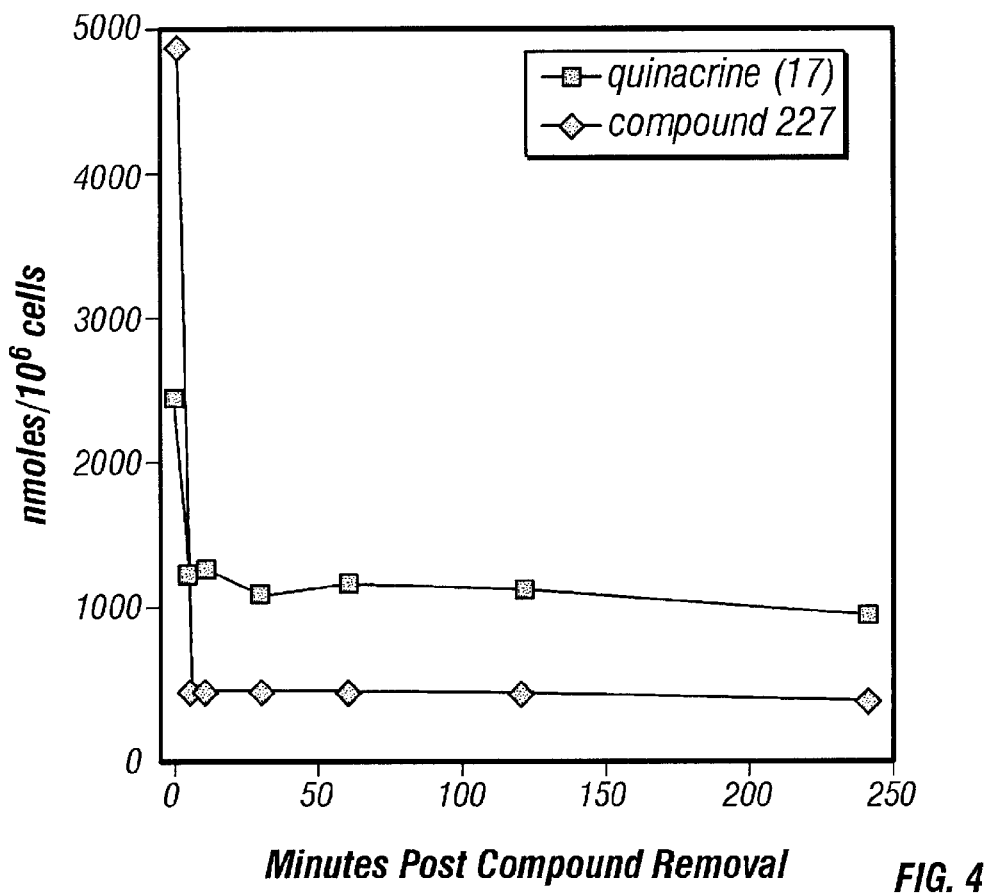
FIG. 4. Efflux of analog. WEHI 231 cells were incubated with 20 $\mu$M analog for 30 min. The cells were pelleted, resuspended in 15 ml medium, and incubated at 37° C. At the time indicated, the cellular concentration of the analog was determined by fluorescence. Note that the efflux of analog is rapid.

The uptake of the fluorescent analogs was rapid, reaching equilibrium in less than two minutes. The efflux analogs from cells when they are diluted into fresh medium was also rapid (FIG. 4).

Figure 5:
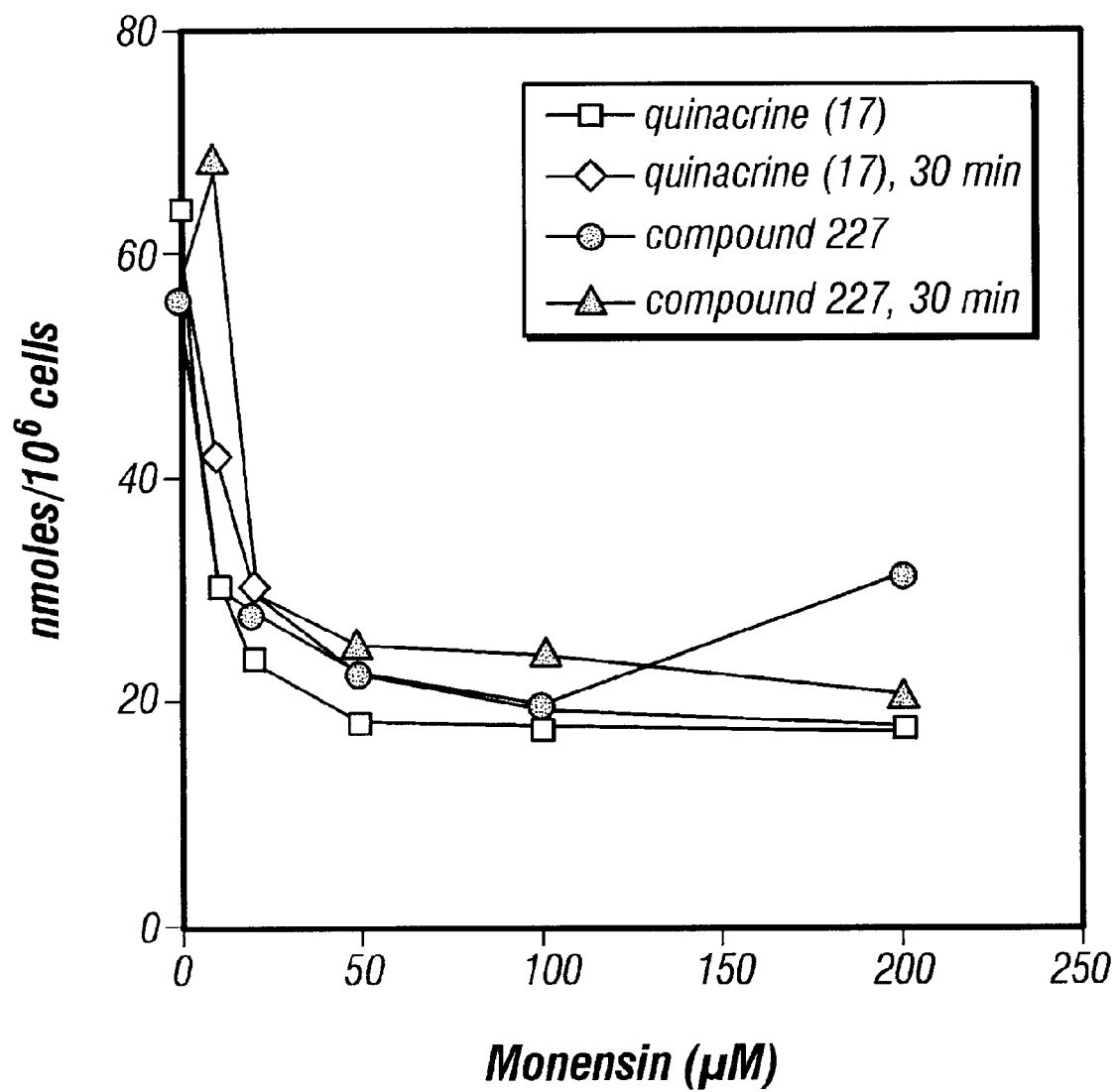
FIG. 5. Monensin: Cells were incubated with 1 uM quinacrine 17 or compound 227 for 30 min. Monensin at the indicated concentration was added either at the same time as the analog or at the end of the 30 min incubation, and the cellular concentration of the analog was determined by fluorescence.

The inventors found that uptake of quinacrine was partially inhibited by the addition of monensin, an ionophore that collapses pH gradients across biological membranes. Monensin also induced the loss of quinacrine 17 from cells preloaded with the analog. Both effects were half maximal at a monensin concentration of about 1 $\mu$M (FIG. 5). Similar results were obtained with other analogs. This result is consistent with equilibration of analogs (as weak bases) into acidic vesicles.

induced cell death. The cellular uptake ratio is the concentration of compound in live WEHI 231 cells (assumed to have a volume of 1 nl) to the concentration in the medium at equilibrium. The molecules at 50% efficacy is the calculated number of molecules in the cell required for 50% inhibition of CpG-ODN effect. ND, not determined.

Example 3
Comparison of Uptake and Activity

The ability of analogs to inhibit an immunostimulatory effect of CpG-ODN was examined. This assay measures the reversal of the protection by CpG-ODN against surface IgM induced killing of WEHI 231 cells. The activity of analogs was compared to their uptake, exposing a poor correlation between these two parameters (Table 10). At half maximal efficacy, cells accumulated a few million molecules of the most active analogs.

Example 4
Effect on CpG-ODN Uptake

The effect of chloroquine and non-fluorescent analogs on the uptake of Texas Red-labeled CpG-ODN 1760 was investigated. This derivatized ODN is active as an immune stimulator. Flow cytometry measures cell-associated fluo-

TABLE 10

| | | Analogs Used | | | |
|---|---|---|---|---|---|
| Our Number, source | Fluorescence vs quinacrine, pH | Name | 50% Efficacy, nM | Cellular uptake ratio | Molecules/cell at 50% efficacy |
| 329, d | 1.2, b | Ism 16 | 14.5 | 147 | 1.28 |
| 24, a | 0.7, n | 10591-T/2 | 30.2 | 161 | 2.92 |
| 17, a | 1.0, b | Quinacrine | 10.2 | 601 | 3.69 |
| 25, b | 0.7, a | 10593-V/2 | 19.1 | 438 | 5.03 |
| 322, d | 0.6, b | Ism 9 | 105.0 | 86 | 5.47 |
| 29, b | 1.7, n | 30020-N/2 | 57.5 | 164 | 5.69 |
| 30, b | 1.7, n | 74602-V/4 | 52.4 | 299 | 9.44 |
| 27, b | 3.3, a | 30018-L/1 | 60.3 | 583 | 21.1 |
| 19, a | 0.8, pH2.0 | Quinine | 23000 | 24 | 331.1 |
| 267, c | 2.2, a | OZ-66 | >3000 | 362 | >654 |
| 227, c | 1.4, n | MC-241 | >3000 | 63 | >115 |
| 228, c | 1.3, n | MC-132 | >3000 | 27 | >49 |
| 215, c | 0.7, a | RW-15 | >3000 | 70 | >126 |
| 231, c | 0.3, n | DH-77 | >3000 | 29 | >52 |
| 91, c | ND | LS-8 | 9.5 | ND | ND |
| 350, c | ND | OZ-123 | 5.9 | ND | ND |
| 352, c | ND | MHQ-6 | 16.3 | ND | ND |
| 15, a | Non-fluorescent | Chloroquine | 110.0.0 | ND | ND |
| 16, a | Non-fluorescent | Hydroxy-chloroquine | 407 | ND | ND |

Figure 6:
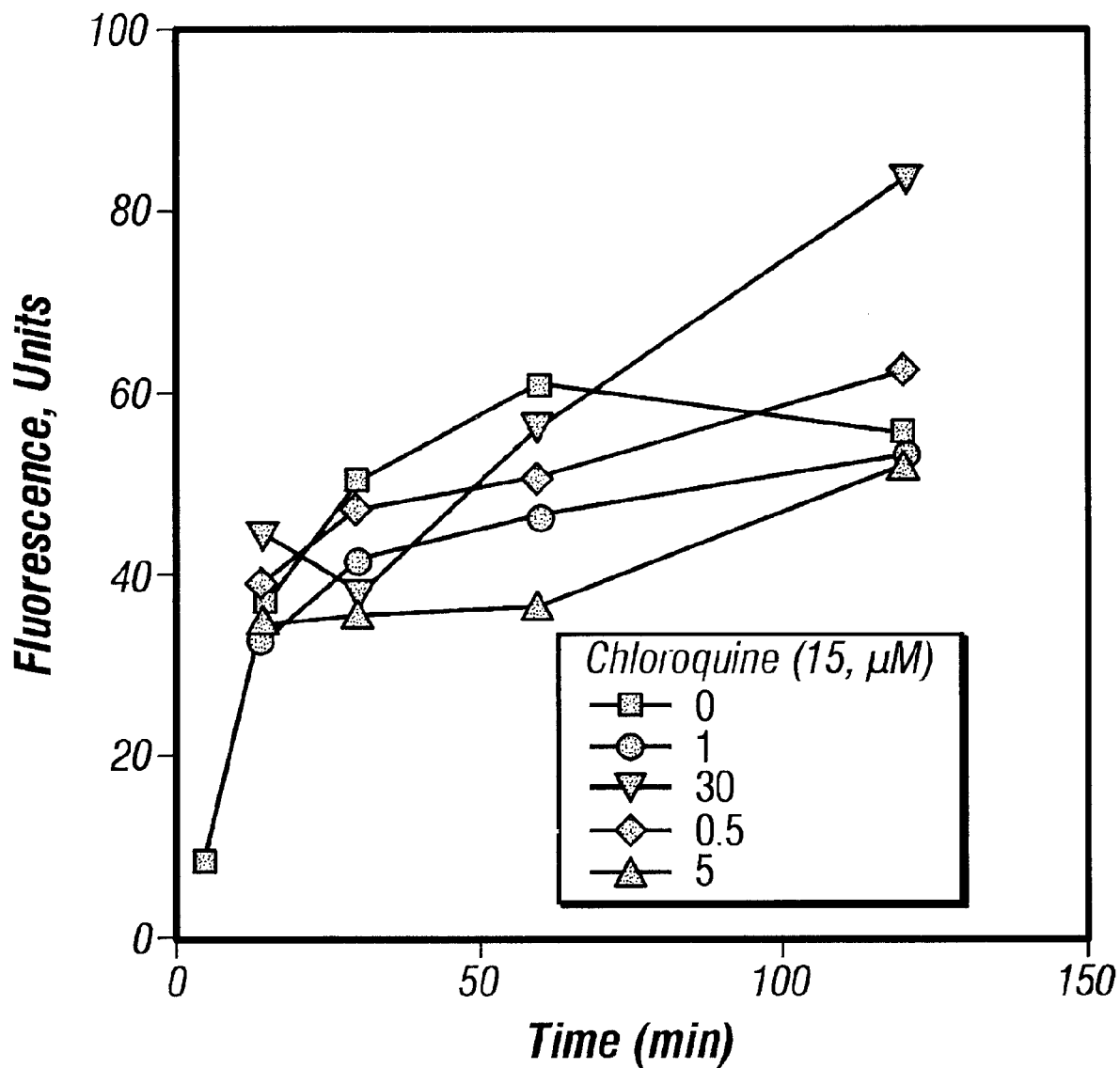
FIG. 6. Influence of chloroquine on CpG-ODN uptake: Cells were incubated with 5 ug/ml Texas Red CpG-ODN 1760 and indicated concentration of chloroquine 15 for the time indicated. The cells were then washed three times, and fixed. The cellular uptake of fluorescent CpG-ODN was estimated by flow cytometry. Note that chloroquine has no significant influence on CpG-ODN uptake.
Figure 7:
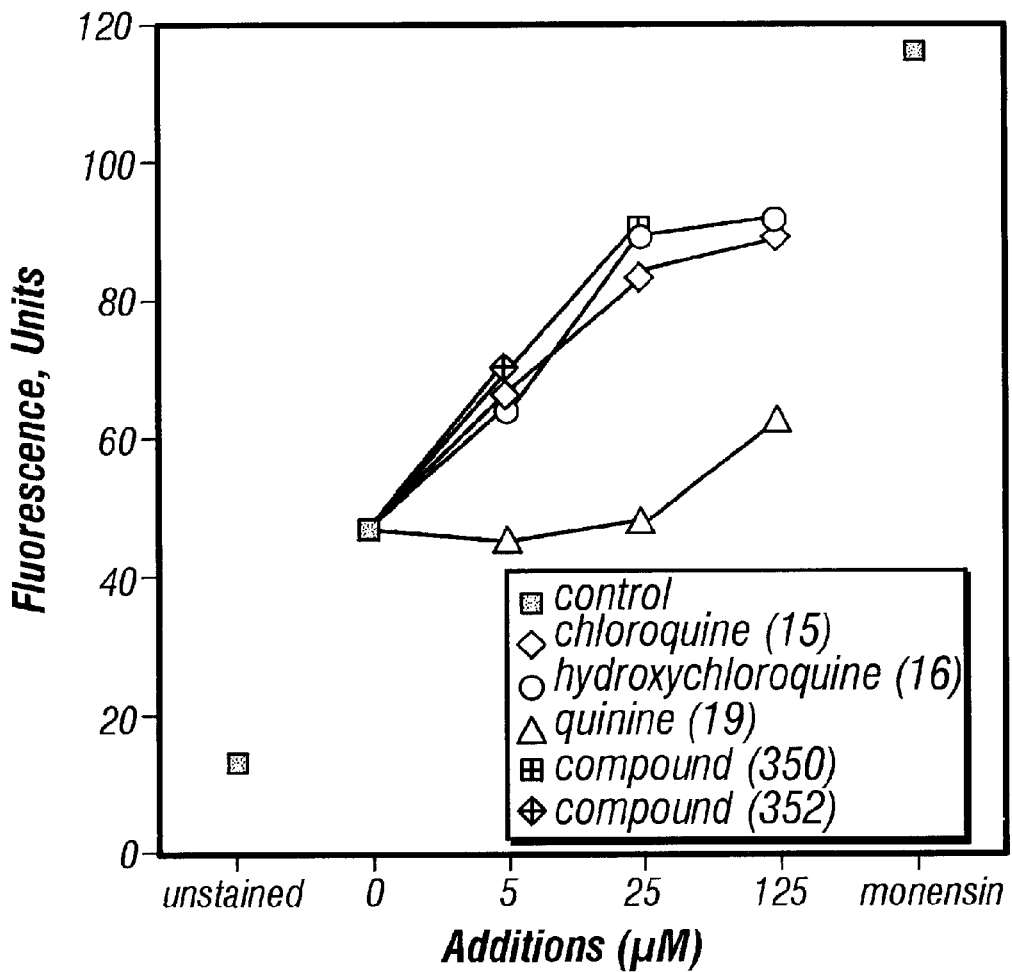
FIG. 7. pH of the ODN containing compartment: WEHI 231 cells were incubated with fluorescein-labeled CpG-ODN 1760. After washing the cells were resuspended, and either 20 $\mu$M monensin or analogs at the indicated concentration were added. 5–10 min later fluorescence was measured by flow cytometry. The change in fluorescence was converted to pH units by reference to a standard curve of fluorescence of fluorescein-labeled ODN 1760 as pH, shown on the righthand scale.
Figure 8:
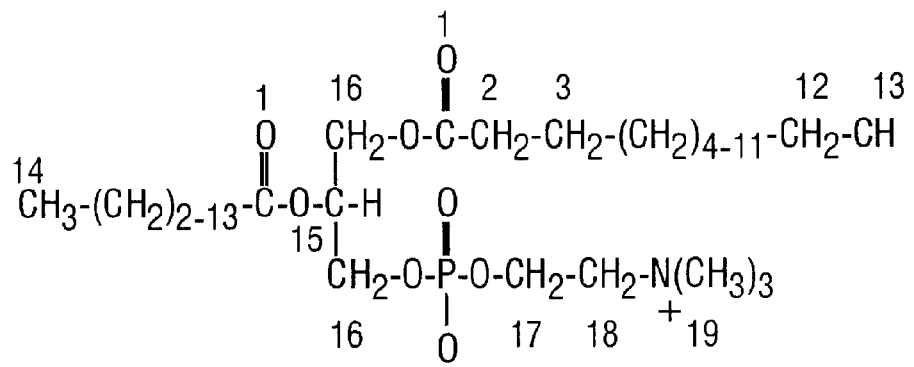
FIG. 8. Dimeristoylphosphatidylcholine, with number assignments used in Table 11 and FIG. 10.

The sources were a=Sigma Chemical Co., b=National Cancer Institute, c=Synthesized by LS, d=Synthesized by FMI. The second column is the fluorescence intensity (uncorrected) compared to quinacrine, recorded in a buffer at one of three pH's: a=3.8, n=7.4, b=10.0. The fluorescence of quinine was recorded at pH 2.0. The Efficacy is the concentration required for 50% blockage of the ability of CpG-ODN to rescue WEHI 231 cells from anti-surface IgMrescence because signals derived from dead cells (which take up ODN avidly, (Tonkinson and Stein, 1994)) are easily gated out of the analysis. The analogs did not significantly alter the uptake of the fluorescent ODN (FIG. 6).

Using confocal microscopy, the inventors determined that the fluorescence of Texas Red-labeled CpG-ODN 1760 is confined to numerous small organelles distributed throughout the cytoplasm with a slight predominance in the perinuclear region and Golgi apparatus. Chloroquine 15 did not influence the subcellular distribution of internalized CpG-ODN.

Example 5
Effect on CpG-ODN pH

The fluorescence of fluorescein is suppressed at acid pH. Cells preloaded with fluorescein-labeled CpG-ODN were used to determine the pH of cell-associated ODN using flow cytometry. The addition of monensin immediately before flow cytometry results in increased fluorescence, attributable to the equilibration of the pH of the ODN with the pH of the medium and the diluent used in flow cytometry.

A standard curve was implemented to relate fluorescence with pH, enabling the pH of the cell compartment occupied by ODN to be determined to be about 6.4, a value very close to that published by Tonkinson et al. using a similar method (Tonkinson and Stein, 1994). Using this method, the inventors examined the effects of (non-fluorescent) analogs on the pH of the compartment. The effect of 1 $\mu$M chloroquine (a concentration that completely suppresses CpG-ODN responses) was an increase in the pH of CpG-ODN-containing compartment by less than 0.01 pH units. No analog increased the pH substantially at the concentration required for activity, although they did collapse the pH at higher concentration.

Example 6
Subcellular Localization of Analogs

Next, the subcellular localization of fluorescent analogs was examined using confocal microscopy. Unable to find a method of fixation that immobilized the analogs within the cells, the inventors incubated the cells with the analogs and examined them live. A consistent difference between the distribution of CpG-ODN and of fluorescent analogs was revealed: the analogs occupy organelles that were larger and more peripherally located within the cell. However, it is not clear that quinacrine does not also enter the compartment occupied by CpG-ODN, because photographs of cells double-labeled with Texas-Red labeled CpG-ODN and quinacrine 17 did not unambiguously reveal a population of ODN-containing vesicles that also did not stain with quinacrine.

Example 7
Interaction Between Analogs and ODN

Structural nucleic acids with duplex or single-stranded folded conformations generally give sigmoid thermal melting curves characteristic of thermal unfolding of the structures. This unfolding results in a change in the UV spectrum. In other studies, the CpG ODN 1760 gave a very small continuous increase in absorbance at 260 nm as a function of temperature, characteristic of some base unstacking in single-stranded DNA, and did not show any transition curve characteristic of a base-paired structure. Addition of chloroquine 15 or quinacrine 17 to the CpG-ODN did not cause any significant change in the thermal melting curve of the free CpG-ODN. It can, thus, be concluded that under these conditions, these compounds bind poorly, if at all, to the CpG-ODN.

Example 8
Interaction Between Analogs and Lipids

The structures of compound 91 and DMPC are provided in FIG. 9; the lipid NMR resonance assignments that are listed in Table 11 are keyed to the numbered groups on the DMPC structure in this figure. The assignments in Table11 are derived in part from the work of Ellena et al., 1987 with additional assignments by the inventors.

TABLE 11

Proton resonance Chemical Shift Assignments for Compound 91 and DMPC in Unilamellar Vesicles

| Proton Number | Group | Chemical Shift, in $D_2O$, (ppm) |
| --- | --- | --- |
| 14 | —$CH_3$ | 0.87 |
| 13 | —$CH_2$— | 1.17 |
| 12 | —$CH_2$— | 1.25 |
| 4–11 | —$(CH_2)_{4-11}$— | 1.29 |
| 3 | —$CH_2$— | 1.56 |
| 2 | —$CH_2$— | 2.33 |
| 15 | CHOCO— | 5.26–5.31 |
| 16 | $H_2$COCO— | 4.43 |
| 16 | $H_2$COPO— (glyceride) | 3.99 |
| 17 | —OPOCH$_2$— (choline) | 4.27 |
| 18 | —$CH_2$N— | 3.56–3.63 |
| 19 | $N(CH_3)_3$ | 3.12–3.19 |
| Compound 91 | Naphthalene, quinoline | 7–9 |

Figure 9A:
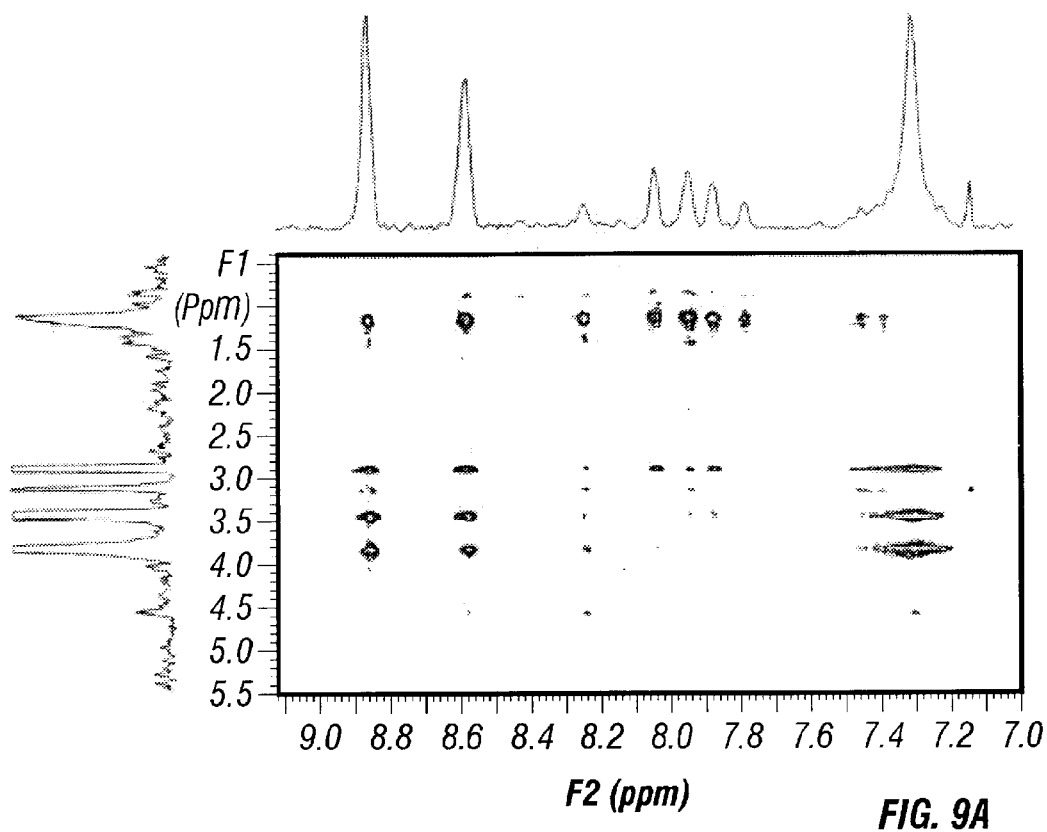
FIG. 9A. NOESY spectra of compound 91 bound to phosphatidylcholine vesicles.
Figure 9B:
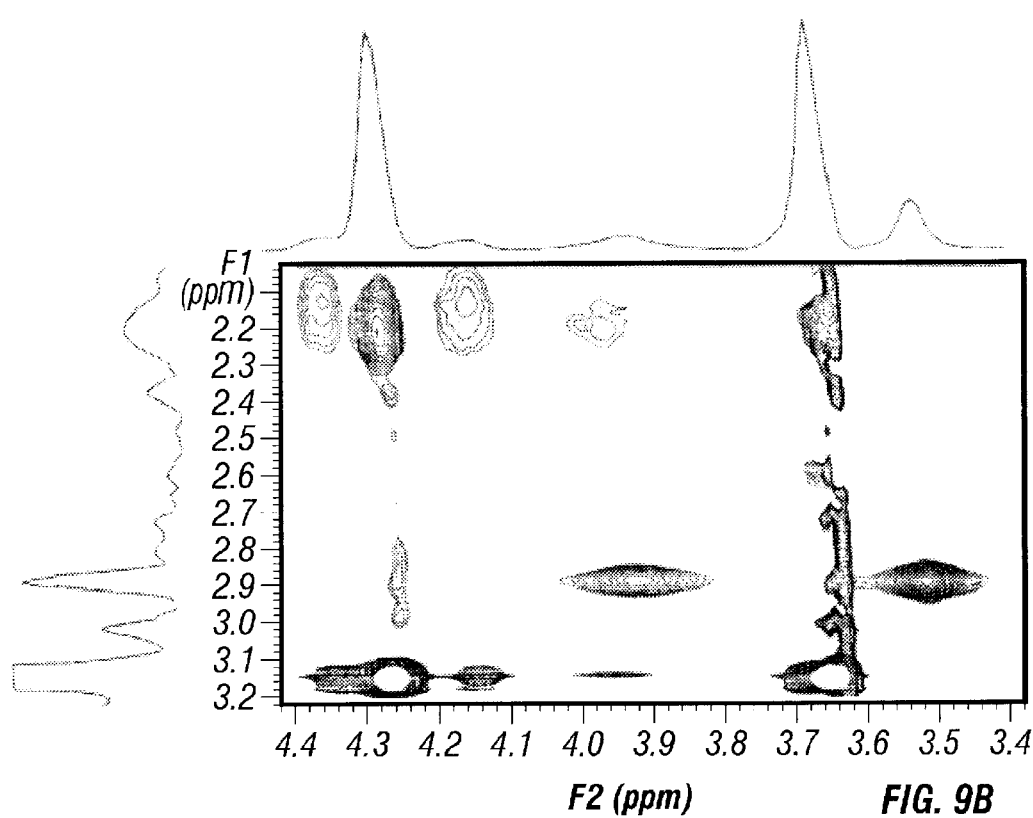
FIG. 9B. Aliphatic region of the same spectra. See Table 11 for assignments, and text for details and interpretation.
Figure 10A:
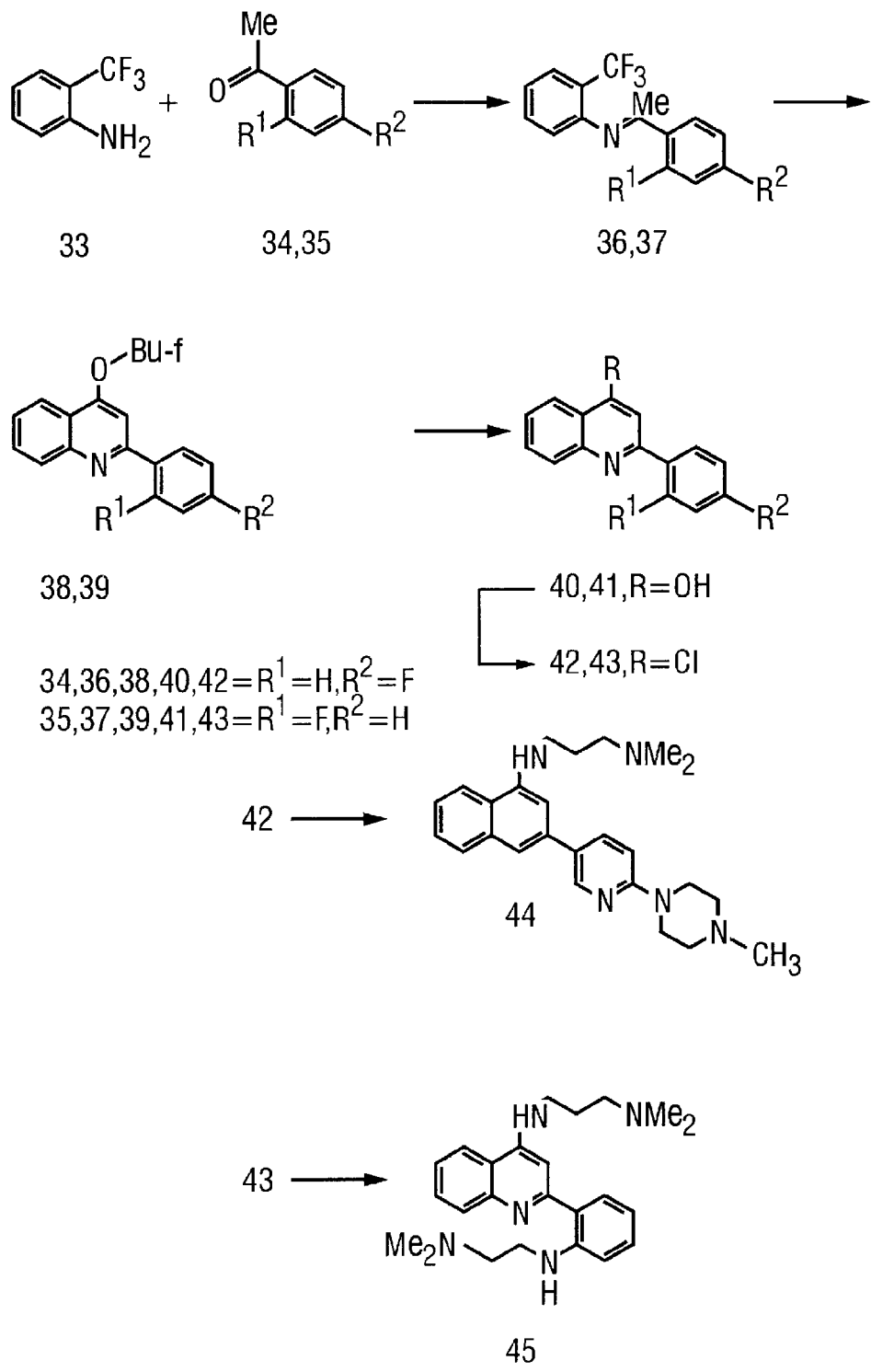
Figure 10B:
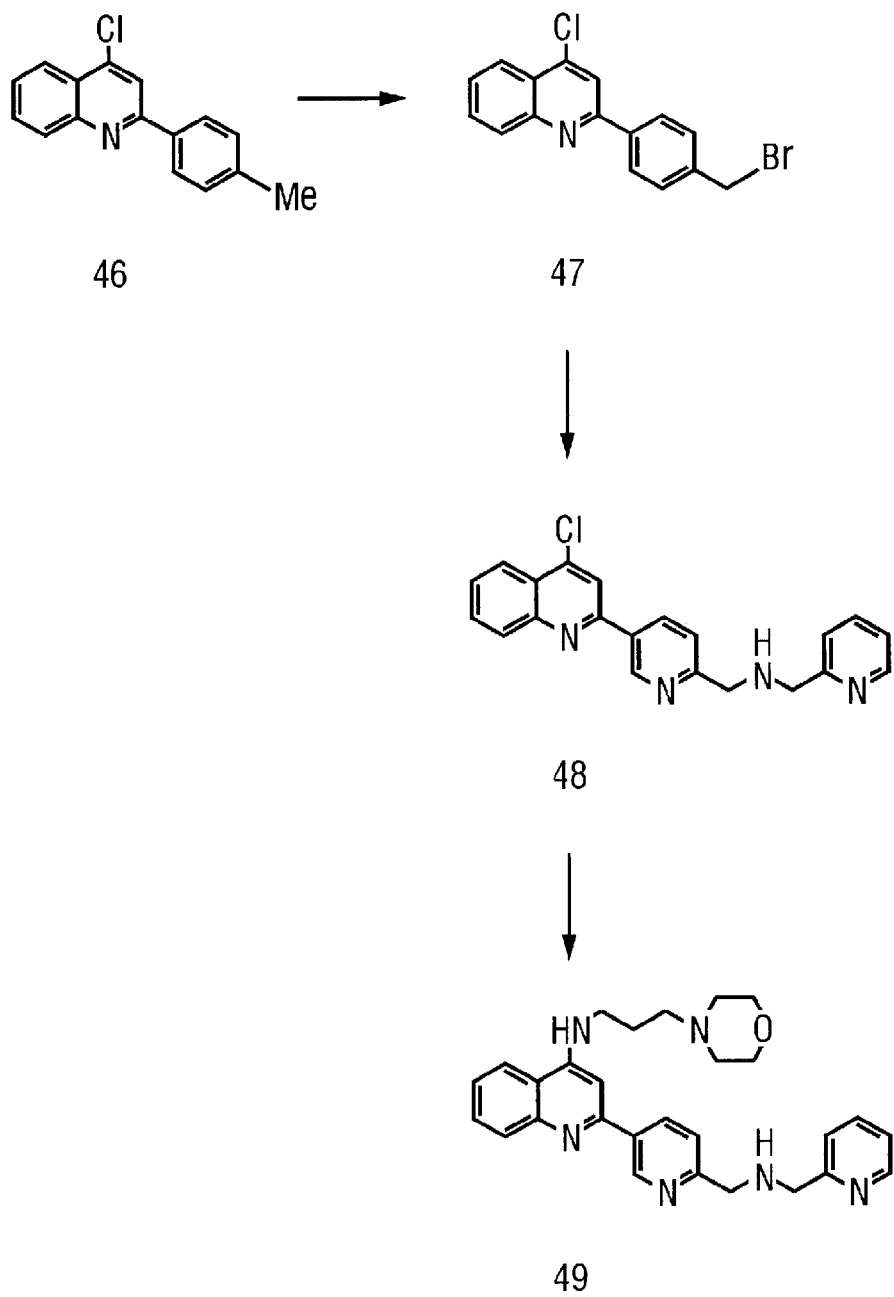

A typical spectrum obtained at a pH of 7. is shown in FIG. 9 and is referenced to the terminal methyl resonance of the DMPC acyl chain (0.87 ppm); this assignment is relative to an external TMS standard. NOESY cross peaks between the compound 91 quinoline and naphthalene ring protons and those of the DMPC fatty acid unresolved methylenes (1.3 ppm on the F1 axis, Nos. 4–11; FIG. 9A) are present. Additional cross peaks are observed between the compound 91 aromatic ring protons and those of the lipid glycerol backbone methylenes (3.99 ppm, No. 16) and to those of the choline N-$CH_2$ moiety (3.5 ppm, No. 18). Very weak, marginal cross peaks are observed between the compound 91 aromatic system protons and those of the choline $N(CH_3)_3$ moiety (3.2 ppm, No. 19) and to those of the fatty acid terminal methyl group at 0.87 ppm on the F1 axis (No. 14, FIG. 9A). The NOESY spectrum obtained at a pD of 4.7 is qualitatively similar to that obtained at a pD of 7.4. In the aliphatic region, the cross peak at 4.25 ppm on the F2 axis is assigned to the interaction of the compound 350 aliphatic chain methylene groups with those of the OPO-$CH_2$ methylene (No. 17) (FIG. 9B).

A location model that is consistent with the NOESY data suggests that the charged $N(CH_3)_2$ moiety be located no deeper in the membrane bilayer than the onset of the hydrocarbon region—near the ester linkages in the DMPC lipids. The NOESY results indicate that the aliphatic chain of compound 91 is located near the interface of the choline head group and the glycerol backbone of the lipid. Such a location would allow for favorable electrostatic interactions between the protonated $N(CH_3)_2$ group and the negatively charged DMPC phosphate moiety.

The unambiguous cross peaks between the aromatic ring protons of compound 91 and the unresolved DMPC fatty acid methylene protons (1.3 ppm on the F1 axis) indicates that a portion of the compound 91 molecules penetrate the bilayer to at least the level of the fourth methylene group on the fatty acid chain and perhaps below this level.

Molecular modeling studies using SYBYL (Tripos Associates) of a DMPC bilayer with the lipids in the all trans conformation and with compound 91 in an energy minimized extended conformation with the protonated $N(CH_3)_2$ nitrogen located near the phosphate group will allow an NOE cross peak between protons on the naphthalene ring and the No. 8 methylene protons with a 5 Å NOE cutoff distance criterion.

The lack of cross peaks between the terminal methyl group and the aromatic protons does not preclude the eventual translocation of compound 91 through the bilayer and the accumulation of the drug candidate in the vesicle internal volume as has been observed in whole cell studies based on similar quinolines tagged with fluorescent labels as described in a separate section of this communication. The NMR results suggest in this instance that the steady state population of compound 91 molecules near the middle portion of the bilayer, which would include the roughly 0.5 mol percent of compound 91 in neutral form, is below the detection threshold for the NOESY experiment in the DMPC vesicle system.

Example 9
Preparation of 2-(Substituted phenyl)-4-quinolinamines

N-[3-(Dimethylamino)propyl]-2-[4-(N-methylpiperazino)phenyl]quinolin-4-amine (44)

A ketimine 36 derived from 33 and 34 was cyclized to a quinoline 38 in the presence of potassium tert-butoxide by using a procedure for the preparation of similar compounds (Strekowski et al., 1997). Hydrolysis of 38 in the presence of acid followed by treatment of the resultant hydroxyquinoline 40 with POCl$_3$ gave a chloroquinoline 42. The general procedures are also described in the same reference. The selective displacement of the chlorine atom in 42 was accomplished by treatment with N,N-dimethyl-1,3-propanediamine in the presence of a catalytic amount of SnCl$_4$ (4 h, 130° C.). Stirring of the resultant product (1 mmol) with lithium N-methylpiperizide (20 mmol) in anhydrous THF (50 mL) at 23° C. for 20 h followed by quenching with water gave compound 44 that was purified by silica gel chromatography eluting with EtOAc/NEt$_3$ (17:3): yield 61%, mp of the hydrobromide salt (x3HBr) 274–276° C.

N-[3-(Dimethylamino)propyl]-2-[2-[[2-(dimethylamino)ethyl]amino]-phenyl]quinolin-4-amine (45)

A ketimine 37 was obtained from 33 and 35 as indicated above. Its cyclization to 39, hydrolysis of 39 to 41, and the synthesis of 43 were carried out as described above as well. Following the treatment of 43 with N,N-dimethyl-1,3-propanediamine the resultant product was allowed to react with excess lithium 2-(dimethylamino)ethylamide in THF at 23° C. for 20 h. Product 45 was purified by silica gel chromatography eluting with EtOAc/Et$_3$N (25:1): yield 76%, a solid.

N-(3-Morpholinopropyl)-2-[4-[[2-pyridyl)methylamino]methyl]phenyl]-quinoline (49)

Synthesis of 4-chloro-2-(4-tolyl)quinoline (46) was conducted by using the chemistry described above. The treatment of 46 (5 mmol) with N-bromosuccinimide (5 mmol) in the presence of benzoyl peroxide (100 mg) in CCl$_4$ (50 mL) under reflux for 6 h gave 47: yield 63%, mp 116–117° C. (from hexanes). A mixture of 47 (0.6 mmol) and 2-(aminomethyl)pyridine (2 mL) was stirred at 23° C. for 6 h and then treated with water (20 mL). Extraction with ethyl acetate followed by drying of the extract and concentration gave compound 48 that was used for the reaction with 3-morpholinopropylamine without any purification. A mixture of 48, the amine (1 mL), and a catalytic amount of SnCl$_4$ was heated under reflux for 4 h and then quenched with water (20 mL). Following a standard workup, crude product 49 was purified by silica gel chromatography eluting with EtOAc/MeOH/Et$_3$N (10:1:3): yield 58%, mp 140–142° C.

Example 10
Preparation of Substituted 4-Quinolinamines and 9-Aminoacridines

Figure 11:
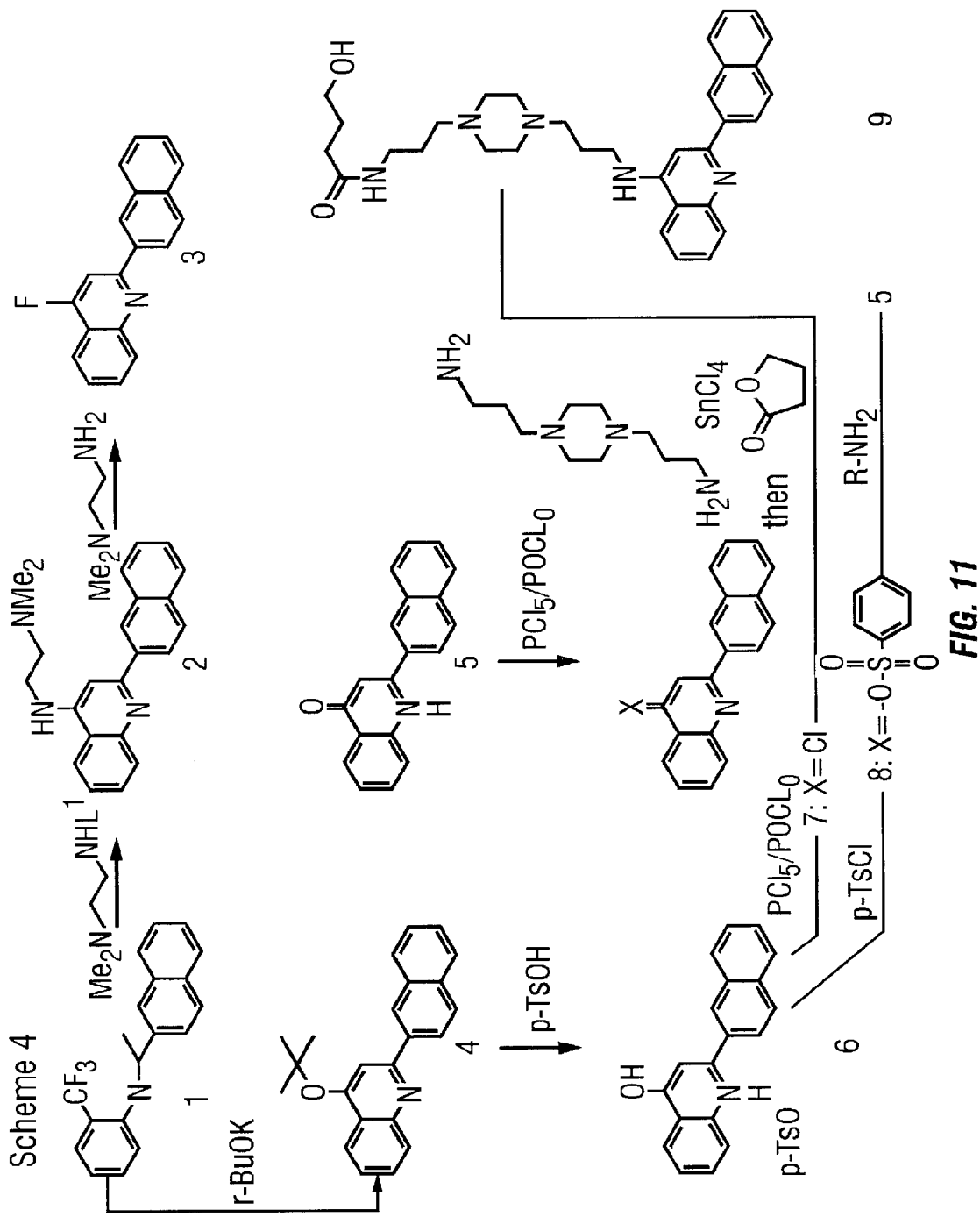
FIG. 11. Scheme 4 as described in Example 10.
Figure 12A:
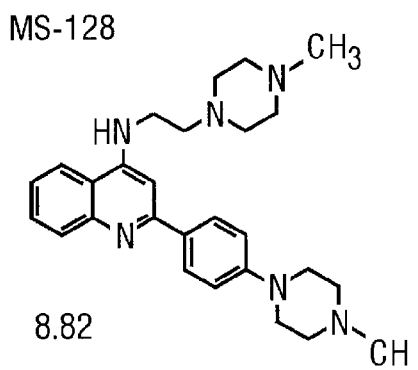
FIGS. 12A–E. Additional analogs with some inhibitory activity against CpG ODN immunostimulation. The level of activity is presented for each compound, and the compounds are generally presented in order of decreasing activity.
Figure 12A:
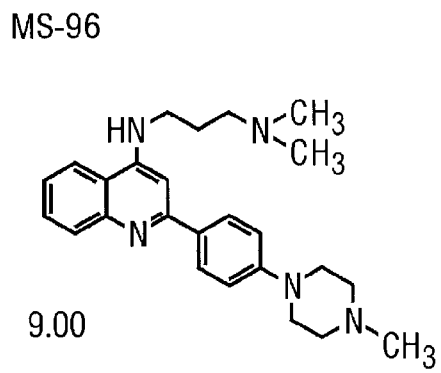
Figure 12A:
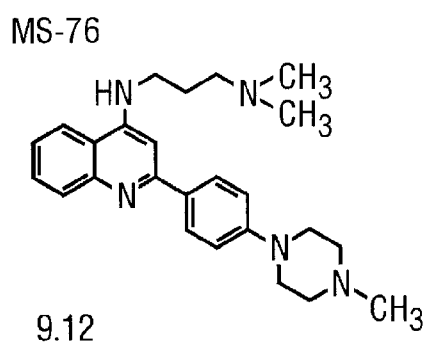
Figure 12A:
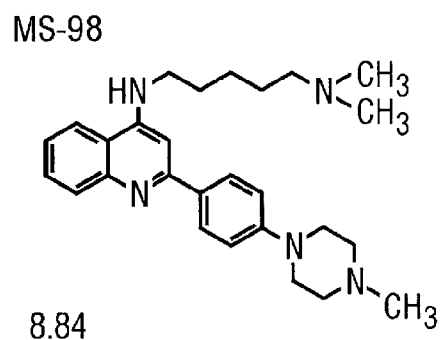
Figure 12A:
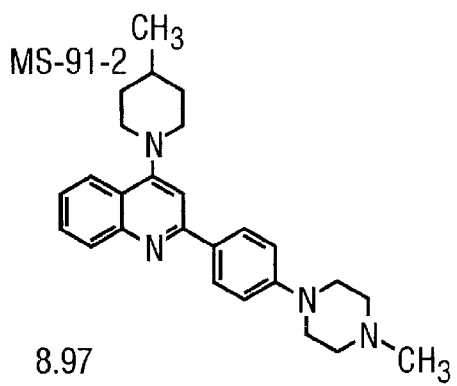
Figure 12A:
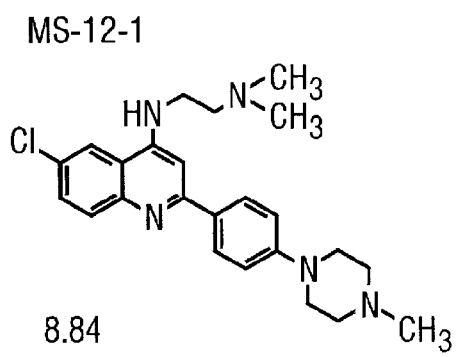
Figure 12A:
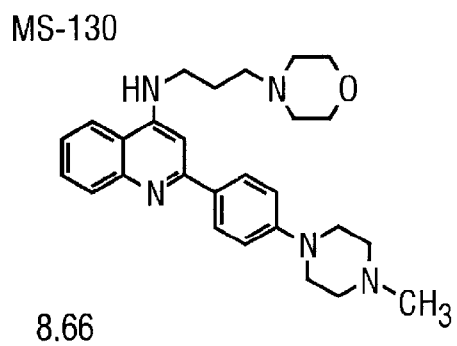
Figure 12A:
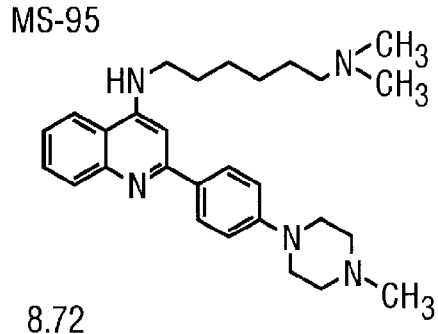
Figure 12B:
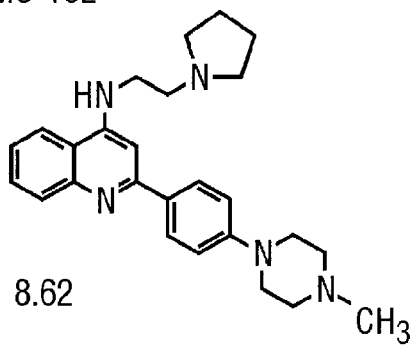
Figure 12B:
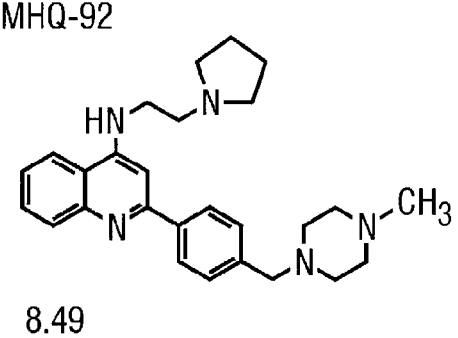
Figure 12B:
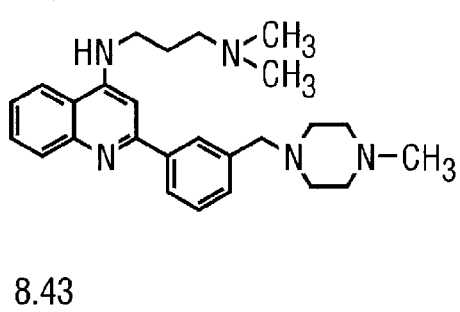
Figure 12B:
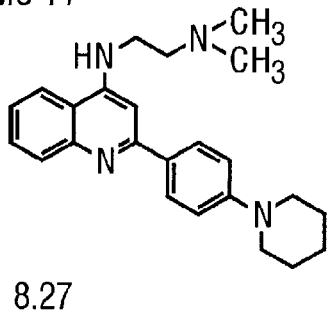
Figure 12B:
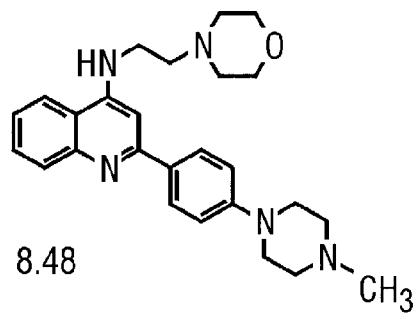
Figure 12B:
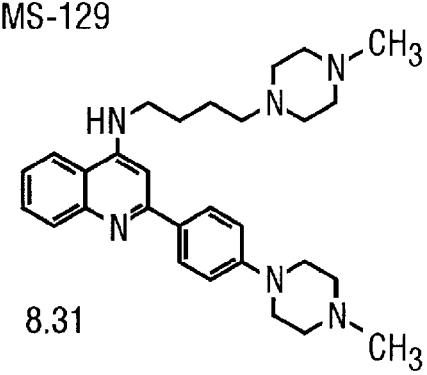
Figure 12B:
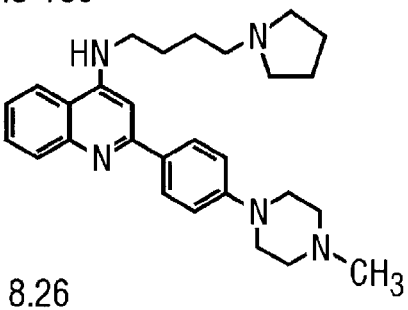
Figure 12C:
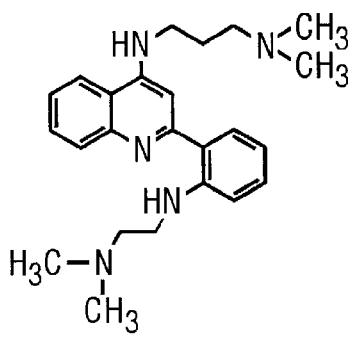
Figure 12C:
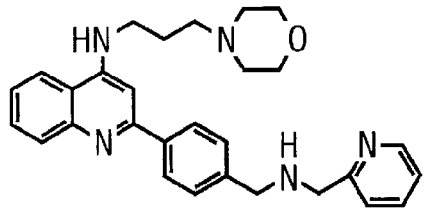
Figure 12C:
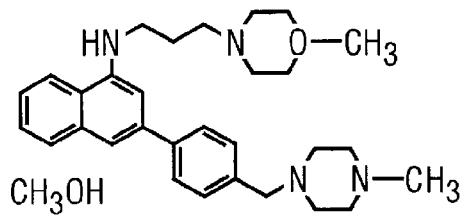
Figure 12C:
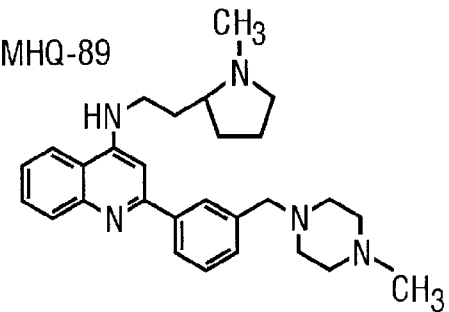
Figure 12C:
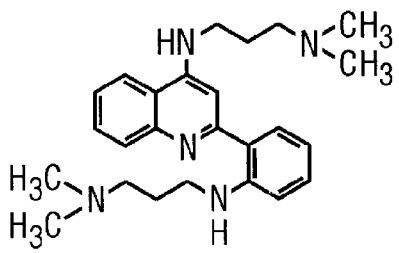
Figure 12C:
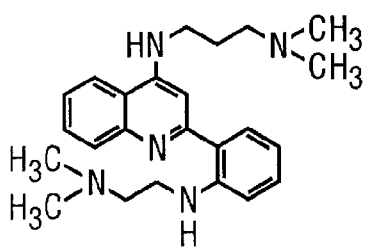
Figure 12C:
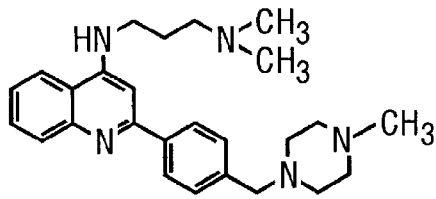
Figure 12C:
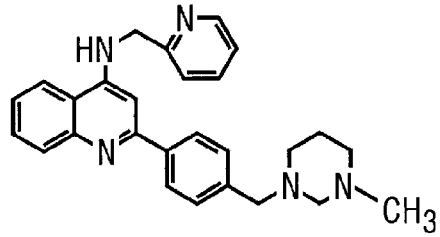
Figure 12D:
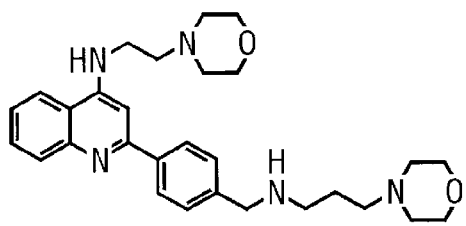
Figure 12D:
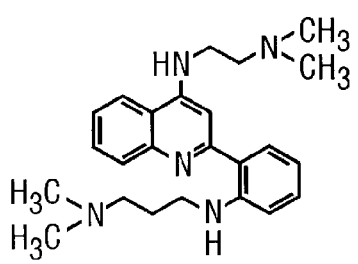
Figure 12D:
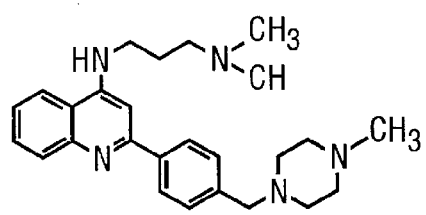
Figure 12D:
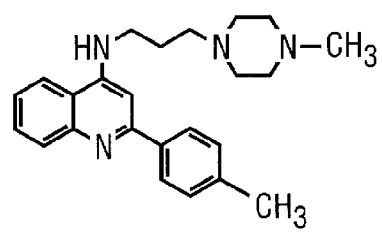
Figure 12D:
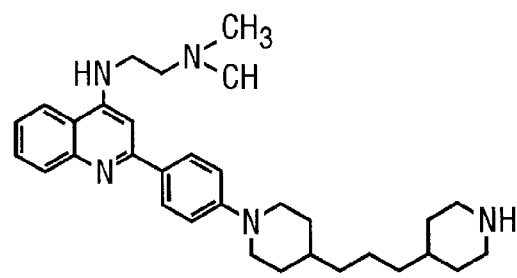
Figure 12D:
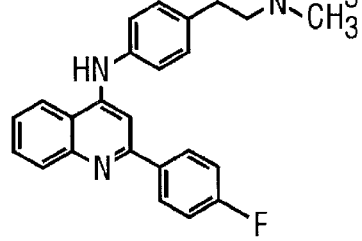
Figure 12D:
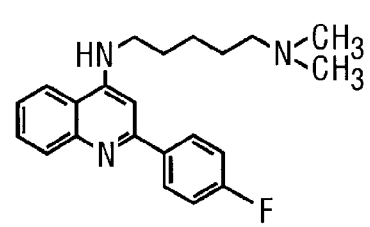
Figure 12D:
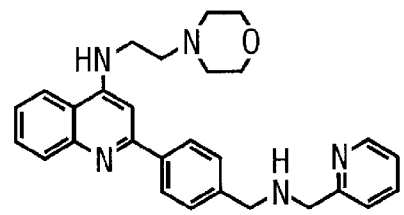
Figure 12E:
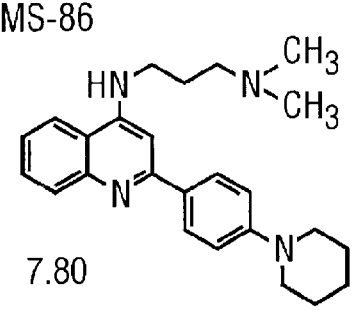
Figure 12E:
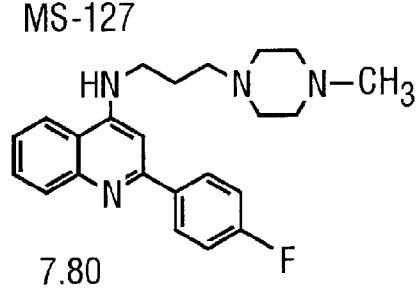
Figure 12E:
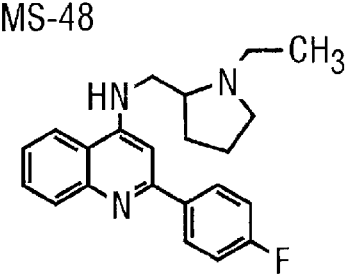
Figure 12E:
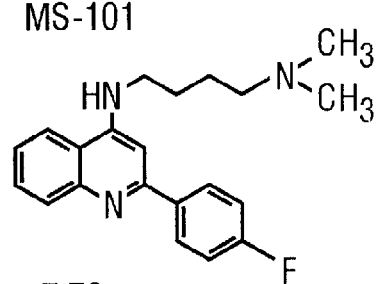

Compounds have been numbered in this example. This numbering refers only to the compounds found in this example and in Scheme 4 shown in FIG. 11, which corresponds to this example.

Materials and Methods

Melting points (Pyrex capillary) are uncorrected. $^1$H NMR (300 MHz) and $^{13}$C NMR (75.4 MHz) spectra were taken with TMS as an internal reference. Proton-proton coupling constants smaller than 2 Hz are not reported. Ketimine 1 was obtained as reported previously (Strekowski et al., 1992).

Reaction of Ketimine 1 with Potassium tert-Butoxide.

A mixture of 1 (10 g, 32 mmol) and t-BuOK (17 g, 150 mmol) in anhydrous THF (500 mL) was heated under reflux under a nitrogen atmosphere for 1 h. Cooling to 23° C. was followed by quenching with water (6.0 mL) and filtration. Concentration of the filtrate on a rotary evaporator to 50 mL followed by dilution with hexanes (40 mL) gave a precipitate of 5, which was filtered off and crystallized from methanol. Flash chromatography of the THF/hexanes solution (silica gel; hexanes/Et$_3$N, 95:5) gave an analytically pure sample of compound 4, which was additionally purified by crystallization from hexanes. Crude compound 4 was used for the subsequent reaction.

4-(tert-butoxy)-2-(2-naphthyl)quinoline (4)

1.06 g (51%); mp 76–78° C.; $^1$H NMR (CDCl$_3$) δ1.64 (s, 9 H), 7.19 (s, 1 H), 7.41 (t, J=8 Hz, 1 H), 7.46 (m, 3 H), 7.63 (t, J=8 Hz, 1 H), 7.83 (m, 1 H), 7.93 (m, 2 H), 8.06 (d, J=8 Hz, 1 H), 8.14 (d, J=8 Hz, 1 H), 8.19 (d, J=8 Hz, 1 H), 8.45 (s, 1 H); $^{13}$C NMR (CDCl$_3$) δ28.9, 80.7, 105.1, 122.6, 123.2, 125.2, 125.3, 126.3, 1256.6, 126.9, 127.7, 128.5, 128.8, 12802, 129.8, 133.4, 133.7, 137.8, 149.8, 158.1, 160.1, Anal. Calcd for C$_{23}$H$_{2e1}$NO: C, 84.39; H, 6.46; N, 4.28. Found C, 84–39; H, 6.59, N, 4.45.

2-(2-naphthyl)quinolin-4(1H)-one (5): yield 1.3 G (15%); mp 290–292° C. (from MeOH); $^1$H NMR (DMSO-d$_6$) δ3.13 (br s, 1 H), 6.48 (s, 1 H), 7.35 (t, J=8 Hz, 1H), 7.63 (m, 2 H), 7.69 (t, J=8 Hz, 1H), 7.81 (d, J=8 Hz, 1 H), 7.93 (d, J=8 Hz, 1 H), 8.03 (m, 1 H), 8.11 (m, 2 H), 8.46 (s, 1 H); $^{13}$C NMR (DMSO-d$_6$) δ107.8, 118.7, 123.3, 124.5, 124.8, 124.9, 127.0, 127.2, 127.5, 127.7, 128.6, 128.7, 131.5, 131.9, 132.6, 133.6, 140.6, 149.9, 176.9; IR (KBr) v 3250, 1630, 1595, 1547, 1508 cm$^{-1}$. Anal. Calcd for C$_{19}$H$_{13}$NO: C, 84.11; H, 4.83; N, 5.16. Found: C, 83.80; H, 4.69; N, 5.14.

4-Hydroxy-2-(2-naphthyl)quinolinium p-toluenesulfonate (6)

A solution of crude compound 4 (6.5 g, 20 mmol) and p-toluenesulfonic acid (6.0 g, 30 mmol) in THF (150 mL) was heated under reflux for 4 h and then cooled to 0° C., the precipitate of 6 was filtered off and crystallized from methanol: yield 8.0 g (93%); mp 223–225° C.; $^1$H NMR (DMSO-d$_6$) δ2.28 (s, 3), 7.10 (d, J=8 Hz, 2 H), 7.28 (s, 1 H), 7.50 (d, J=8 Hz, 2 H), 7.71 (m, 3 H), 8.0–8.215 (m, 6 H), 8.33 (d, J=8 Hz, 1 H), 8.61 (s, 1 H). Anal. Calcd for C$_{26}$H$_{21}$NO$_4$S: C, 70.40; H, 4.77; N, 3.16. Found: C, 70.38; H, 4.73; N, 3.11.

4-Chloro-2-(2-naphthyl)quinoline (7)

A mixture of salt 6 (7.0 g, 15.7 mmol), phosphorus pentachloride (3.2 g, 15.7 mmol), and phosphorus oxychloride (40 mL) was heated under reflux for 1 h, then cooled, and poured onto ice. The mixture was neutralized with a saturated solution of sodium bicarbonate, and the resultant precipitate of crude product 7 was filtered, washed with water, and dried (50° C./10 mmHg). Purification involved treatment with hot ethyl acetate (180 mL), filtration from an insoluble yellow solid, then concentration of the solution, and crystallization of the residue from hexanes: yield 3.98 g (86%); mp 114–116° C.; $^1$H NMR (CDCl$_3$) δ7.48 (m, 2 H), 7.58 (t, J=8 Hz, 1 H), 7.74 (t, J=8 Hz, 1 H), 7.84 (m, 1 H), 7.94 (m, 2 H), 8.08 (s 1 H), 8.17 (m, 2 H), 8.28 (d, J=8 Hz, 1 H), 8.53 (s, 1 H); $^{13}$C NMR (CDCl$_3$) δ119.5, 124.3, 125.0, 125.7, 126.8, 127.3, 127.6 (two signals), 128.0, 129.0, 129.2, 130.4, 130.9, 133.7, 134.4, 136.1, 143.5, 149.4, 157.3. Anal. Calcd for C$_{19}$H$_{12}$ClN: C, 78.75; H, 4.17; N, 4.71. Found: 78.75; H, 4.11; N, 4.65.

The treatment of quinoline 5 as described above furnished product 7 in a similar yield.

2-(2-Naphthyl)-4-[(p-tolylsulfonyl)oxy]quinoline (8)

A solution of salt 6 (4.3 g, 10 mmol) in pyridine (60 mL) was cooled to 0° C. and treated slowly with p-toluensesulfonyl chloride (3.4 g, 18 mmol) at such a rate that the temperature did not rise above 5° C. After being stirred for an additional 3 h at 5° C., the mixture was diluted with dichloromethane (40 mL) and poured into cold water (200 mL). The organic layer was washed in succession with 1 N hydrochloric acid, a solution of sodium bicarbonate, and water, then dried over sodium sulfate, and concentrated on a rotary evaporator. Chromatography on silica gel eluting with hexanes/tert-butyl methyl ether (1:1) followed by crystallization from tert-butyl methyl ether gave 3.5 g (79%) of 8 mp 128–130° C.; $^1$H NMR (DMSO-d$_6$) δ2.43 (s, 3 H), 7.51 (d, J=8 Hz, 2 H), 7.62 (m, 3 H), 7.86 (d, J=8 Hz, 2 H), 7.96 (m, 3 H), 8.02 (m, 1 H), 8.13 (m, 3 H), 8.34 (d, J=8 Hz, 1 H), 8.65 (s, 1 H); $^{13}$C NMR (CDCl$_3$) δ21.7, 110.5, 121.2, 121.4h, 124.7, 126.5, 126.9, 127.0, 127.2, 127.7, 128.6, 128.7, 128.8, 129.5, 130.1, 130.6, 132.2, 133.3, 134.0, 136., 146.1, 150.1, 153.8, 157.8. Anal. Calcd for C$_{26}$H$_{19}$NO$_3$S: C, 73.39; H, 4.50; N, 3.29. Found:, 73.12; H, 4.32; N, 3.27.

N-[3-[4-[3-(4-Hydroxybutyramido)propyl]piperazino]-propyl]-2-(2-naphthyl)quinolin4-amine (9)

A mixture of 7 (5.0 g, 17 mmol), 1,4-bis(3-aminopropyl)piperazine (58 mL, 282 mmol), and anhydrous tin tetrachloride (0.8 mL, 6.6 mmol) was stirred and heated to 130° C. under a nitrogen atmosphere for 3.5 h. Removal of the excess of the amine (100° C./0.2 mmHg) was followed by addition of γ-butyro-lactone (3 mL, 39 mmol) and stirring of the mixture at 80° C. for an additional 2.5 h. After cooling to 23° C., water (10 mL) was added and the resultant solution was extracted with ethyl acetate (6×30 mL). The extract was dried over magnesium sulfate and concentrated, and the residue was crystallized from anhydrous ethyl acetate: yield 5.1 g (56%); mp 177–179° C.; $^1$H NMR (DMSO-d$_6$) δ1.5–3.5 (m, 26 H), 4.42 (t, J=5 Hz, 1 H, exchangeable with D$_2$O), 7.14 (s, 1 H), 7.38 (br, 1 H, exchangeable with D$_2$O), 7.42 (t, J=8 Hz, 1 H), 7.55 (m, 2 H), 7.65 (t, J=8 Hz, 1 H), 7.73 (br, 1 H, exchangeable with D$_2$O), 7.91 (d, J=8 Hz, 1 H), 7.96 (m, 1 H), 8.02 (d, J=8 Hz, 1 H), 8.09 (m, 1 H), 8.21 (d, J=8 Hz, 1 H), 8.39 (d, J=8 Hz, 1 H), 8.70 (s, 1 H); $^{13}$C NMR (DMSO-d$_6$) δ24.9 26.3, 28.6, 32.1, 36.8, 41.3, 52.7, 53.0, 55.5, 56.1, 60.3, 95.1, 118.0, 121.4, 123.7, 125.0, 126.1, 126.2, 126.4, 127.4, 127.7, 128.5, 129.1, 129.3, 132.9, 133.2, 137.5, 148.2, 150.9, 156.4, 171.9. Anal. Calcd for C$_{33}$H$_{41}$N$_5$O$_2$: C, 73.43; H, 7.65; N, 12.98. Found: C, 73.08: H, 7.71; N, 12.89.

A hemihydrate 9.1/2 H$_2$O was obtained by crystallization of crude 9 from wet ethyl acetate, mp 181–182° C. Anal. Calcd for 9.1/2 H$_2$O: C, 72.22; H, 7.71; N, 12.76. Found: C, 72.19; H, 7.76; N, 12.72.

Discussion

Several synthetic approaches to the title compound and analogs have been evaluated. This compound is a practical precursor to N-substituted 2-(2-naphthyl)quinolin-4-amines, the triple-helix DNA specific intercalators.

The triple-helix structure of nucleic acids is formed by binding a single strand of DNA in the major groove of duplex DNA. The interaction is highly base sequence specific but is quite unstable under normal physiological conditions. Various biotechnology applications have led to an increased intercast in stabilization of the triplex DNA form. For example, the formation of a stable triplex structure between a short oligonucleotide and a specific sequence in a long duplex DNA can be used to inhibit expression of the specific gene. Alternatively, with an appropriate cleaving group attached to the third-strand oligomer, highly specific cleavage of DNA can be achieved.

One approach to enhance triplex stability is to design compounds that bind strongly and specifically to triplex DNA but weakly to duplex DNA. Another strategy is to tether such compounds to the triplex-forming oligonucleotide, so that the triplex structure can be stabilized efficiently by intramolecular interactions.

Several DNA intercalators are known to interact nonselectively with triple and double DNA structures or stabilize the triple helix relative to the corresponding duplex with various selectivities. Compound 2 and other N$^4$-substituted 2-(2-naphthyl)quinolin-4-amines are far superior in their triplex stabilization ability and the triplex/duplex binding selectivity than any other triplex intercalators reported to date. These unfused bi-aromatic derivatives bind to and stabilize strongly and selectively T-AT triplets of the triple-helix DNA in the presence of duplex DNA of any sequence.

In this study critically examine several synthetic approaches to such triplex DNA intercalators. The preparation of a standard intercalator 2 and the synthesis of compound 9 with a terminal hydroxy group for the attachment to the 5'-end of an oligonucleotide by using phosphoramidite chemistry serve as examples. A similar strategy can be used for the synthesis of analogs of 9 containing a terminal 1,2-diol functionality for linking to the 3'-end of an oligonucleotide.

Quinoline 2 has been obtained previously by two methods, namely, (i) lithium 2-(dimethylamino)-ethylamide mediated cyclization of ketimine 1 derived from 2-(trifluoromethyl)aniline and acetonaphthone and (ii) nucleophilic displacement of fluoride in 4-fluoroquinoline 3 with N,N-dimehtylethylenediamine. Unfortunately, the short and efficient route (i) is not applicable to the preparation of other quinolines substituted with a primary alkylamino function at position 4.

The attractiveness of the second method (ii) as a general route to 4-(substituted alkylamino) quinolines is severely hampered by the low yield of 4-fluoroquinoline 3 obtained by the reaction of 2-(trifluoromethyl)aniline with the lithium enolate of acetonaphthone and a tedious purification that requires several consecutive chromatographic separations. Numerous attempts to optimize the synthesis of 3 did not succeed. The 33% yield of 3 obtained on a 200-mg scale decreased to 5–15% for the reactions conducted on a 2-g scale under a variety of experimental conditions. These experiments included the published conditions and reactions conducted in different solvents (ether, hexanes, and ether/hexanes, in the presence and absence of hexamethylphosphoramide) with varying ratios of the reagents and at varying temperatures.

Inventors focused their attention on 2-arylquinolin-4(1H)-ones that could be transformed into the corresponding quinolines substituted with other nucleofugal groups at position 4. A method described by Staskun failed to produce the desired 2-(2-naphthyl)quinolin-4(1H)-one (5). The successful synthetic route to 5 involves potassium tert-butoxide mediated cyclization of ketimine 1. This reaction furnished a mixture of a 4-tert-butoxyquinoline 4 and quinolin-4(1H)-one 5 in 51% and 15% yields, respectively. The tert-butoxy derivative 4 was efficiently converted into 6 (93% yield), a p-toluenesulfonate salt of 5, by treatment with p-toluenesulfonic acid. The subsequent reaction of either 5 or 6 with phosphorus oxychloride afforded 4-chloro-2-(2-naphthyl) quinoline (7) in 75% yield. The use of phosphorus oxychloride improved the efficiency of this reaction to 86%. Larger amounts of phosphorus pentachloride did not increase the yield of 7 but used potential safety hazards during workup. Substitution of p-toluenesulfonyl chloride for $POCl_3$ furnished 2-(2-naphthyl)-4-[(p-tolylsulfonyl)oxy]quinoline (8). Unfortunately, the treatment of 8 with a primary amine did to cause displacement of the sulfonate group but resulted in cleavage of the S—O bond and gave quinoline 5 quantitatively. Initial attempts at displacing chloride from 7 by primary amines also did not succeed. Thus, in contrast to the reactivity of its fluoro analog 3, the 4-chloroquinoline 7 was inert in attempted reactions with amines at 120° C. After 6 h at 150° C., the starting material 7 was still present and a large number of products had formed, as observed by TLC analysis. The nucleophilic displacement of chloride easily took place, however, in the presence of a catalytic amount of tin tetrachloride. Such a treatment of 7 with N,N-dimethylethylenediamine gave the known intercalator 2. In the synthesis of the desired triplex DNA intercalator 9, compound 7 was treated with an excess of 1,4-bis(3-aminopropyl)piperazine in the presence of $SnCl_4$ followed by a reaction of the resultant intermediate mono-substituted amine, without purification, with y-butyrolactone. The efficiencies of the reactions conducted with 0.5 g of 7 or scaled up to 5 g were virtually identical. The yield of the two-step transformation of 7 to 9 was 56%, and the overall yield of 9 from 1 was 27%.

In summary, a practical method is described for the synthesis of 4-chloro-2-(2-naphthyl)quinoline (7) and shown that compound 7 is a good substrate for the preparation of triple-helix DNA intercalators. Products, such as 9, that are compatible with phosphoramidite chemistry can be used in the preparation of triple-helix DNA intercalator-oligonucleotide conjugates.

Example 11
Preparation of bis-4-guinolinamines and bis-9-aminoacridines

Materials and Methods

General Procedure. A mixture of 4-chloro-2-(-naphthyl) quinoline (300 mg, 1.0 mmol), an α,ω-diamine (H-R-H, 0.05 mmol), and a catalytic amount of $SnCl_4$ (30 μL) was heated in a Parr bomb to 140° C. for 3.5 h. N,N-Bis[3-[2-(2-naphthyl)quinolin-4-amino]propyl]methylamine was crystallized as a hydrobromine salt, and the purification of 1,4-Bis[3-[2-(2-naphthyl)quinolin-4-amino]propyl] piperazine and N,N-Bis[2-(2-naphthyl)quinolin-4-yl]]4,9-dioxa-1,12-dodecanediamine was conducted by silica gel chromatography of free bases eluting with AcOEt followed by crystallization of the free bases.

N,N-Bis[3-[2-(2-naphthyl)quinolin-4-amino] propyl]methylamine: yield 52% of $C_{45}H_{41}N_5$.3HBr.$H_2O$; mp 257–262° C.; $^1$H NMR δ2.29 (m, 4H), 2.82 (s, 3H), 3.28 (m, 4H), 3.82 (m, 4H), 7.27 (s, 2H), 7.64 (m, 6H), 7.92 (t, J=8 Hz, 2H), 8.02 (d, J=8 Hz, 2H) 8.15 (t, J=8 Hz, 4H), 8.21 (t, J=8 Hz, 4H), 8.69 (d, J=8 Hz, 2H), 8.80 (s, 2H), 9.50 (br, exchangeable with $D_2O$), 11.10 (br, exchangeable with $D_2O$). Anal. Calcd for $C_{45}H_{41}N_5$.3HBr.$H_2O$; C, 59.40; H, 4.88; N, 7.70, Found: C, 59.70; H, 5.12; N, 7.59.

1,4-Bis[3-[2-(2-naphthyl)quinolin-4-amino]propyl] piperazine: yield 60% of the free base; mp 192–198° C; 1H NMR δ1.90 (m, 4H), 2.48 (m, 4H), 3.35 (s, 8H), 3.52 (m, 4H), 7.15 (s, 2H), 7.44 (t, J=8 Hz, 2H), 0.50 (br, exchangeable with $D_2O$), 7.55 (m, 4H), 7.66 (t, J=8 Hz, 2H), 7.92 (d, J=8 Hz, 2H), 7.96 (m, 2eH), 8.04 (d, J=8 Hz, 2H), 8.09 (m, 2H), 8.24 (d, J=8 Hz, 2H), 8.38 (d, J=8 Hz, 2H), 8.17 (s, 2H). Anal. Calcd for $C_{48}H_{46}N_6$.$H_2O$: C, 79.52; H, 6.67; N, 11.60. Found: C, 79.39; H, 7.04; N, 11.70.

N,N-Bis[2-(2-naphthyl)quinolin-4-yl]]4,9-dioxa-1,12-dodecanediamine: yield 40% of the free base; mp 115–117° C.; $^1$H NMR δ1.44 (m, 4H), 1.93 (m, 4H), 3.31 (m, 4H), 3.42 (m, 4H), 3.58 (m, 4H), 7.10 (s, 2H), 7.53 (t, J=8 Hz, 2H), 7.57 (m, 4H), 7.78 (t, J=8 Hz, 2H), 7.96 (m, 2H), 8.06 (m, 6H), 8.22 (m, 6H), 8.22 (d, J=8 Hz, 2H), 8.26 (br, exchangeable with $D_2O$), 8.41 (d, J=8 Hz, 2H), 8.67 (s, 2H). Anal. Calcd for $C_{48}H_{46}N_4O_2$.$H_2O$: C, 79.09; H, 6.64; N, 7.69. Found: C, 78.70; H, 6.69; N, 7.41.

Bis[3-[2-(2-naphthyl)quinolin-4-amino]propyl] Succinate

A solution of 4-chloro-(2-napthyl) quinoline (420 mg, 1.4 mmol) in 3-aminopropanol (1.0 mL) was heated to 130° C. for 1.5 h under a nitrogen atmosphere. Treatment with water (2 mL) was followed by extraction of the mixture with AcOEt, drying of the extract with $MgSO_4$, and concentration to give a residue of crude N-(3-hydroxypropyl)-2-(2-naphthyl)quinolin-4-amine. This compound was purified by silica gel chromatography eluting with $CH_2Cl_2$/MeOH (5:1) followed by crystallization of its hydrobromide salt; yield 82% of $C_{22}H_{20}N_2O$.HBr.$H_2O$; mp 230–235° C. Anal. Calcd for $C_{22}H_{20}N_2O$.HBr.$H_2O$: C, 61.82: H, 5.43; N, 6.55. Found: C, 61.98; H, 5.28; N, 6.49.

A mixture of $C_{22}H_{20}N_2O$.HBr.$H_2O$ (530 mg, 1.25 mmol), $SOCl_2$ (1.0 mL), and benzene (5 mL) was heated under reflux for 1.5 h. Following concentration on a rotary evaporator, the oily residue was treated with AcOEt (25 mL) and an aqueous solution of $NaHCO_3$ (10%, 10 mL), and the mixture was stirred briefly. The organic layer was separated, dried ($MgSO_4$), and concentrated. The residue of crude N-(3-chloropropyl)-2-(2-naphthyl)quinolin-4-amine was purified by silica gel chromatography eluting with hexanes/ether (1:2) and then crystallized; yield 75%; mp 131–135° C. HRMS. Calcd for $C_{22}H_{19}^{35}ClN_2$: m/z 346.1254. Found m/z 346.1240.

N-(3-chloropropyl)-2-(2-naphthyl)quinolin-4-amine (208 mg, 0.6 mmol), succinic acid (30 mg, 0.3 mmol), and DBU (90 μL, 0.6 mmol) in anhydrous DMF (1.0 mL) was heated to 90° C. for 6 h under a nitrogen atmosphere. Following concentration on a rotary evaporator, the residue of bis[3-[2-(2-naphthyl)quinolin-4-amino]propyl] succinate was subjected to silica gel chromatography eluting with $CH_2Cl_2$/i-PrOH (5:1). Then it was transformed into a hydrobromide salt, and the salt was crystallized; yield 30% of $C_{48}H_{42}N_4O_4$.3HBr.2.5$H_2O$; mp 210–216° C.; $^1$H NMR δ2.10 (m, 4H), 2.52 (s, 4H), 4.04 (m, 4H), 4.15 (m, 4H), 7.65 (m, 10H), 7.79 (d, J=8 Hz, 2H), 7.98 (m, 4H), 8.07 (m, 4H), 8.14 (d, J=8 Hz, 2H), 8.30 (s, 2H), 8.52 (d, J=8 Hz, 2H). Anal. Calcd for $C_{48}H_{42}N_4O_4$.3HBr.2.5$H_2O$: C, 56.13; H, 4.87; N, 5.45. Found: C, 56.03; H, 4.62; N, 5.52.

Quinolin-4-amines

A mixture of 4-chloro-(2-napthyl) quinoline (600 mg, 2.1 mmol), N,N-bis(3-aminopropyl)methylamine or 1,3-propanediamine (3 mL), and $SnCl_4$ (50 µL) was heated to 140° C. for 4 h under a nitrogen atmosphere. Removal of excess amine under reduced pressure was followed by treatment of the residue with hydrobromic acid and then crystallization of the resultant salt.

N-[3-[N-3-Aminopropyl)methylamino]propyl]quinolin-4-amine: yield 64% of $C_{26}H_{30}N_4.3HBr$; mp 232–235° C.; $^1$H NMR δ2.02 (m, 2H), 2.23 (m, 2H), 2.84 (s, 3H) 2.92 (m, 2H), 3.28 (m, 4H), 3.83 (m, 2H), 7.13 (s, 1H), 7.16 (m, 2H), 7.30 (t, J=8 Hz, 1H), 7.91 (br, exchangeable with $D_2O$), 8.02 (t, J=8 Hz, 1H), 8.11 (d, J=8 Hz, 1H) 8.20 (m, 4H), 8.71 (d, J=8 Hz, 1H), 8.81e (s, 1H), 9.44 (br, exchangeable with $D_2O$), 9.82 (br, exchangeable with $D_2O$).Anal. Calcd for $C_{26}H_{30}N_4.3HBr$: C, 35.43; H, 4.11; N, 6.36. Found: C, 35.53; H, 3.99; N, 6.12.

N-(3-Aminopropyl)-2-(2-naphthyl)quinolin-4-amine: yield 61% of $C_{22}H_{21}N_3.2HBr.1.5H_2O$; mp 280–284° C.; $^1$H NMR δ2.13 (m, 2H), 3.03 (m, 2H), 3.24 (br, exchangeable with $D_2O$), 3.85 (m, 2H), 7.27 (s, 1H), 7.70 (m, 3H), 7.95 (br, exchangeable with $D_2O$), 7.99 (t, J=8 Hz, 1H), 8.07 (d, J=8 Hz, 1H), 8.18 (m, 3H), 8.24 (t, J=8 Hz, 1H), 8.71 (d, J=8 Hz, 1H), 8.79 (s, 1H), 9.37 (br, exchangeable with $D_2O$). Anal. Calcd for $C_{22}H_{21}N_3.2HBr.1.5H_2O$: C, 51.17; H, 5.09; N, 8.14. Found: C, 51.19; H, 4.85; N, 7.96.

1,4-Bis[3[(3-carboxypropionamido)propy1]]piperazine

A solution of 1,4-bis(3-aminopropyl)piperazine (1.0 mL, 4.8 mmol) and succinic anhydride (1.0 g, 10.0 mmol) in anhydrous DMF (20 mL) was heated to 70° C. for 1 h under a nitrogen atmosphere. The resultant precipitate was filtered, washed with EtOH, and crystallized from DMF: yield 57%; mp 179–180° C.; $^1$H NMR ($D_2O$) δ1.87 (m, 4H), 2.51 (m, 8H), 2.93 (m, 4H), 3.24 (m, 12H). Anal. Calcd for $C_{18}H_{32}N_4O_6$: C, 54.00; H, 8.05; N, 14.00. Found: C, 53.99; H, 8.20; N, 13.98.

A General Procedure for the Preparation of the Remaining Three Compounds. A mixture of succinic acid or 1,4-bis[3[(3-carboxypropionamido)propy1]]piperazine (0.3 mmol), triethylamine (0.25 mL, 1.8 mmol), and BOP (225 mg, 0.6 mmol) in anhydrous DMF (4 mL) was stirred at 23° C. for 15 min before treatment with a salt $C_{26}H_{30}N_4.3HBr$ or $C_{22}H_{21}N_3.2HBr.1.5H_2O$ (0.6 mmol). The mixture was stirred at 23° C. for 24 h and then filtered. The solution was concentrated on a rotary evaporator and a residue of a crude product was transformed into a hydrobromide salt, and the salt crystallized.

N,N-Bis[3-[N-[3-[2-(2-naphthyl)quinolin-4-amino]propyl]methylamino]-propyl]succinamide (from N-[3-[N-3-aminopropyl)methylamino]propyl]quinolin-4-amine and succinic acid): yield 73% of $C_{56}H_{62}N_8O_2.5HBr.5H_2O$; mp 232–240° C.; $^1$H NMR δ1.81 (m, 4H), 2.19 (m, 4H), 2.31 (s, 3H), 2.78 (s, 4H), 3.09 (m, 8H), 3.27(m, 4H), 3.81 (m, 4H), 7.27 (s, 2H), 7.71 (m, 6H), 8.01 (m, 4H), 8.10 (m, 2H), 8.16 (m, 4H), 8.23 (d, J=8 Hz, 2H), 8.62 (d, J=8 Hz, 2H), 8.74 (s, 2H), 9.30 (br, exchangeable with $D_2O$), 9.55 (br, exchangeable with $D_2O$). Anal. Calcd for $C_{56}H_{62}N_8O_2.5HBr.5H_2O$: C, 49.02; H, 5.24; N, 8.19. Found: C, 48.89; H, 5.35; N, 8.55.

1,4-Bis[3-[[N-[3-[2-(2-naphthyl)quinolin-4-amino]propyl]succinamoyl]amino]-propyl]piperazine (from N-(3-aminopropyl)-2-(2-naphthyl)quinolin-4-amine and 1,4-bis[3[(3-carboxypropionamido)propyl]]piperazine): yield 47% of $C_{62}H_{70}N_{10}O_4.4HBr$; mp 290–296° C.; $^1$H NMR δ1.86 (m, 8H), 2.64 (s, 8H), 2.7–3.6 (m, 24H), 7.21 (s, 2H), 7.71 (m, 6H), 7.87 (br, exchangeable with $D_2O$), 8.01 (t, J=8 Hz, 2H), 8.15 (m, 10H), 8.62 (d, J=8 Hz, 2H), 8.71 (s, 2H). Anal. Calcd for $C_{62}H_{70}N_{10}O_4.4HBr$; C, 44.78; H, 4.60; N, 8.42. Found: C, 44.69; H, 4.86; N, 8.24.

1,4-Bis[3-[[N-[3-[N-[2-(2-naphthyl)quinolin-4-amino]propyl]methylamino]propyl]succinamoyl]amino]propyl]piperazine (from N-[3-[N-3-aminopropyl)methylamino]propyl]quinolin-4-amine and 1,4-bis[3[(3-carboxypropionamido)propy1]]piperazine): yield 46% of $C_{70}H_{88}N_{12}O_4.9HBr.2H_2O$; mp 234–240° C.; 1H NMR δ1.89 (m, 8H), 2.08 (m, 4H), 2.32 (m, 4H), 2.56 (m, 8H), 2.65 (s, 8H), 2.82 (s, 6H), 2.94 (m, 4H), 3.11 (m, 4H), 3.34 (m, 4H), 3.87 (m, 8H), 7.30 (s, 2H), 7.71 (m, 6H), 7.93 (br, exchangeable with $D_2O$), 8.01 (t, J=8 Hz, 2H), 8.08 (d, J=8 Hz, 2H), 8.21 (m, 8H), 8.74 (d, J=8 Hz, 2H), 8.81 (s, 2H), 9.38 (br, exchangeable with $D_2O$), 9.93 (br, exchangeable with $D_2O$). Anal. Calcd for $C_{70}H_{88}N_{12}O_4.9HBr.2H_2O$: C, 43.64; H, 5.28; N, 8.73. Found: C, 43.81; H, 5.43; N, 8.46.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,016,100
U.S. Pat. No. 4,089,801
U.S. Pat. No. 4,234,871
U.S. Pat. No. 4,485,054
Ballas, Rasmussen, Krieg, "Induction of NK activity in murine and human cells by CpG motifs in oligodeoxynucleotides and bacterial DNA," *J. Immunology*, 157:1840–1845, 1996.
Bammel, Brand, Germon, Smith, "Interaction of the extrinsic potential-sensitive molecular probe diS-C3-(5) with pigeon heart mitochondria under equilibrium and time-resolved conditions," *Arch. Biochem. Biophys.*, 244:67–84, 1986.
Bangham et al., *J. Mol. Biol.* 13:238–252, 1965.
Brown, "Fully automated baseline correction of 1D and 2D NMR spectra using bernstein polynomials," *Magn. Reson.*, Series A 114:268–270,1995.
Deamer and Uster, "Liposome Preparation: Methods and Mechanisms," In: *Liposomes, M. Ostro (Ed.)*, 1983
de Duve, C.; de Barsy, T.; Poole, B.; Trouet, A.; Tulkens, P.; van Hoof, F. *Biochem. Pharm.*, 23, 1974.
Drug Carriers In Biology and Medicine, G. Gregoriadis ed., pp. 287–341, 1979.
Duve, Barsy, Poole, Trouet, Tulkens, van Hoof, "Lysosomotropic agents," *Biochem. Pharm*, 23, 1974.

Ellena, Dominey, Archer, Xu, Cafiso, "Localization of hydrophobic ions in phospholipid bilayers using 1H nuclear Overhauser effect spectroscopy," *Biochem.*, 26:4584–4592, 1987.

Fitch, Yunis, Chevli, Gonzalez, "High affinity accumulation of chloroquine by mouse erythrocytes infected with Plasmodium berghei," *J. Clin. Invest.*, 54:24–33, 1974.

Fox, "Mechanism of action of hydroxychloroquine as an antirheumatic drug," *Sem. Arthritis Rheumatism*, 23:82–91, 1993.

Ghosh and Bachhawat, Targeting of Liposomes to Hepatocytes. In: *Liver Diseases, Targeted Diagnosis and Therapy Using Specific Receptors and Ligands*. Wu et al., eds., Marcel Dekker, New York, pp. 87–104, 1991.

Gray, "Linear prediction guide," *Magn. Moments*, 7:30–33, 1990.

Ismail, Dascombe, Carr, North, "An exploration of the structure-activity relationships of 4-aminoquinolines: novel antimalarials with activity in-vivo," *J. Pharm. Pharmacol.*, 48:841–850, 1996.

Krieg et al., "Lymphocyte activation by CpG dinucleotide motifs in prokaryotic DNA," *Trends Microbiol.*, 4(2):73–6, 1996.

Krieg, Matson, Fisher, "Oligodeoxynucleotide modifications determine the magnitude of B cell stimulation by CpG motifs," *Antisense Nucleic Acid Drug Dev.*, 6(2): 133–9, 1996.

Krieg, Yi, Matson, Waldschmidt, Bishop, Teasdale, Koretzky, Klinman, "CpG motifs in bacterial DNA trigger direct B-cell activation," *Nature*, 374:546–549, 1995.

MacFarlane and Manzel, "Antagonism of immunostimulatory CpG-oligodeoxynucleotides by quinacrine, chloroquine and structurally related compounds," *J. Immunol.*, 160:1122–1131, 1998.

MacFarlane, Manzel, Krieg, "Unmethylated CpG-containing oligodeoxynucleotides inhibit apoptosis in WEHI 231 B-lymphocytes induced by several agents: evidence for blockade at a distal signaling step," *Immunology*, 91:586–593, 1997.

Mokrosz, J. L.; Duszynska, B.; Strekowski, L. *Pharmazie;* and references cited therein, 47:538, 1992.

Ohkuma and Poole, "Cytoplasmic vacuolation of mouse peritoneal macrophages and the uptake into lysosomes of weakly basic substances," *J. Cell. Biol.*, 90:656–664, 1981.

Ohkuma and Poole, "Fluorescence probe measurements of the intralysosomal pH in living cells and the perturbation of pH by various agents," *Proc. Natl. Acad. Sci. USA*, 75:3327–3331, 1978.

Remington's Pharmaceutical Sciences, 15th ed., Mack Publishing Company, Easton, Pa., 1980.

States, Haberkorn, Rubin, "A two-dimensional nuclear overhauser experiment with pure absorption phase in four quadrants," *Magn. Reson.*, 48:286–292, 1982.

Strekowski, Kiselyov, Hojjat, "The o-amino-trifluoromethyl functionality as a novel synthon for 4-fluoroquinolines," *J. Org. Chem.*, 59:5886–5890, 1994.

Strekowski, L.; Gulevich, Y.; Baranowski, T. C.; Parker, A. N.; Kiselyov, A. S.; Lin, S.-Y.: Tanious, F. A.; Wilson, W. D. *J. Med. Chem.* 39:3980, 1996.

Strekowski, L.; Janda, L.; Patterson, S. E.; Nguyen, J. *Tetrahedron*, 52:3273, 1996.

Strekowski, L.; Zegrocka, O.; Windham, C.; Czarny, A. *Org. Process Res. Dev.*, 1:384, 1997.

Strekowski, Patterson, Janda, Wydra, Harden, Lipowska, Cegl, "Further studies on the cyclization of aromatic azaomethines ortho-substituted with a trifluoromethyl group: Synthesis of 2,4-di- or 2,3,4-trisubstituted quinolines," *Org. Chem.*, 57, 1992.

Strekowski, Wilson, Mokrosz, Mokrosz, Harden, Tanious, Wydra, Crow, Jr., "Quantitative structure-activity relationship analysis of cation-substituted polyaromatic compounds as potentiators (amplifiers) of bleomycin-mediated degradation of DNA," *J. Med. Chem.*, 34:580–588, 1991.

Szoka and Papahadjopoulos, *Proc. Natl. Acad. Sci. USA*, 75: 4194–4198, 1978.

Tonkinson and Stein, "Patterns of intracellular compartmentalization, trafficking and acidification of 5'-fluorescein labeled phosphodiester and phosphorothioate oligodeoxynucleotides in HL60 cells," *Nucleic Acid Res.*, 22:4268–4275, 1994.

Wallace, "Antimalarial agents and lupus," *Rheumatic Disease Clinics of Portly America*, 20:243–263, 1994.

Wawrzynczak & Thorpe "Methods for Preparing Immunotoxins: Effect of the Linkage on Activity and Stability", In: *Immunoconjugates: Antibody Conjugates in Radioimaging and Therapy of Cancer*, Vogel (ed.), New York, Oxford University Press, pp. 28–55, 1987.

Wilson, 1998. "DNA and RNA intercalators," In: *DNA and aspects of molecular biology*, Kool (ed.), Vol. 7, 1998.

Wilson, W. D.; Ratmeyer, L.; Zhao, M.; Strekowski, L.; Boykin, D. *Biochemistry*, 32:4098, 1993.

Yi, Hornbeck, Lafrenz, Krieg, "CpG DNA rescue of murine B lymphoma cells from anti-IgM induced growth arrest and programmed cell death is associated with expression of c-myc, c-myb, myn, and bcl-2," *J. Immunol.*, 157:4918–4925, 1996.

Yi, Tuetken, Redford, Waldschmidt, Kirsch, Krieg, "CpG motifs in bacterial DNA activate leukocytes through the pH-dependent generation of reactive oxygen species," *J. Immunol.*, 160:4755–4761, 1998.

What is claimed is:

1. A method of inhibiting immunostimulation in a subject, the method comprising administering an effective amount of a substituted 4-quinolinamine composition to said subject, the 4-quinolinamine composition comprising a compound having the structural formula A wherein $R_A$ is hydrogen atom or a lower alkyl group;

$R_B$ is a substituted or unsubstituted alkyl, alkenyl or alkynyl secondary or tertiary amine;

$R_2$ is a unsubstituted or substituted phenyl group, a unsubstituted or substituted naphthyl group, an substituted or unsubstituted anthracyl group, a substituted or unsubstituted phenanthryl group or a substituted or unsubstituted styryl group;

$R_3$ is a hydrogen atom;

$R_5$ is a hydrogen atom;

$R_6$ is a hydrogen atom or a halogen atom;

$R_7$ is a hydrogen atom; and $R_8$ is a hydrogen atom, and pharmaceutically acceptable salts thereof.

2. The method of claim 1, wherein said $R_2$ phenyl, naphthyl, anthracyl, styryl or phenanthryl group substitution is further defined as one or more substitutions selected from the group consisting of an alkyl group, an alkoxy group, an alkoxyalkyl group, an ester group, an alkylamino group, a dialkylamino group, a cyclic amino group, a halogen atom and any combination thereof.

3. The method of claim 2, wherein said cyclic amino group is a piperazino group, a piperidino group, a pyrrolidino group, an imidazolyl group, pyridyl group, or a morpholino group.

4. The method of claim 1, wherein said $R_B$ alkyl substitution is selected from the group consisting of a cyclic amino group, an alkylamino group, a dialkylamino, furyl, phenyl, thienyl, and any combination thereof.

5. The method of claim 4, wherein said cyclic amino group is a piperazino group, a piperidino group, a pyrrolidino group, an imidazolyl group, a pyridyl group, or a morpholino group.

6. A method of inhibiting immunostimulation in a subject, the method comprising administering an effective amount of a substituted 4-quinolinamine composition to said subject, the 4-quinolinamine composition comprising a compound having the structural formula B

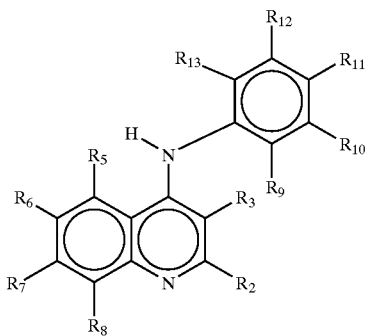

wherein the phenyl group can be substituted at $R_9$, $R_{10}$, $R_{11}$, $R_{12}$ and $R_{13}$, wherein said substituted phenyl group comprises one or more substitutions selected from the group consisting of an alkyl group, an alkoxy group, a hydroxy group, an alkylaminoalkyl group, an alkoxyalkyl group, an ester group, an alkylamino group, a dialkylamino group, a cyclic amino group, a furan group, a thiophene group, a halogen atom or any combination thereof;

$R_2$ is a substituted or unsubstituted phenyl group, a substituted or unsubstituted naphthyl group, a substituted or unsubstituted anthracyl group, a substituted or unsubstituted styryl group or a substituted or unsubstituted phenanthryl group;

$R_3$ is a hydrogen atom;

$R_5$ is a hydrogen atom;

$R_6$ is a hydrogen atom or a halogen atom;

$R_7$ is a hydrogen atom, a halogen atom or an alkyl halogen atom;

$R_8$ is a hydrogen atom, and pharmaceutically acceptable salts thereof.

7. The method of claim 6, wherein said cyclic amino group is a piperazino group, a piperidino group, a pyrrolidino group, an imidazolino group or a morpholino group.

8. The method of claim 7, wherein said piperidino group is 4-alkyl piperazino.

9. The method of claim 6, wherein the $R_2$ phenyl, naphthyl, anthracyl, styryl or phenanthryl group substitution is further defined as one or more substitutions selected from the group consisting of an alkyl group, an alkoxy group, a hydroxy group, an alkoxyalkyl group, an ester group, an alkylamino group, a dialkylamino group, a cyclic amino group, a halogen atom or any combination thereof.

10. The method of claim 9, wherein said cyclic amino group is a piperazino group, a piperidino group, a pyrrolidino group, an imidazolino group or a morpholino group.

11. A method of inhibiting immunostimulation in a subject, the method comprising administering an effective amount of a substituted 4-quinolinamine composition to said subject, the 4-quinolinamine composition comprising a compound having the structural formula C

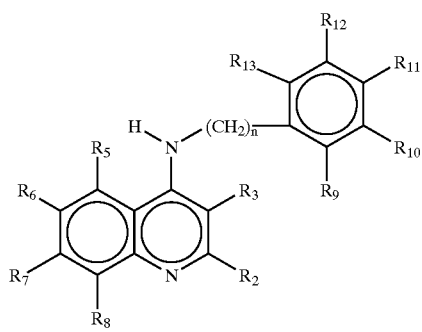

wherein the phenyl group can be unsubstituted or substituted at $R_9$, $R_{10}$, $R_{11}$, $R_{12}$ and $R_{13}$, wherein said substituted phenyl group comprises one or more substitutions selected from the group consisting of an alkyl group, an alkoxy group, an alkoxyalkyl group, an alkylaminoalkyl group, a hydroxy group, an ester group, an alkylamino group, an dialkylamino group, a cyclic amino group, a furan group, a thiophene group, a halogen atom, or any combination thereof;

n is 0 to 4 $CH_2$;

$R_2$ is a substituted or unsubstituted phenyl group, a substituted or unsubstituted naphthyl group, a substituted or unsubstituted anthracyl group, a substituted or unsubstituted styryl group or a substituted or unsubstituted phenanthryl group;

$R_3$ is a hydrogen atom;

$R_5$ is a hydrogen atom;

$R_6$ is a hydrogen atom or a halogen atom;

$R_7$ is a hydrogen atom, a halogen atom or an alkyl halogen atom;

$R_8$ is a hydrogen atom, and pharmaceutically acceptable salts thereof.

12. The method of claim 11, wherein said cyclic amino group is a piperazino group, a piperidino group, a pyrrolidino group, an imidazolino group or a morpholino group.

13. The method of claim 11, wherein the $R_2$ phenyl, naphthyl, anthracyl, styryl or phenanthryl group substitution is further defined as one or more substitutions selected from the group consisting of an alkyl group, an alkoxy group, hydroxy group, an alkoxyalkyl group, an ester group, an alkylamino group, an dialkylamino group, a cyclic amino group, a halogen atom or any combination thereof.

14. The method of claim 13, wherein said cyclic amino group is a piperazino group, a piperidino group, a pyrrolidino group, an imidazolino group or a morpholino group.

15. A method of inhibiting immunostimulation in a subject, the method comprising administering an effective amount of a substituted bis-4-quinolinamine composition to said subject, the bis-4-quinolinamine composition comprising a compound having the structural formula D

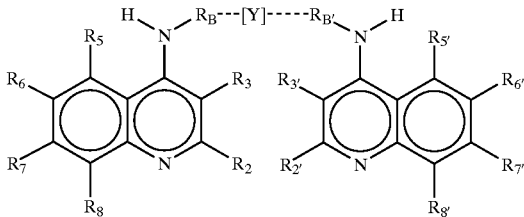

wherein
- $R_B$ on the first 4-quinolinamine is covalently attached to $R_{B'}$ on the second 4-quinolinamine by linker group Y, wherein the linker group Y is an alkyl group, an ester group, an alkoxyalkyl group, an alkylamino group, an dialkylamino group, an amido group, a cyclohexane, a cyclohexanediyl, a piperazino group, 1–4, piperazinediyl, or any combination thereof;
- $R_2$ is a substituted or unsubstituted phenyl group, a substituted or unsubstituted naphthyl group, a substituted or unsubstituted anthracyl group, a substituted or unsubstituted styryl group or a substituted or unsubstituted phenanthryl group;
- $R_3$ is a hydrogen atom;
- $R_5$ is a hydrogen atom;
- $R_6$ is a hydrogen atom or a halogen atom;
- $R_7$ is a hydrogen atom or a halogen atom;
- $R_8$ is a hydrogen atom;
- $R_{2'}$ is a substituted or unsubstituted phenyl group, a substituted or unsubstituted naphthyl group, an substituted or unsubstituted anthracyl group, a substituted or unsubstituted styryl group or a substituted or unsubstituted phenanthryl group;
- $R_{3'}$ is a hydrogen atom;
- $R_{5'}$ is a hydrogen atom;
- $R_{6'}$ is a hydrogen atom or a halogen atom;
- $R_{7'}$ is a hydrogen atom or a halogen atom; and
- $R_{8'}$ is a hydrogen atom, and pharmaceutically acceptable salts thereof.

16. The method of claim 15, wherein the $R_2$ phenyl, naphthyl, anthracyl, styryl or phenanthryl group substitution is further defined as one or more substitutions selected from the group consisting of an alkyl group, an alkoxy group, an alkoxyalkyl group, a hydroxy group, an ester group, an alkylamino group, an dialkylamino group, a cyclic amino group, a halogen atom or any combination thereof.

17. The method of claim 16, wherein said cyclic amino group is a piperazino group, a piperidino group, a pyrrolidino group, an imidazolino group or a morpholino group.

18. The method of claim 15, wherein the $R_{2'}$ phenyl, naphthyl, anthracyl, styryl or phenanthryl group substitution is further defined as one or more substitutions selected from the group consisting of an alkyl group, an alkoxy group, an alkoxyalkyl group, a hydroxy group, an ester group, an alkylamino group, an dialkylamino group, a cyclic amino group, a halogen atom or any combination thereof.

19. The method of claim 18, wherein said cyclic amino group is a piperazino group, a piperidino group, a pyrrolidino group, an imidazolino group or a morpholino group.

20. The method of claim 19, wherein said linker is α,ω-alkanediyl.

21. A method of inhibiting immunostimulation in a subject, the method comprising administering an effective amount of a substituted bis-9-aminoacridine composition to said subject, the bis-9-aminoacridine composition comprising a compound having the structural formula E

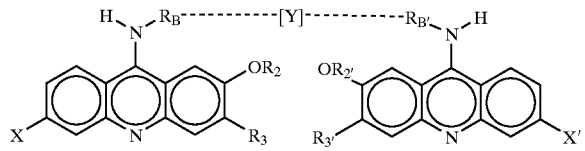

wherein
- $R_B$ on the first 9-aminoacridine is covalently attached to $R_{B'}$ on the second 9-aminoacridine by linker group Y, wherein the linker group Y is an alkyl group, an ester group, an alkoxyalkyl group, an alkylamino group, an dialkylamino group, an amido group, a cyclohexane, a cyclohexanediyl, a piperazino group, 1–4, piperazinediyl, or any combination thereof;
- $OR_2$ is a lower alkyl group;
- $OR_{2'}$ is a lower alkyl group;
- $R_3$ is a hydrogen atom or a lower alkoxy group;
- $R_{3'}$ is a hydrogen atom or a lower alkoxy group;
- X is a halogen atom;
- X' is a halogen atom, and pharmaceutically acceptable salts thereof.

22. The method of claim 21, wherein said linker is α,ω-alkanediyl.

23. A method of inhibiting immunostimulation in a subject, the method comprising administering an effective amount of a composition to said subject, the composition comprising a compound having the structural formula F

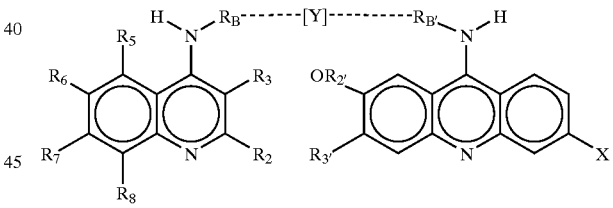

wherein
- $R_B$ is covalently linked to $R_{B'}$ by linker Y, wherein the linker group Y is an alkyl group, an ester group, an alkoxyalkyl group, an alkylamino group, an dialkylamino group, an amido group, a cyclohexane, a cyclohexanediyl, a piperazino group, 1–4, piperazinediyl, or any combination thereof;
- $R_2$ is a substituted or unsubstituted phenyl group, a substituted or unsubstituted naphthyl group, an substituted or unsubstituted anthracyl group, a substituted or unsubstituted styryl group or a substituted or unsubstituted phenanthryl group;
- $R_3$ is a hydrogen atom;
- $R_5$ is a hydrogen atom;
- $R_6$ is a hydrogen atom or a halogen atom;
- $R_7$ is a hydrogen atom or a halogen atom;
- $R_8$ is a hydrogen atom;
- $R_{B'}$ is linked covalently to $R_B$ by linker Y;

OR$_2$' is a lower alkyl group; and

R$_3$' is a hydrogen atom, or a lower alkoxy group;

X is a halogen atom, and pharmaceutically acceptable salts thereof.

24. The method of claim 23, wherein said R$_2$ phenyl, naphthyl, anthracyl, styryl or phenanthryl group substitution is further defined as one or more substitutions selected from the group consisting of an alkyl group, an alkoxy group, an alkoxyalkyl group, a hydroxy group, an ester group, an alkylamino group, an dialkylamino group, a cyclic amino group, a halogen atom or any combination thereof.

25. The method of claim 24, wherein said cyclic amino group is a piperazino group, a piperidino group, a pyrrolidino group, an imidazolino group or a morpholino group.

26. The method of claim 23, wherein said linker is α,ω-alkanedieyl.

27. A substituted 4-quinolinamine composition having the structural formula A

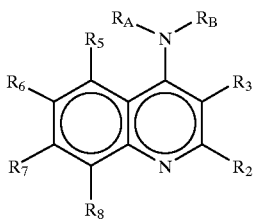

wherein

R$_A$ is hydrogen atom or a lower alkyl group;

R$_B$ is a substituted or unsubstituted alkyl, alkenyl or alkynyl secondary or tertiary amine;

R$_2$ is a substituted naphthyl group, an substituted or unsubstituted anthracyl group, a substituted or unsubstituted phenanthryl group or a substituted or unsubstituted styryl group;

R$_3$ is a hydrogen atom;

R$_5$ is a hydrogen atom;

R$_6$ is a hydrogen atom or a halogen atom;

R$_7$ is a hydrogen atom or a halogen atom; and

R$_8$ is a hydrogen atom, and pharmaceutically acceptable salts thereof.

28. The composition of claim 27, wherein said R$_2$ phenyl, naphthyl, anthracyl, styryl or phenanthryl group substitution is further defined as one or more substitutions selected from the group consisting of an alkyl group, an alkoxy group, an alkoxyalkyl group, a hydroxy group, an ester group, an alkylamino group, a dialkylamino group, a cyclic amino group, a halogen atom and any combination thereof.

29. The composition of claim 28, wherein said cyclic amino group is a piperazino group, a piperidino group, a pyrrolidino group, an imidazolyl group, a pyridyl group, or a morpholino group.

30. The composition of claim 27, wherein said R$_B$ alkyl substitution is selected from the group consisting of a cyclic amino group, furyl, thienyl, alkylamino group, dialkylamino group, phenyl, and any combination thereof.

31. The composition of claim 30, wherein said cyclic amino group is a piperazino group, a piperidino group, a pyrrolidino group, an imidazolyl group, a pyridyl group, or a morpholino group.

32. A substituted 4-quinolinamine composition having the structural formula B

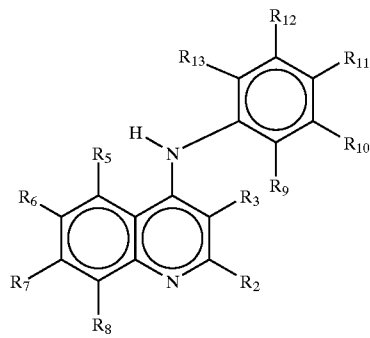

wherein the phenyl group can be substituted at R$_9$, R$_{10}$, R$_{11}$, R$_{12}$ and R$_{13}$, wherein said substituted phenyl group comprises one or more substitutions selected from the group consisting of an alkyl group, an alkoxy group, an alkoxyalkyl group, an alkylaminoalkyl group, an ester group, an alkylamino group, an dialkylamino group, a cyclic amino group, a furan group, a thiophene group, a halogen atom or any combination thereof;

R$_2$ is a substituted or unsubstituted phenyl group, a substituted or unsubstituted naphthyl group, a substituted or unsubstituted anthracyl group, a substituted or unsubstituted styryl group or a substituted or unsubstituted phenanthryl group;

R$_3$ is a hydrogen atom;

R$_5$ is a hydrogen atom;

R$_6$ is a hydrogen atom or a halogen atom;

R$_7$ is a hydrogen atom, a halogen atom or an alkyl halogen atom;

R$_8$ is a hydrogen atom, and pharmaceutically acceptable salts thereof.

33. The composition of claim 32, wherein said cyclic amino group is a piperazino group, a piperidino group, a pyrrolidino group, an imidazolino group or a morpholino group.

34. The composition of claim 33, wherein said cyclic amino group is 4-alkyl-piperazino.

35. The composition of claim 32, wherein the R$_2$ phenyl, naphthyl, anthracyl, styryl or phenanthryl group substitution is further defined as one or more substitutions selected from the group consisting of an alkyl group, an alkoxy group, an alkoxyalkyl group, an ester group, an alkylamino group, a hydroxy group, a dialkylamino group, a cyclic amino group, a halogen atom or any combination thereof.

36. The composition of claim 35, wherein said cyclic amino group is a piperazino group, a piperidino group, a pyrrolidino group, an imidazolino group or a morpholino group.

37. A substituted 4-quinolinamine composition having the structural formula C

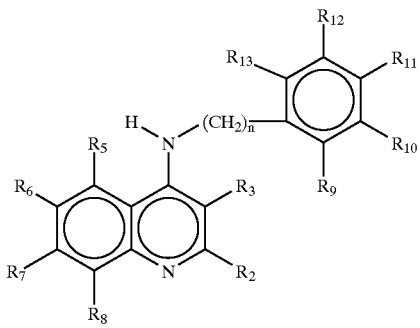

wherein the phenyl group can be unsubstituted or substituted at $R_9$, $R_{10}$, $R_{11}$, $R_{12}$ and $R_{13}$, wherein said substituted phenyl group comprises one or more substitutions selected from the group consisting of an alkyl group, an alkoxy group, an alkoxyalkyl group, an alkylaminoalkyl group, an ester group, an alkylamino group, an dialkylamino group, a cyclic amino group, a furan group, a thiophene group, a halogen atom, or any combination thereof;

n is 0 to 4 $CH_2$;

$R_2$ is a substituted or unsubstituted phenyl group, a substituted or unsubstituted naphthyl group, a substituted or unsubstituted anthracyl group, a substituted or unsubstituted styryl group or a substituted or unsubstituted phenanthryl group;

$R_3$ is a hydrogen atom;

$R_5$ is a hydrogen atom;

$R_6$ is a hydrogen atom or a halogen atom;

$R_7$ is a hydrogen atom, a halogen atom or an alkyl halogen atom;

$R_8$ is a hydrogen atom, and pharmaceutically acceptable salts thereof.

38. The composition of claim 37, wherein said cyclic amino group is a piperazino group, a piperidino group, a pyrrolidino group, an imidazolino group or a morpholino group.

39. The composition of claim 37, wherein the $R_2$ phenyl, naphthyl, anthracyl, styryl or phenanthryl group substitution is further defined as one or more substitutions selected from the group consisting of an alkyl group, an alkoxy group, an alkoxyalkyl group, an ester group, an alkylamino group, an dialkylamino group, a cyclic amino group, a halogen atom or any combination thereof.

40. The composition of claim 39, wherein said cyclic amino group is a piperazino group, a piperidino group, a pyrrolidino group, an imidazolino group or a morpholino group.

41. A substituted bis-4-quinolinamine composition having the structural formula D

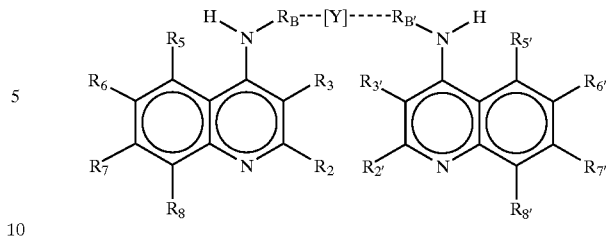

wherein $R_B$ on the first 4-quinolinamine is covalently attached to $R_{B'}$ on the second 4-quinolinamine by linker group Y, wherein the linker group Y is an alkyl group, an ester group, an alkoxyalkyl group, an alkylamino group, an dialkylamino group, an amido group, a cyclohexane, a cyclohexanediyl, a piperazino group, 1-4, piperazinediyl, or any combination thereof;

$R_2$ is a substituted phenyl group, a substituted or unsubstituted naphthyl group, a substituted or unsubstituted anthracyl group, a substituted or unsubstituted styryl group or a substituted or unsubstituted phenanthryl group;

$R_3$ is a hydrogen atom;

$R_5$ is a hydrogen atom;

$R_6$ is a hydrogen atom or a halogen atom;

$R_7$ is a hydrogen atom or a halogen atom;

$R_8$ is a hydrogen atom;

$R_{2'}$ is a substituted or unsubstituted phenyl group, a substituted or unsubstituted naphthyl group, an substituted or unsubstituted anthracyl group, a substituted or unsubstituted styryl group or a substituted or unsubstituted phenanthryl group;

$R_{3'}$ is a hydrogen atom;

$R_{5'}$ is a hydrogen atom;

$R_{6'}$ is a hydrogen atom or a halogen atom;

$R_{7'}$ is a hydrogen atom or a halogen atom; and $R_{8'}$ is a hydrogen atom, and pharmaceutically acceptable salts thereof.

42. The composition of claim 41, wherein the $R_2$ phenyl, naphthyl, anthracyl, styryl or phenanthryl group substitution is further defined as one or more substitutions selected from the group consisting of an alkyl group, an alkoxy group, an alkoxyalkyl group, an ester group, an alkylamino group, an dialkylamino group, a cyclic amino group, a halogen atom or any combination thereof.

43. The composition of claim 42, wherein said cyclic amino group is a piperazino group, a piperidino group, a pyrrolidino group, an imidazolino group or a morpholino group.

44. The composition of claim 41, wherein the $R_2$ phenyl, naphthyl, anthracyl, styryl or phenanthryl group substitution is further defined as one or more substitutions selected from the group consisting of an alkyl group, an alkoxy group, an ether group, an ester group, an alkylamino group, an dialkylamino group, a cyclic amino group, a halogen atom or any combination thereof.

45. The composition of claim 44, wherein said cyclic amino group is a piperazino group, a piperidino group, a pyrrolidino group, an imidazolino group or a morpholino group.

46. A substituted bis-9-aminoacridine composition having the structural formula E

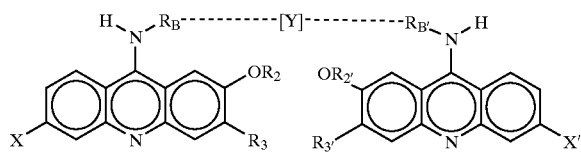

wherein
- $R_B$ on the first 9-aminoacridine is covalently attached to $R_{B'}$ on the second 9-aminoacridine by linker group Y, wherein the linker group Y is an alkyl group, an ester group, an alkoxyalkyl group, an alkylamino group, an dialkylamino group, an amido group, a cyclohexane, a cyclohexanedieyl, a piperazino group, 1–4, piperazinedieyl, or any combination thereof;
- $OR_2$ is a lower alkyl group;
- $OR_{2'}$ is a lower alkyl group;
- $R_3$ is a lower alkoxy group;
- $R_{3'}$ is a lower alkoxy group;
- X is a halogen atom;
- X' is a halogen atom, and pharmaceutically acceptable salts thereof.

47. A 4-quinolinamine, 9-aminoacridine composition having the structural formula F

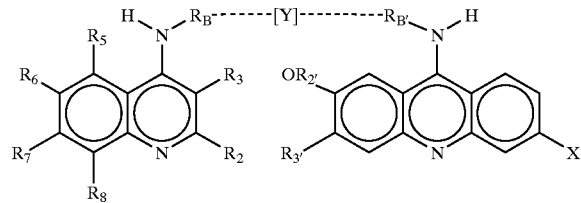

wherein
- $R_B$ is covalently linked to $R_{B'}$ by linker Y, wherein the linker group Y is an alkyl group, an ester group, an alkoxyalkyl group, an alkylamino group, an dialkylamino group, an amido group, a cyclohexane, a cyclohexanedieyl, a piperazino group, 1–4, piperazinedieyl, or any combination thereof;
- $R_2$ is a substituted or unsubstituted phenyl group, a substituted or unsubstituted naphthyl group, an substituted or unsubstituted anthracyl group, a substituted or unsubstituted styryl group or a substituted or unsubstituted phenanthryl group;
- $R_3$ is a hydrogen atom;
- $R_5$ is a hydrogen atom;
- $R_6$ is a hydrogen atom or a halogen atom;
- $R_7$ is a hydrogen atom or a halogen atom;
- $R_8$ is a hydrogen atom;
- $R_B'$ is linked covalently to $R_B$ by linker Y;
- $OR_2'$ is a lower alkyl group; and
- $R_3'$ is a hydrogen atom, or a lower alkoxy group;
- X is a halogen atom, and pharmaceutically acceptable salts thereof.

48. The composition of claim 47, wherein said $R_2$ phenyl, naphthyl, anthracyl, styryl or phenanthryl group substitution is further defined as one or more substitutions selected from the group consisting of an alkyl group, an alkoxy group, an alkoxyalkyl group, an ester group, an alkylamino group, an dialkylamino group, a cyclic amino group, a halogen atom or any combination thereof.

49. The composition of claim 48, wherein said cyclic amino group is a piperazino group, a piperidino group, a pyrrolidino group, an imidazolino group or a morpholino group.

* * * * *

UNITED STATES PATENT AND TRADEMARK OFFICE
CERTIFICATE OF CORRECTION

PATENT NO. : 6,479,504 B1
DATED : November 12, 2002
INVENTOR(S) : Macfarlane et al.

It is certified that error appears in the above-identified patent and that said Letters Patent is hereby corrected as shown below:

<u>Title page,</u>
Item [73], please insert -- Australia National University, Australian Capital Territory, (AU). --.

<u>Column 51,</u>
Line 49, please delete "or any" and insert -- and any -- therefor.

<u>Column 52,</u>
Lines 7, 39 and 64, please delete "or any" and insert -- and any -- therefor.

<u>Column 53,</u>
Line 64, please delete "or any" and insert -- and any -- therefor.

<u>Column 54,</u>
Line 2, please delete "α,ω)- alkanedieyl" and insert -- α,ω- alkanedieyl -- therefor.

<u>Column 55,</u>
Line 11, please delete "or any" and insert -- and any -- therefor.

<u>Column 56,</u>
Lines 26 and 59, please delete "or any" and insert -- and any -- therefor.

<u>Column 57,</u>
Lines 27 and 59, please delete "or any" and insert -- and any -- therefor.

<u>Column 58,</u>
Line 50, please delete "or any" and insert -- and any -- therefor.
Line 60, please delete "or any" and insert -- and any -- therefor.

UNITED STATES PATENT AND TRADEMARK OFFICE
CERTIFICATE OF CORRECTION

PATENT NO. : 6,479,504 B1
DATED : November 12, 2002
INVENTOR(S) : Macfarlane et al.

It is certified that error appears in the above-identified patent and that said Letters Patent is hereby corrected as shown below:

<u>Column 60,</u>
Line 31, please delete "or any" and insert -- and any -- therefor.

Signed and Sealed this

Fifteenth Day of April, 2003

JAMES E. ROGAN
*Director of the United States Patent and Trademark Office*